US009315786B2

(12) United States Patent
Reed et al.

(10) Patent No.: US 9,315,786 B2
(45) Date of Patent: Apr. 19, 2016

(54) GSK3 LIGANDS AND POLYNUCLEOTIDES ENCODING GSK3 LIGANDS

(71) Applicant: Intrexon Corporation, Blacksburg, VA (US)

(72) Inventors: Thomas D. Reed, Arlington, VA (US); Amy H. Atzel, Minneapolis, MN (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 14/255,821

(22) Filed: Apr. 17, 2014

(65) Prior Publication Data

US 2014/0273227 A1 Sep. 18, 2014

Related U.S. Application Data

(62) Division of application No. 11/937,685, filed on Nov. 9, 2007, now Pat. No. 8,729,225.

(60) Provisional application No. 60/865,587, filed on Nov. 13, 2006.

(51) Int. Cl.
| | |
|---|---|
| *A61K 8/64* | (2006.01) |
| *C12N 1/15* | (2006.01) |
| *C12N 1/21* | (2006.01) |
| *C12N 5/10* | (2006.01) |
| *C12N 15/00* | (2006.01) |
| *C12N 9/10* | (2006.01) |
| *C07K 14/47* | (2006.01) |
| *C12N 15/85* | (2006.01) |

(52) U.S. Cl.
CPC .............. *C12N 9/1051* (2013.01); *C07K 14/47* (2013.01); *C12N 15/85* (2013.01)

(58) Field of Classification Search
None
See application file for complete search history.

(56) References Cited

U.S. PATENT DOCUMENTS

| | | | |
|---|---|---|---|
| 6,780,625 B2 * | 8/2004 | Eldar-Finkelman | 435/194 |
| 7,071,295 B2 | 7/2006 | Reed | |
| 7,705,122 B2 | 4/2010 | Reed et al. | |
| 7,943,732 B2 | 5/2011 | Reed | |
| 8,153,598 B2 | 4/2012 | Reed | |
| 8,283,445 B2 | 10/2012 | Reed | |
| 8,575,304 B2 | 11/2013 | Reed et al. | |
| 8,603,807 B2 | 12/2013 | Reed | |
| 8,729,225 B2 | 5/2014 | Reed et al. | |
| 2001/0052137 A1 | 12/2001 | Klein | |
| 2004/0185556 A1 | 9/2004 | Reed | |
| 2008/0032947 A1 | 2/2008 | Reed | |
| 2008/0050808 A1 | 2/2008 | Reed et al. | |
| 2008/0051360 A1 | 2/2008 | Reed et al. | |
| 2008/0220475 A1 | 9/2008 | Reed et al. | |
| 2009/0186379 A1 | 7/2009 | Reed | |
| 2009/0215173 A1 | 8/2009 | Reed | |
| 2009/0215866 A1 | 8/2009 | Reed | |

FOREIGN PATENT DOCUMENTS

| | | |
|---|---|---|
| WO | WO 01/70770 A2 | 9/2001 |
| WO | WO 2005/040336 A2 | 5/2005 |
| WO | WO 2005/116231 A1 | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Sang, H. "Prospects for transgenesis in the chick", Mechanisms of Development 121:1179-1186, 2004.*
Makrides, S., "Components of Vectors for Gene Transfer and Expression in Mammalian Cells", Prot. Exp. Purif. 17:183-202, 1999.*
Fiol et al., "Ordered Multisite Protein Phosphorylation", J. Biol. Chem. 265:6061-6065, 1990.*
Kaburagi et al., "Insulin-Induced Cell Cycle Progression Is Impaired in Chinese Hamster Ovary Cells Overexpressing Insulin Receptor Substrate-3", Endocrinology 145:5862-5874, 2004.*
Bax, et al., "The structure of phosphorylated GSK-3beta complexed with a peptide, FRATtide, that inhibits beta-catenin phosphorylation," *Structure* 9:1143-1152 (2001).
Beals, et al., "Nuclear export of NF-ATc enhanced by glycogen synthase kinase-3," *Science* 275:1930-1934 (1997).
Casaday, et al., "Assembly protein precursor (pUL80.5 homolog) of simian cytomegalovirus is phosphorylated at a glycogen synthase kinase 3 site and its downstream "priming" site: phosphorylation affects interactions of protein with itself and with major capsid protein," *J. Virol.* 78:13501-11 (2004).
Chu, et al., "Sequential phosphorylation by mitogen-activated protein kinase and glycogen synthase kinase 3 represses transcriptional activation by heat shock factor-1," *J. Biol. Chem.* 271:30847-30857 (1996).
Cole, et al., "Further evidence that the tyrosine phosphorylation of glycogen synthase kinase-3 (GSK3) in mammalian cells is an autophosphorylation event," *Biochem. J.* 377:249-55 (2004).
Fiol, et al., "Ordered multisite protein phosphorylation. Analysis of glycogen synthase kinase 3 action using model peptide substrates," *J. Biol. Chem.* 265:6061-6065 (1990).
Frame, et al., "GSK3 takes centre stage more than 20 years after its discovery," *Biochem. J.* 359:1-16 (2001).
Fujimuro, et al., "Regulation of the interaction between glycogen synthase kinase 3 and the Kaposi's sarcoma-associated herpesvirus latency-associated nuclear antigen," *J Virol* 79:10429-10441 (2005).
Godemann, et al., "Phosphorylation of tau protein by recombinant GSK-3beta: pronounced phosphorylation at select Ser/Thr-Pro motifs but no phosphorylation at Ser262 in the repeat domain," *FEBS Letters* 454:157-164 (1999).

(Continued)

*Primary Examiner* — David J Steadman
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands and polyligands that modulate GSK3 activity. The ligands and polyligands are utilized as research tools or as therapeutics. The invention includes linkage of the ligands and polyligands to a cellular localization signal, epitope tag and/or a reporter. The invention also includes polynucleotides encoding the ligands and polyligands.

10 Claims, 12 Drawing Sheets

(56) References Cited

OTHER PUBLICATIONS

Hughes, et al., "Identification of multifunctional ATP-citrate lyase kinase as the alpha-isoform of glycogen synthase kinase-3," *Biochem. J.* 288 (Pt 1):309-314 (1992).

Kirschenbaum, et al., "Substitution of a glycogen synthase kinase-3beta phosphorylation site in presenilin 1 separates presenilin function from beta-catenin signaling," *J. Biol. Chem.* 276:7366-7375 (2001).

Liberman, et al., "Serine 332 phosphorylation of insulin receptor substrate-1 by glycogen synthase kinase-3 attenuates insulin signaling," *J. Biol. Chem.* 280:4422-4438 (2005).

Litovchick, et al., "Glycogen synthase kinase 3 phosphorylates RBL2/p130 during quiescence," *Mol. Cell. Biol.* 24:8970-8980 (2004).

Liu, et al., "Functional characterisation of the regulation of CAAT enhancer binding protein alpha by GSK-3 phosphorylation of Threonines 222/226," *BMC Mol. Biol.* 7:14 (2006).

Medunjanin, et al., "Glycogen synthase kinase-3 interacts with and phosphorylates estrogen receptor alpha and is involved in the regulation of receptor activity," *J. Biol. Chem.* 280:33006-33014 (2005).

Nikolakaki, et al., "Glycogen synthase kinase 3 phosphorylates Jun family members in vitro and negatively regulates their transactivating potential in intact cells," *Oncogene* 8:833-840 (1993).

Piwien-Pilipuk, et al., "Growth hormone regulates phosphorylation and function of CCAAT/enhancer-binding protein beta by modulating Akt and glycogen synthase kinase-3," *J. Biol. Chem.* 276:19664-19671 (2001).

Plotkin, et al., "Insulin mimetic action of synthetic phosphorylated peptide inhibitors of glycogen synthase kinase-3," *J. Pharmacol. Exp. Ther.* 305:974-80 (2003).

Rhoads, "Signal transduction pathways that regulate eukaryotic protein synthesis," *J Biol. Chem.* 274:30337-30340 (1999).

Rubinfeld, et al., "Binding of GSK3beta to the APC-beta-catenin complex and regulation of complex assembly," *Science* 272:1023-1026 (1996).

Ryan, et al., "Activation of GSK-3 and phosphorylation of CRMP2 in transgenic mice expressing APP intracellular domain," *J. Cell. Biol.* 171:327-335 (2005).

Sato, et al., "Aberrant tau phosphorylation by glycogen synthase kinase-3beta and JNK3 induces oligomeric tau fibrils in COS-7 cells," *J. Biol. Chem.* 277:42060-42065 (2002).

Sheorain, et al., "Phosphorylation of sites 3 and 2 in rabbit skeletal muscle glycogen synthase by a multifunctional protein kinase (ATP-citrate lyase kinase)," *J. Biol. Chem.* 260:12287-12292 (1985).

Takeda, et al., "Ser298 of MITF, a mutation site in Waardenburg syndrome type 2, is a phosphorylation site with functional significance," *Hum. Mol. Genet.* 9:125-132 (2000).

Trivedi, et al., "Glycogen synthase kinase-3beta phosphorylation of MAP1B at Ser1260 and Thr1265 is spatially restricted to growing axons," *J. Cell. Sci.* 118:993-1005 (2005).

Welsh, et al., "Peptide substrates suitable for assaying glycogen synthase kinase-3 in crude cell extracts," *Anal. Biochem.* 244:16-21 (1997).

Ji, Y., et al.,, "Targeted Inhibition of $Ca^{2+}$/Calmodulin-dependant Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc., United States (2003).

Kosuga, S., et al. "GSK-3β Directly Phosphorylates and Activates MARK2/PAR-1*," *J. Biol. Chem.* 280(52):42715-42722, The American Society for Biochemistry and Molecular Biology, Inc., United States (2005).

Thomas, G.M., et al. "A GSK3-binding peptide from FRAT1 selectively inhibits the GSK3-catalysed phosphorylation of Axin and β-catenin," *FEBS Letters* 458:247-251, Elsevier Science by, Netherlands (1999).

Fraser, E., et al. "Identification of the Axin and Frat Binding Region of Glycogen Synthase Kinase-3*," *J. Biol. Chem.* 277(3):2176-2186, The American Society for Biochemistry and Molecular Biology, Inc., United States (2002).

Lawrewnce, D.S., "New Design Strategies for Ligands That Target Protein Kinase-Mediated Protein-Protein Interactions," *Handbook of Exp. Pharm.* 167:11-44, Springer-Verlag, Germany (2005).

Office Action mailed Jun. 26, 2009 in U.S. Appl. No. 11/937,685, filed Nov. 9, 2007, inventor T. Reed et al.

Office Action mailed Dec. 15, 2009 in U.S. Appl. No. 11/937,685, filed Nov. 9, 2007, inventor T. Reed et al.

Office Action mailed May 16, 2013 in U.S. Appl. No. 11/937,685, filed Nov. 9, 2007, inventor T. Reed et al.

Office Action mailed Sep. 19, 2013 in U.S. Appl. No. 11/937,685, filed Nov. 9, 2007, inventor T. Reed et al.

* cited by examiner

| LIGAND X | LIGAND X |
|---|---|

FIGURE 1A

| LIGAND X | LIGAND X | LIGAND X |
|---|---|---|

FIGURE 1B

| LIGAND X | LIGAND X | LIGAND X | LIGAND X | LIGAND X |
|---|---|---|---|---|

FIGURE 1C

| LIGAND X | SPACER | LIGAND X |

FIGURE 2A

| LIGAND X | SPACER | LIGAND X | SPACER | LIGAND X |

FIGURE 2B

| LIGAND X | LIGAND X | SPACER | LIGAND X | SPACER | LIGAND X |

FIGURE 2C

| LIGAND X | LIGAND Y |

FIGURE 3A

| LIGAND X | LIGAND Y | LIGAND Z |

FIGURE 3B

| LIGAND X | LIGAND Y | LIGAND X | LIGAND Z | LIGAND A |

FIGURE 3C

| LIGAND A | LIGAND B | LIGAND C | LIGAND D |

FIGURE 3D

| LIGAND A | LIGAND A | LIGAND B | LIGAND C |

FIGURE 3E

| LIGAND A | SPACER | LIGAND B |

FIGURE 4A

| LIGAND X | SPACER | LIGAND Y | SPACER | LIGAND Z |

FIGURE 4B

| LIGAND X | LIGAND Y | SPACER | LIGAND Y | LIGAND X |

FIGURE 4C

| LIGAND A | SPACER | LIGAND B | SPACER | LIGAND C | SPACER | LIGAND D |

FIGURE 4D

| LIGAND A | LIGAND A | SPACER | LIGAND B | LIGAND C |

FIGURE 4E

| LIGAND X | SPACER | LIGAND Y | SPACER | LIGAND Z | SPACER | LIGAND Y |

FIGURE 4F

| LIGAND X | LIGAND X | EPITOPE |

FIGURE 5A

| EPITOPE | LIGAND X | LIGAND Y |

FIGURE 5B

| LIGAND X | SPACER | LIGAND X | EPITOPE |

FIGURE 5C

| EPITOPE | LIGAND X | SPACER | LIGAND Y |

FIGURE 5D

| LIGAND X | SPACER | LIGAND Y | SPACER | LIGAND A | LIGAND B | EPITOPE |

FIGURE 5E

| EPITOPE | LIGAND X | SPACER | LIGAND Y | LIGAND A | LIGAND B |

FIGURE 5F

| LIGAND X | EPITOPE |

FIGURE 5G

| LIGAND X | LIGAND X | REPORTER |

FIGURE 6A

| REPORTER | LIGAND X | LIGAND Y |

FIGURE 6B

| LIGAND X | SPACER | LIGAND X | REPORTER |

FIGURE 6C

| REPORTER | LIGAND X | SPACER | LIGAND Y |

FIGURE 6D

| LIGAND X | SPACER | LIGAND Y | SPACER | LIGAND A | LIGAND B | REPORTER |

FIGURE 6E

| REPORTER | LIGAND X | SPACER | LIGAND Y | LIGAND A | LIGAND B |

FIGURE 6F

| LIGAND X | REPORTER |

FIGURE 6G

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Y |

FIGURE 7G

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

FIGURE 9G

GSK3 LIGANDS AND POLYNUCLEOTIDES ENCODING GSK3 LIGANDS

This application claims benefit of priority to U.S. 60/865,587, filed 13 Nov. 2006.

REFERENCE TO SEQUENCE LISTING SUBMITTED ELECTRONICALLY VIA EFS-WEB

This application includes a "SequenceListingascii.text," 275,479 bytes; created on Aug. 31, 2015, and submitted electronically via EFS-Web, which is hereby incorporated by reference in its entirety.

FIELD OF INVENTION

The invention relates to mammalian kinase ligands, substrates and modulators. In particular, the invention relates to polypeptides, polypeptide compositions and polynucleotides that encode polypeptides that are ligands, substrates, and/or modulators of GSK3. The invention also relates to polyligands that are homopolyligands or heteropolyligands that modulate GSK3 activity. The invention also relates to ligands and polyligands tethered to a subcellular location.

This application has subject matter related to application Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231), PCT/US06/60065, PCT/US06/60062. Each of these patents and applications is hereby incorporated by reference.

BACKGROUND OF THE INVENTION

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian Gycogen Synthase Kinase-3 is also known as GSK3. GSK3, which has alpha and beta isoforms, can phosphorylate serine and threonine residues in protein or peptide substrates. GSK3 also autophosphorylates itself on a tyrosine residue. Some, but not all, in vivo GSK3 phosphorylation events depend upon prior phosphorylation of the substrate by another cellular kinase. The enzymatic activity, activation and regulation of GSK3 have been studied. Many cellular substrates of GSK3 have been identified. Furthermore, polypeptides have been studied to examine GSK3 substrate specificity. While polypeptides and variants thereof have been studied as individual GSK3 substrates or ligands, mixed ligands linked together as polyligands that modulate GSK3 activity have not been demonstrated before this invention. An aspect of the invention is to provide novel, modular, inhibitors of GSK3 activity by modifying one or more natural substrates either by truncation or by amino acid substitution. A further aspect of the invention is the subcellular localization of a GSK3 inhibitor, ligand, or polyligand by linking to a subcellular localization signal.

Examples of GSK3 substrates and regulators include those described in Bax, et al. 2001 Structure 9:1143-52, Beals, et al. 1997 Science 275:1930-4, Casaday, et al. 2004 J Virol 78:13501-11, Chu, et al. 1996 J Biol Chem 271:30847-57, Cole, et al. 2004 Biochem J 377:249-55, Fiol, et al. 1990 J Biol Chem 265:6061-5, Frame, et al. 2001 Biochem J 359:1-16, Fujimuro, et al. 2005 J Virol 79:10429-41, Godemann, et al. 1999 FEBS Lett 454:157-64, Hughes, et al. 1992 Biochem J 288 (Pt 1):309-14, Kirschenbaum, et al. 2001 J Biol Chem 276:7366-75, Liberman, et al. 2005 J Biol Chem 280:4422-8, Litovchick, et al. 2004 Mol Cell Biol 24:8970-80, Liu, et al. 2006 BMC Mol Biol 7:14, Medunjanin, et al. 2005 J Biol Chem 280:33006-14, Nikolakaki, et al. 1993 Oncogene 8:833-40, Piwien-Pilipuk, et al. 2001 J Biol Chem 276:19664-71, Plotkin, et al. 2003 J Pharmacol Exp Ther 305:974-80, Rhoads 1999 J Biol Chem 274:30337-40, Rubinfeld, et al. 1996 Science 272:1023-6, Ryan, et al. 2005 J Cell Biol 171:327-35, Sato, et al. 2002 J Biol Chem 277:42060-5, Sheorain, et al. 1985 J Biol Chem 260:12287-92, Takeda, et al. 2000 Hum Mol Genet 9:125-32, Trivedi, et al. 2005 J Cell Sci 118:993-1005, and Welsh, et al. 1997 Anal Biochem 244:16-21.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

DETAILED DESCRIPTION OF POLYPEPTIDE AND POLYNUCLEOTIDE SEQUENCES

SEQ ID NOS:1-12 are example polyligands and polynucleotides encoding them.

Specifically, the GSK3 polyligand of SEQ ID NO:1 is encoded by SEQ ID NO:2 and by SEQ ID NO:3, wherein the codons of have been optimized for mammalian expression. SEQ ID NO:4 includes flanking restriction sites. SEQ ID NO:1 is an embodiment of a polyligand of the structure X-X, wherein X is SEQ ID NO:119. A polyligand of structure X-X is also called herein a homopolyligand, shown generically in FIG. 1A.

SEQ ID NO:4 is an embodiment of a polyligand of the structure A-S1-B, wherein A is SEQ ID NO:117 and B is SEQ ID NO:118, and wherein S1 is a spacer of amino acid sequence GGAPAGG (SEQ ID NO:125). The GSK3 polyligand of SEQ ID NO:4 is encoded by SEQ ID NO:5 and SEQ ID NO:6, wherein the codons of have been optimized for mammalian expression. SEQ ID NO:6 includes flanking restriction sites. A polyligand of structure A-S1-B is also called herein a heteropolyligand, shown generically in FIG. 4A.

SEQ ID NO:7 is an embodiment of a polyligand of the structure X-S2-Y-S3-Z, wherein X is SEQ ID NO:120, Y is SEQ ID NO:121, Z is SEQ ID NO:116, and wherein S2 is a five amino acid spacer with the sequence GGAGG (SEQ ID NO:126) and S3 is a four amino acid spacer with the sequence GGGG (SEQ ID NO:127). The GSK3 polyligand of SEQ ID NO:7 is encoded by SEQ ID NO:8 and by SEQ ID NO:9, wherein the codons have been optimized for mammalian expression. SEQ ID NO:9 includes flanking restriction sites. A polyligand of structure X-S2-Y-S3-Z is also called herein a heteropolyligand, shown generically in FIG. 4B.

SEQ ID NO:10 is an embodiment of a polyligand of the structure X-S4-Y-S5-Z, wherein X is SEQ ID NO:48, Y is SEQ ID NO:49, Z is SEQ ID NO:50, wherein Xaa is alanine, and wherein S4 is a four amino acid spacer with the sequence AAAA (SEQ ID NO:123) and S5 is an four amino acid spacer with the sequence GGAA (SEQ ID NO:124). The GSK3 polyligand of SEQ ID NO:10 is encoded by SEQ ID NO:11, SEQ ID NO:12, wherein the codons have been optimized for mammalian expression. SEQ ID NO:12 includes flanking restriction sites. A polyligand of structure X-S4-Y-S5-Z is also called herein a heteropolyligand, shown generically in FIG. 4B.

SEQ ID NOS:13-43 are full length GSK3 protein substrates. These sequences have the following public database accession numbers: AAB69872, AAB29227, Q13144, AAH06195, AAK61224, CAA79497, NP_000029, P15941, NP_444284, NP_002219, CAA38500, NP_034722, CAA25015, AAD00450, AAC50235, NP_034013, NP_005185, AAQ24858, NP_032627, NP_937820, Q00613, P10636, P46821, NP_000012, NP_000116, AAA85777, NP_060082, NP_005535, NP_034700, NP_001377, AAD46501, NP_063937, NP_002084, NP_005470. Each of the sequences represented by these accession numbers is incorporated by reference herein. In SEQ ID NOS:13-43, the positions of the amino acid(s) phosphorylatable by GSK3 are represented by Xaa. In wild-type proteins, Xaa is serine or threonine. In the ligands of the invention, Xaa is any amino acid.

SEQ ID NO:44 and SEQ ID NO:45 are full length GSK3 alpha and beta polypeptide sequences. In SEQ ID NOS:44-45, the positions of the amino acid(s) autophosphorylatable by GSK3 are represented by Xaa. In wild-type GSK3, Xaa is tyrosine. In the ligands of the invention, Xaa is any amino acid.

SEQ ID NOS:46-111 are peptide sequences including subsequences of SEQ ID NOS:13-45, which represent examples of peptide ligand sequences where the location of the GSK3 phosphorylatable amino acid in the natural polypeptide is designated as Xaa.

SEQ ID NOS:112-114 are peptide substrates, which represent examples of peptide ligand sequences where the location of the GSK3 phosphorylatable amino acid in the natural polypeptide is designated as Xaa.

SEQ ID NOS:115-122 are inhibitors of GSK3.

SEQ ID NOS:46-122 represent examples of monomeric peptide ligand sequences.

Amino acid sequences containing Xaa encompass peptides where Xaa is any amino acid.

DETAILED DESCRIPTION OF DRAWINGS

FIGS. 1A-1C show examples of homopolymeric ligands without spacers.

FIGS. 2A-2C show examples of homopolymeric ligands with spacers.

FIGS. 3A-3E show examples of heteropolymeric ligands without spacers.

FIGS. 4A-4F show examples of heteropolymeric ligands with spacers.

FIGS. 5A-5G show examples of ligands and polymeric ligands linked to an optional epitope tag.

FIGS. 6A-6G show examples of ligands and polymeric ligands linked to an optional reporter.

FIGS. 7A-7G show examples of ligands and polymeric ligands linked to an optional localization signal.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

BRIEF DESCRIPTION OF THE INVENTION

Figure 10A:
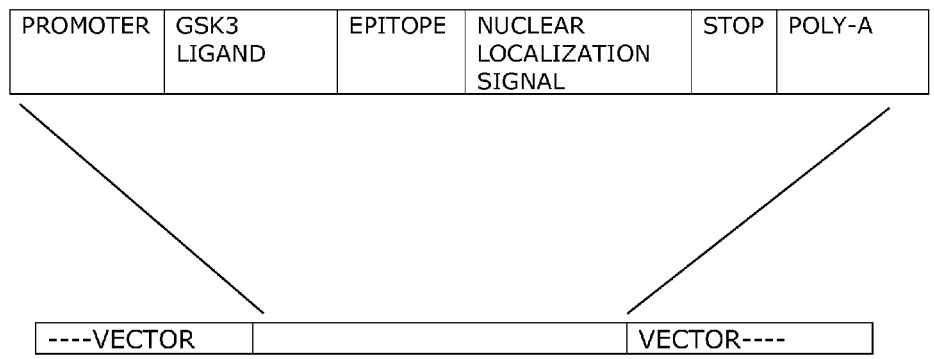
FIGS. 10A-10D show examples of vectors containing ligand gene constructs.

The invention relates to polypeptide ligands and polyligands for GSK3. Various embodiments of the GSK3 ligands and polyligands are represented in SEQ ID NOS:1-122. More specifically, the invention relates to ligands, homopolyligands, and heteropolyligands that comprise any one or more of SEQ ID NOS:46-122. Additionally, the invention relates to ligands and polyligands comprising one or more subsequences of SEQ ID NOS:13-45 or any portion thereof. Furthermore, the invention relates to polyligands with at least about 80%, 85%, 90%, 95%, 96%, 97%, 98% and 99% sequence identity to a polyligand comprising one or more of SEQ ID NOS:46-122 or any portion thereof. Furthermore, the invention relates to polyligands with at least about 80%, 85%, 90%, 95%, 96%, 97%, 98% and 99% sequence identity to a polyligand comprising one or more subsequences of SEQ ID NOS:13-45.

Polyligands, which can be homopolyligands or heteropolyligands, are chimeric ligands composed of two or more monomeric polypeptide ligands. An example of a monomeric ligand is the polypeptide represented by SEQ ID NO:57, wherein Xaa is any amino acid. SEQ ID NO:57 is a selected subsequence of wild-type full length SEQ ID NO:14, wherein the amino acid corresponding to Xaa in the wild-type sequence is a serine or threonine phosphorylatable by GSK3. An example of a homopolyligand is a polypeptide comprising a dimer or multimer of SEQ ID NO:57, wherein Xaa is any amino acid. An example of a heteropolyligand is a polypeptide comprising SEQ ID NO:46 and one or more of SEQ ID NOS:47-122, wherein Xaa is any amino acid. There are numerous ways to combine SEQ ID NOS:46-122 into homopolymeric or heteropolymeric ligands. Furthermore, there are numerous ways to combine additional subsequences of SEQ ID NOS:13-45 with each other and with SEQ ID NOS:46-122 to make polymeric ligands.

The polyligands of the invention optionally comprise spacer amino acids between monomers. SEQ ID NO:7 is an embodiment of a polyligand of the structure X-S2-Y-S3-Z, wherein X is SEQ ID NO:120, Y is SEQ ID NO:121, Z is SEQ ID NO:116, and wherein S2 and S3 are spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

A monomeric ligand is a polypeptide where at least a portion of the polypeptide is capable of being recognized by GSK3. The portion of the polypeptide capable of recognition is termed the recognition motif. In the present invention, recognition motifs can be natural or synthetic. Examples of recognition motifs are well known in the art and include, but are not limited to, naturally occurring GSK3 substrates and pseudosubstrate motifs.

A polymeric ligand comprises two or more monomeric ligands.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where some of the monomeric ligands does not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

DETAILED DESCRIPTION OF THE INVENTION

The present invention relates to ligands and polyligands that are GSK3 modulators. Various embodiments of ligands and polyligands are represented in SEQ ID NOS:1-122. Polyligands are chimeric ligands comprising two or more monomeric polypeptide ligands. An example of a monomeric ligand is the polypeptide represented by SEQ ID NO:51, wherein Xaa is any amino acid. SEQ ID NO:51 is a selected subsequence of wild-type full length SEQ ID NO:13, wherein the amino acid corresponding to Xaa in the wild-type sequence is a serine or threonine phosphorylatable by GSK3. Another example of a monomeric ligand is the polypeptide represented by SEQ ID NO:122. Each of SEQ ID NOS:46-122 represents an individual polypeptide ligand in monomeric form, wherein Xaa is any amino acid. SEQ ID NOS: 46-111 are selected examples of subsequences of SEQ ID NOS:13-45, however, other subsequences of SEQ ID NOS: 13-45 may also be utilized as monomeric ligands. Monomeric ligand subsequences of SEQ ID NOS:13-45 may be wild-type subsequences. Additionally, monomeric ligand subsequences of SEQ ID NOS:13-45 may have the GSK3 phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:46-111. Furthermore, monomeric ligands and polyligands may have at least about 80%, 85%, 90%, 95%, 96%, 97%, 98% and 99% sequence identity to a subsequence of SEQ ID NOS:13-45.

An example of a homopolyligand is a polypeptide comprising a dimer or multimer of SEQ ID NO:46, wherein Xaa is any amino acid. An example of a heteropolyligand is a polypeptide comprising SEQ ID NO:46 and one or more of SEQ ID NOS:47-122, wherein Xaa is any amino acid. There are numerous ways to combine SEQ ID NOS:46-122 into homopolymeric or heteropolymeric ligands. Furthermore, there are numerous ways to combine additional subsequences of SEQ ID NOS:13-45 with each other and with SEQ ID NOS:46-122 to make polymeric ligands.

Polyligands may comprise any two or more of SEQ ID NOS:46-122, wherein Xaa is any amino acid. A dimer or multimer of SEQ ID NO:111 is an example of a homopolyligand. An example of a heteropolyligand is a polypeptide comprising SEQ ID NO:122 and one or more of SEQ ID NOS:46-121. There are numerous ways to combine SEQ ID NOS:46-122 into homopolymeric or heteropolymeric ligands. SEQ ID NOS:46-111 are selected examples of subsequences of SEQ ID NOS:13-45, however, additional subsequences, wild-type or mutated, may be utilized to form polyligands. The instant invention is directed to all possible combinations of homopolyligands and heteropolyligands without limitation.

SEQ ID NOS:13-45 show proteins that contain at least one serine, threonine or tyrosine residue phosphorylatable by GSK3, the positions of which are represented by Xaa. SEQ ID NOS:46-111 are subsequences of SEQ ID NOS:13-45 where, again, the locations of the GSK3 phosphorylatable residues are represented by Xaa. In nature, Xaa is, generally speaking, serine, threonine or tyrosine. In one embodiment of the instant invention, Xaa can be any amino acid. Ligands where Xaa is serine or threonine or tyrosine can be used as part of a polyligand, however in one embodiment, at least one phosphorylatable serine, threonine or tyrosine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, or tryptophan. The Xaa may also be a non-naturally occurring amino acid. In another embodiment, the GSK3 phosphorylatable amino acid(s) are replaced by alanine. The ligands and polyligands of the invention are designed to modulate the endogenous effects of one or more isoforms of GSK3.

In general, ligand monomers based on natural GSK3 substrates are built by isolating a putative GSK3 phosphorylation recognition motif in a GSK3 substrate. Sometimes it is desirable to modify the phosphorylatable residue to an amino acid that cannot be phosphorylated. Additional monomers include the GSK3 recognition motif as well as amino acids adjacent and contiguous on either side of the GSK3 recognition motif. Monomeric ligands may therefore be any length provided the monomer includes the GSK3 recognition motif. For example, the monomer may comprise an GSK3 recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of GSK3 comprising at least one copy of a peptide selected from the group consisting of:

a) a peptide at least 80% identical to a peptide comprising amino acid residues corresponding to amino acid residues 638-664 of SEQ ID NO:13, wherein the amino acid residue corresponding to amino acid residue 641, 645, 649 or 653 of SEQ ID NO:13 is an amino acid residue other than serine or threonine;

b) a peptide at least 80% identical to a peptide comprising amino acid residues corresponding to amino acid residues 635-667 of SEQ ID NO:13, wherein the amino acid residue corresponding to amino acid residue 641, 645, 649 or 653 of SEQ ID NO:13 is an amino acid residue other than serine or threonine;

c) a peptide at least 80% identical to a peptide comprising amino acid residues corresponding to amino acid residues 632-671 of SEQ ID NO:13, wherein the amino acid residue corresponding to amino acid residue 641, 645, 649 or 653 of SEQ ID NO:13 is an amino acid residue other than serine or threonine; and d) a peptide at least 80% identical to a peptide comprising amino acid residues corresponding to amino acid residues 628-676 of SEQ ID NO:13, wherein the amino acid residue corresponding to amino acid residue 641, 645, 649 or 653 of SEQ ID NO:13 is an amino acid residue other than serine or threonine.

As used herein, the terms "correspond(s) to" and "corresponding to," as they relate to sequence alignment, are intended to mean enumerated positions within a reference protein, e.g., glycogen synthase (SEQ ID NO:13), and those positions that align with the positions on the reference protein. Thus, when the amino acid sequence of a subject peptide is aligned with the amino acid sequence of a reference peptide, e.g., SEQ ID NO:13, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for GSK3, such as substrates identified by SEQ ID NOS:13-114. Furthermore, if the substrate has more than one recognition motif, then more than one monomer may be identified therein.

Further embodiments of the invention include monomers based on GSK3 inhibitors and regulators, such as those identified by SEQ ID NOS:115-122 and subsequences thereof.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting GSK3 in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring GSK3 recognition motif that has been modified by addition, deletion, or substitution of one or more amino acids in the primary structure (amino acid sequence) of the motif. For example, a modified GSK3 recognition motif may be a motif where the phosphorylatable amino acid has been modified to a non-phosphorylatable amino acid. The terms "protein" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of amino acids of the query sequence that are N- and C-terminus to the reference sequence that are not matched/aligned, as a percent of the total amino acids of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids before, after or between monomers. The length and composition of the spacer may vary. An example of a spacer is glycine, alanine, polyglycine, or polyalanine Specific examples of spacers used between monomers in SEQ ID NO:10 are the four amino acids AAAA (SEQ ID NO: 123) and GGAA (SEQ ID NO: 124). Spacer amino acids may be any amino acid and are not limited to alanine and glycine. SEQ ID NO:10, depicted generically in FIG. 4B, represents a specific example of a polyligand of the structure X-S4-Y-S5-Z, wherein X, Y and Z are chosen from SEQ ID NOS:46-122, and wherein S4 and S5 are spacers. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG™ (Kodak; Rochester, N.Y.), HA (hemagluttinin), c-Myc and His6. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics. For example, ligands depicted generically in FIGS. 7A-7G represent ligands with utility as subcellular tools or therapeutics. GSK3 ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10B:
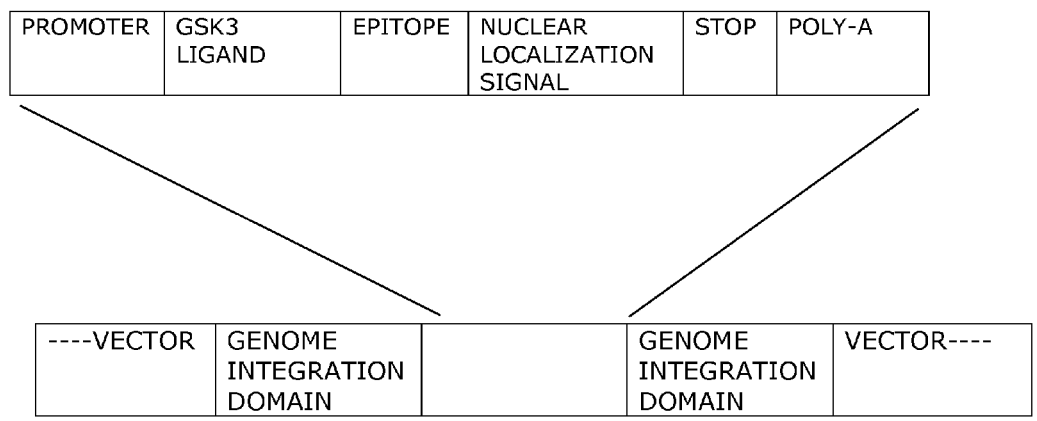
Figure 10C:
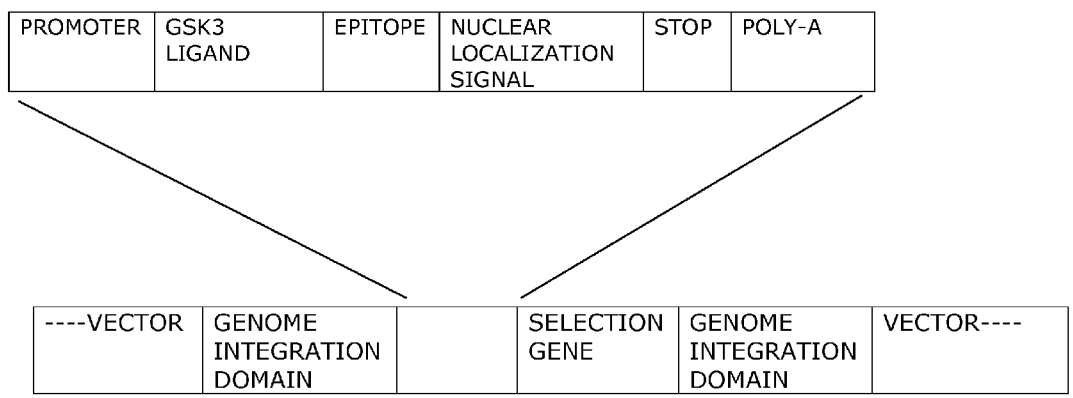

FIG. 10A shows a vector containing a GSK3 ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
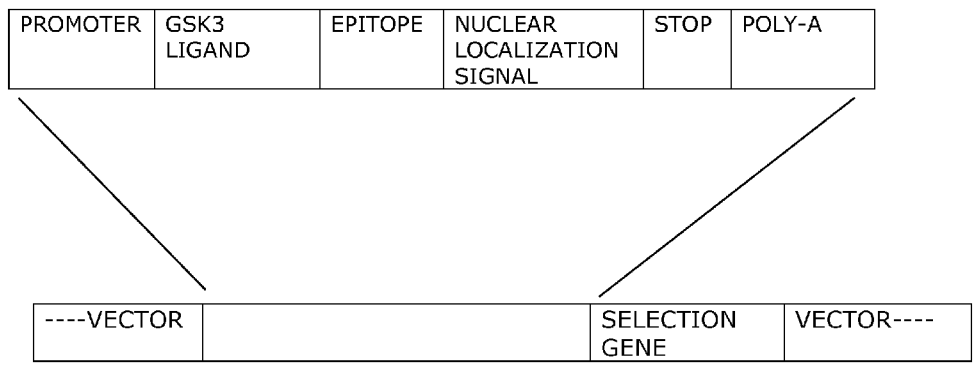

FIG. 10D shows a vector containing a GSK3 ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclease activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealed. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. RheoSwitch$^R$ is an inducible promotor system available from RheoGene. Temperature sensitive promotors can also be used to increase or decrease gene expression. An embodiment of the invention comprises a ligand or polyligand gene construct whose expression is controlled by an inducible promotor. In one embodiment, the inducible promotor is tetracycline inducible.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
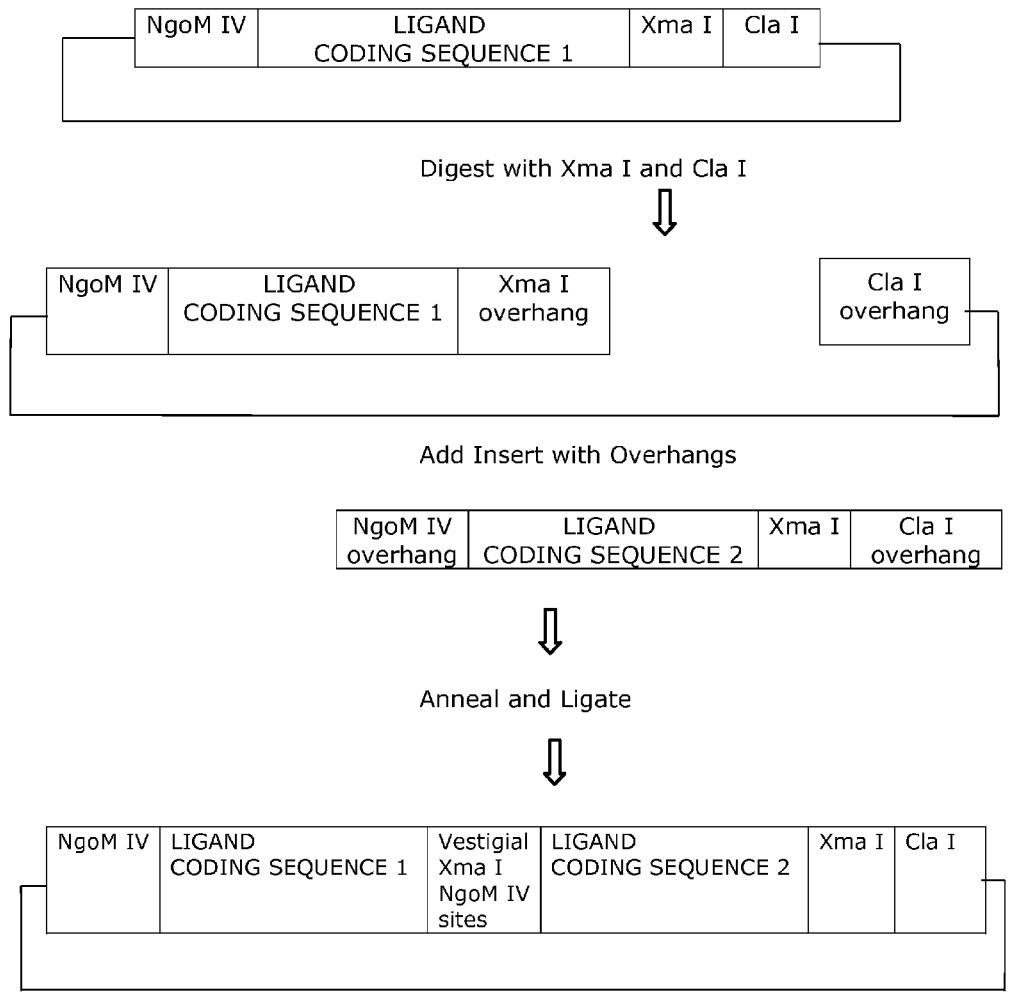
FIG. 11 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endonuclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate GSK3 activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

METHODS

Assays. Ligands of the invention are assayed for kinase modulating activity using one or more of the following methods.

Method 1. A biochemical assay is performed employing commercially-obtained kinase, commercially-obtained substrate, commercially-obtained kinase inhibitor (control), and semi-purified inhibitor ligand of the invention (decoy ligand). Decoy ligands are linked to an epitope tag at one end of the polypeptide for purification and/or immobilization, for example, on a microtiter plate. The tagged decoy ligand is made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence is employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane Cold Spring Harbor Laboratory Press, 1999).

Specifically, tagged decoy ligand synthesized using an in vitro transcription/translation system is semi-purified and added to a microtiter plate containing kinase enzyme and substrate immobilized by an anti-substrate specific antibody. Microtiter plates are rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 nm. The Control experiments include absence of kinase enzyme, and/or absence of decoy ligand, and/or presence/absence of known kinase inhibitors. A known kinase inhibitor useful in the assay is staurosporine.

Method 2. A similar assay is performed employing the same reagents as above but the substrate is biotinylated and immobilized by binding to a streptavidin-coated plate.

Method 3. A biochemical assay is performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, is then added to inversely measure kinase activity.

Specifically, tagged decoy ligand synthesized using an in vitro transcription/translation system is semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is inversely related to kinase activity. Control experiments include absence of kinase enzyme, and/or absence of decoy ligand, and/or presence/absence of known kinase inhibitors. A known kinase inhibitor useful in the assay is staurosporine.

Method 4. A similar cell-based assay is performed employing same reagents as above, but synthesizing the decoy ligand in a mammalian cell system instead of an in vitro transcription/translation system. Decoy ligands are linked to an epitope tag at one end of the polypeptide for immobilization and/or for purification and/or for identification in a western blot. Optionally, tagged decoy ligands are also linked to a cellular localization signal for phenotypic comparison of pan-cellular and localized kinase modulation. A vector polynucleotide comprising a constitutive promotor, such as the CMV promotor, a decoy ligand coding sequence, an epitope tag coding sequence, and optionally a localization signal coding sequence is employed to express the decoy ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and immunoreagent-containing methods are performed as described in: Using Antibodies: A Laboratory Manual (Harlow and Lane Cold Spring Harbor Laboratory Press, 1999).

EXAMPLES

Example 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

Example 2

A transgene is constructed using a human cytomegalovirus (CMV) promoter to direct expression of a fusion protein comprising SEQ ID NO:46, SEQ ID NO:47, SEQ ID NO:74 (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein (GFP) by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a GSK3 ligand, a FLAG™ epitope, and a nuclear localization signal. The GSK3 ligand is a monomeric ligand, homopolymeric ligand or heteropolymeric ligand as described herein. Nucleotide sequences encoding a FLAG™ epitope are placed downstream of nucleotide sequences encoding the GSK3 ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

Example 4

Modulation of GSK3 cellular function by subcellularly localized GSK3 polyligand is illustrated. A transgene construct containing nucleic acids that encode a polyligand fusion protein, epitope, and nuclear localization signal is made. The expression unit contains nucleotides that encode SEQ ID NO:1 (POLYLIGAND), a c-Myc epitope (EPITOPE), and a nuclear localization signal (LOCALIZATION SIGNAL). This expression unit is subsequently subcloned into a vector between a CMV promoter and an SV40 polyadenylation signal (Generically depicted in FIG. 10A). The completed transgene-containing expression vector is then used to transfect cells. Inhibition of GSK3 activity is demonstrated by measuring phosphorylation of endogenous substrates against controls.

Example 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:112, a hemagluttinin epitope, and a nuclear localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 5 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

Test 3: Function is assessed by phenotypic observation or analysis against controls.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate GSK3 activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polynucleotide encoding a polypeptide comprising an amino acid sequence that is at least 98% identical to the amino acid sequence of SEQ ID NO:7 and wherein the polypeptide inhibits kinase activity of glycogen synthase kinase-3.

2. The isolated polynucleotide of claim 1, wherein said polypeptide is linked to one or more of a localization signal, an epitope tag and a reporter.

3. A vector comprising the polynucleotide of claim 1.

4. An isolated host cell comprising the polynucleotide of claim 1.

5. The polynucleotide of claim 1 further comprising a promoter.

6. The polynucleotide of claim 5, wherein the promoter is an inducible promoter.

7. The isolated polynucleotide of claim 1, wherein the polynucleotide comprises the nucleotide sequence of SEQ ID NO:9.

8. A method of inhibiting GSK3 in an isolated cell expressing GSK3 comprising transfecting an isolated host cell capable of expressing GSK3 with the vector of claim 3 and culturing the transfected host cell under conditions suitable to produce GSK3 and the polypeptide and wherein GSK3 activity in the cell is inhibited.

9. The isolated polynucleotide of claim 1, wherein said polypeptide is at least 99% identical to the amino acid sequence of SEQ ID NO:7.

10. The isolated polynucleotide of claim 1, wherein said polypeptide comprises the amino acid sequence of SEQ ID NO:7.

* * * * *

SEQUENCE LISTING

```
<160> NUMBER OF SEQ ID NOS: 127

<210> SEQ ID NO 1
<211> LENGTH: 32
<212> TYPE: PRT
<213> ORGANISM: artificial sequence
<220> FEATURE:
<223> OTHER INFORMATION: synthetic

<400> SEQUENCE: 1

Arg Arg Ala Ala Glu Glu Leu Asp Ser Arg Ala Gly Ala Pro Gln Leu
1               5                   10                  15

Arg Arg Ala Ala Glu Glu Leu Asp Ser Arg Ala Gly Ala Pro Gln Leu
            20                  25                  30

<210> SEQ ID NO 2
<211> LENGTH: 96
```

```
<212> TYPE: DNA
<213> ORGANISM: artificial sequence
<220> FEATURE:
<223> OTHER INFORMATION: synthetic

<400> SEQUENCE: 2
aggagagccg ctgaggaact ggacagcagg gccggagccc cccaactgag aagggctgcc      60
gaagaactcg attccagagc tggcgctcct caactc                               96

<210> SEQ ID NO 3
<211> LENGTH: 138
<212> TYPE: DNA
<213> ORGANISM: artificial sequence
<220> FEATURE:
<223> OTHER INFORMATION: synthetic

<400> SEQUENCE: 3
gctagcgcca ccatggccgg caggagagcc gctgaggaac tggacagcag ggccggagcc      60
ccccaactga aagggctgc cgaagaactc gattccagag ctggcgctcc tcaactcccc     120
gggggaggcg gaatcgat                                                  138

<210> SEQ ID NO 4
<211> LENGTH: 55
<212> TYPE: PRT
<213> ORGANISM: artificial sequence
<220> FEATURE:
<223> OTHER INFORMATION: synthetic

<400> SEQUENCE: 4

Asp Pro His Arg Leu Leu Gln Gln Leu Val Leu Ser Gly Asn Leu Ile
 1               5                  10                  15

Lys Glu Ala Val Arg Arg Leu His Gly Gly Ala Pro Ala Gly Gly Glu
            20                  25                  30

Val Arg Val Glu Pro Gln Lys Phe Ala Glu Glu Leu Ile His Arg Leu
        35                  40                  45

Glu Ala Val Gln Arg Thr Arg
    50                  55

<210> SEQ ID NO 5
<211> LENGTH: 165
<212> TYPE: DNA
<213> ORGANISM: artificial sequence
<220> FEATURE:
<223> OTHER INFORMATION: synthetic

<400> SEQUENCE: 5 gaccccaca ggctgctgca gcagctggtg ctgagcggca acctgatcaa ggaggccgtg       60
aggaggctgc acggcggcgc ccccgctgga ggcgaggtga gggtggagcc ccagaagttc     120
gccgaggagc tgatccacag gctggaggcc gtgcagagga ccagg                    165

<210> SEQ ID NO 6
<211> LENGTH: 192
<212> TYPE: DNA
<213> ORGANISM: artificial sequence
<220> FEATURE:
<223> OTHER INFORMATION: synthetic

<400> SEQUENCE: 6
gccggcgacc cccacaggct gctgcagcag ctggtgctga gcggcaacct gatcaaggag      60
gccgtgagga ggctgcacgg cggcgccccc gctggaggcg aggtgagggt ggagccccag     120
```

```
aagttcgccg aggagctgat ccacaggctg gaggccgtgc agaggaccag gcccgggggc    180
ggaggcatcg at                                                         192
```

<210> SEQ ID NO 7
<211> LENGTH: 71
<212> TYPE: PRT
<213> ORGANISM: artificial sequence
<220> FEATURE:
<223> OTHER INFORMATION: synthetic

<400> SEQUENCE: 7

```
Lys Arg Arg Glu Ile Leu Ala Arg Arg Pro Ser Tyr Arg Gly Gly Ala
1               5                   10                  15

Gly Gly Lys Glu Glu Pro Pro Ala Pro Pro Gln Ser Pro Gly Gly Gly
            20                  25                  30

Gly Gln Pro Glu Thr Arg Thr Gly Asp Asp Pro His Arg Leu Leu
        35                  40                  45

Gln Gln Leu Val Leu Ser Gly Asn Leu Ile Lys Glu Ala Val Arg Arg
    50                  55                  60

Leu His Ser Arg Arg Leu Gln
65                  70
```

<210> SEQ ID NO 8
<211> LENGTH: 213
<212> TYPE: DNA
<213> ORGANISM: artificial sequence
<220> FEATURE:
<223> OTHER INFORMATION: synthetic

<400> SEQUENCE: 8

```
aagaggaggg agatcctggc caggaggccc agctacaggg gcggcgctgg cggcaaggag    60
gagccccccg ccccccccca gagcccggc ggcggcggcc agcccgagac caggaccggc   120
gacgacgacc cccacaggct gctgcagcag ctggtgctga gcggcaacct gatcaaggag   180
gccgtgagga ggctgcacag caggaggctg cag                                213
```

<210> SEQ ID NO 9
<211> LENGTH: 240
<212> TYPE: DNA
<213> ORGANISM: artificial sequence
<220> FEATURE:
<223> OTHER INFORMATION: synthetic

<400> SEQUENCE: 9

```
gccggcaaga ggagggagat cctggccagg aggcccagct acaggggcgg cgctggcggc    60
aaggaggagc ccccgcccc cccccagagc cccggcggcg gcggccagcc cgagaccagg   120
accggcgacg acgaccccca caggctgctg cagcagctgg tgctgagcgg caacctgatc   180
aaggaggccg tgaggaggct gcacagcagg aggctgcagc ccgggggcgg aggcatcgat   240
```

<210> SEQ ID NO 10
<211> LENGTH: 93
<212> TYPE: PRT
<213> ORGANISM: artificial sequence
<220> FEATURE:
<223> OTHER INFORMATION: synthetic

<400> SEQUENCE: 10

```
Asn Tyr Ser Tyr Pro Tyr Ala Ala Pro Gln Thr Ala Pro Trp Gln Ala
1               5                   10                  15

Pro Cys Val Ser Pro Lys Thr Thr Asp Pro Glu Glu Gly Ala Ala Ala
```

20                  25                  30

Ala Asp Leu Pro Asp Ala Pro Gly Gln Ala Met Pro Pro Ala Arg Ser
                35                  40                  45

Lys Thr Pro Pro Pro Pro Gln Thr Ala Gln Thr Lys Arg Glu Val
            50                  55                  60

Gly Gly Ala Ala Pro Glu Pro Pro Ser Lys Ala Ser Pro Asp Ala Leu
 65                  70                  75                  80

Ala Pro Ala Thr Leu Arg Ser Leu Arg Lys Arg Leu
                85                  90

<210> SEQ ID NO 11
<211> LENGTH: 279
<212> TYPE: DNA
<213> ORGANISM: artificial sequence
<220> FEATURE:
<223> OTHER INFORMATION: synthetic

<400> SEQUENCE: 11
aactacagct acccctacgc cgcccccag accgccccct ggcaggcccc ctgcgtgagc    60
cccaagacca ccgaccccga ggagggcgcc gccgccgccg acctgcccga cgccccggc   120 caggccatgc cccccgccag gagcaagacc cccccccccc cccccagac cgcccagacc   180 aagagggagg tgggcggcgc cgccccgag cccccagca aggccagccc cgacgccctg    240
gcccccgcca ccctgaggag cctgaggaag aggaggctg                         279

<210> SEQ ID NO 12
<211> LENGTH: 312
<212> TYPE: DNA
<213> ORGANISM: artificial sequence
<220> FEATURE:
<223> OTHER INFORMATION: synthetic
<220> FEATURE:
<221> NAME/KEY: misc_feature
<222> LOCATION: (307)..(307)
<223> OTHER INFORMATION: n is a, c, g, or t

<400> SEQUENCE: 12
gccggcaact acagctaccc ctacgccgcc cccagaccg cccctggca ggcccctgc     60 gtgagcccca agaccaccga ccccgaggag gcgccgccg ccgccgacct gcccgacgcc   120
cccggccagg ccatgccccc cgccaggagc aagaccccc ccccccccc ccagaccgcc   180 cagaccaaga gggaggtggg cggcgccgcc cccgagcccc cagcaaggc cagccccgac   240 gccctggccc ccgccaccct gaggagcctg aggaagagga ggctgcccgg gggcggaggc   300
atcgatngth ss                                                     312

<210> SEQ ID NO 13
<211> LENGTH: 735
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (641)..(641)
<223> OTHER INFORMATION: Xaa can be any naturally occurring amino acid
<220> FEATURE:
<221> NAME/KEY: misc_feature
<222> LOCATION: (645)..(645)
<223> OTHER INFORMATION: Xaa can be any naturally occurring amino acid
<220> FEATURE:
<221> NAME/KEY: misc_feature
<222> LOCATION: (649)..(649)
<223> OTHER INFORMATION: Xaa can be any naturally occurring amino acid
<220> FEATURE:
<221> NAME/KEY: misc_feature
<222> LOCATION: (653)..(653)
<223> OTHER INFORMATION: Xaa can be any naturally occurring amino acid

<400> SEQUENCE: 13

```
Met Pro Leu Ser Arg Thr Leu Ser Val Ser Leu Pro Gly Leu Glu
1               5                   10                  15

Asp Trp Glu Asp Glu Phe Asp Leu Glu Asn Ser Val Leu Phe Glu Val
                20                  25                  30

Ala Trp Glu Val Ala Asn Lys Val Gly Gly Ile Tyr Thr Val Leu Gln
                35                  40                  45

Thr Lys Ala Lys Val Thr Gly Asp Glu Trp Gly Asp Asn Tyr Phe Leu
        50                  55                  60

Val Gly Pro Tyr Thr Glu Gln Gly Val Arg Thr Gln Val Glu Leu Leu
65                  70                  75                  80

Glu Pro Pro Thr Pro Ala Leu Lys Arg Thr Leu Asp Ser Met Asn Ser
                85                  90                  95

Lys Gly Cys Lys Val Tyr Phe Gly Arg Trp Leu Ile Glu Gly Gly Pro
                100                 105                 110

Leu Val Val Leu Leu Asp Val Gly Ala Ser Ala Trp Ala Leu Glu Arg
            115                 120                 125

Trp Lys Gly Glu Leu Trp Asp Thr Cys Asn Ile Gly Val Pro Trp Tyr
    130                 135                 140

Asp Arg Glu Ala Asn Asp Ala Val Leu Phe Gly Phe Leu Thr Thr Trp
145                 150                 155                 160

Phe Leu Gly Glu Phe Leu Ala Gln Asn Glu Lys Pro His Val Val
                165                 170                 175

Ala His Phe His Glu Trp Leu Ala Gly Ile Gly Leu Cys Leu Cys Arg
            180                 185                 190

Ala Arg Arg Leu Pro Val Ala Thr Ile Phe Thr Thr His Ala Thr Leu
            195                 200                 205

Leu Gly Arg Tyr Leu Cys Ala Gly Ala Val Asp Phe Tyr Asn Asn Leu
    210                 215                 220

Glu Asn Phe Asn Val Asp Lys Glu Ala Gly Glu Arg Gln Ile Tyr His
225                 230                 235                 240

Arg Tyr Cys Met Glu Arg Ala Ala Ala His Cys Ala His Val Phe Thr
                245                 250                 255

Thr Val Ser Gln Ile Thr Ala Ile Glu Ala Gln His Leu Leu Lys Arg
            260                 265                 270

Lys Pro Asp Ile Val Thr Pro Asn Gly Leu Asn Val Lys Lys Phe Ser
        275                 280                 285

Ala Met His Glu Phe Gln Asn Leu His Ala Gln Ser Lys Ala Arg Ile
    290                 295                 300

Gln Glu Phe Val Arg Gly His Phe Tyr Gly His Leu Asp Phe Asn Leu
305                 310                 315                 320

Asp Lys Thr Leu Tyr Phe Phe Ile Ala Gly Arg Tyr Glu Phe Ser Asn
                325                 330                 335

Lys Gly Ala Asp Val Phe Leu Glu Ala Leu Ala Arg Leu Asn Tyr Leu
            340                 345                 350

Leu Arg Val Asn Gly Ser Glu Gln Thr Val Val Ala Phe Phe Ile Met
        355                 360                 365

Pro Ala Arg Thr Asn Asn Phe Asn Val Glu Thr Leu Lys Gly Gln Ala
    370                 375                 380
```

```
Val Arg Lys Gln Leu Trp Asp Thr Ala Asn Thr Val Lys Glu Lys Phe
385                 390                 395                 400

Gly Arg Lys Leu Tyr Glu Ser Leu Leu Val Gly Ser Leu Pro Asp Met
            405                 410                 415

Asn Lys Met Leu Asp Lys Glu Asp Phe Thr Met Met Lys Arg Ala Ile
        420                 425                 430

Phe Ala Thr Gln Arg Gln Ser Phe Pro Pro Val Cys Thr His Asn Met
    435                 440                 445

Leu Asp Asp Ser Ser Asp Pro Ile Leu Thr Thr Ile Arg Arg Ile Gly
450                 455                 460

Leu Phe Asn Ser Ser Ala Asp Arg Val Lys Val Ile Phe His Pro Glu
465                 470                 475                 480

Phe Leu Ser Ser Thr Ser Pro Leu Leu Pro Val Asp Tyr Glu Glu Phe
                485                 490                 495

Val Arg Gly Cys His Leu Gly Val Phe Pro Ser Tyr Tyr Glu Pro Trp
                500                 505                 510

Gly Tyr Thr Pro Ala Glu Cys Thr Val Met Gly Ile Pro Ser Ile Ser
            515                 520                 525

Thr Asn Leu Ser Gly Phe Gly Cys Phe Met Glu Glu His Ile Ala Asp
        530                 535                 540

Pro Ser Ala Tyr Gly Ile Tyr Ile Leu Asp Arg Arg Phe Arg Ser Leu
545                 550                 555                 560

Asp Asp Ser Cys Ser Gln Leu Thr Ser Phe Leu Tyr Ser Phe Cys Gln
                565                 570                 575

Gln Ser Arg Arg Gln Arg Ile Ile Gln Arg Asn Arg Thr Glu Arg Leu
            580                 585                 590

Ser Asp Leu Leu Asp Trp Lys Tyr Leu Gly Arg Tyr Tyr Met Ser Ala
        595                 600                 605

Arg His Met Ala Leu Ala Lys Ala Phe Pro Asp His Phe Thr Tyr Glu
610                 615                 620

Pro His Glu Ala Asp Ala Thr Gln Gly Tyr Arg Tyr Pro Arg Pro Ala
625                 630                 635                 640

Xaa Val Pro Pro Xaa Pro Ser Leu Xaa Arg His Ser Xaa Pro His Gln
                645                 650                 655

Ser Glu Asp Glu Glu Pro Arg Asp Gly Leu Pro Glu Gly Asp Gly
            660                 665                 670

Glu Arg Tyr Asp Glu Asp Glu Ala Ala Lys Asp Arg Asn Ile
        675                 680                 685

Arg Ala Pro Glu Trp Pro Arg Arg Ala Ser Cys Thr Ser Ser Ser Gly
690                 695                 700

Gly Ser Lys Arg Ser Asn Ser Val Asp Thr Ser Ser Leu Ser Thr Pro
705                 710                 715                 720

Ser Glu Pro Leu Ser Pro Ala Ser Ser Leu Gly Glu Glu Arg Asn
                725                 730                 735

<210> SEQ ID NO 14
<211> LENGTH: 1139
<212> TYPE: PRT
<213> ORGANISM: Homo sapiens
<220> FEATURE:
<221> NAME/KEY: misc_feature
<222> LOCATION: (948)..(948)
<223> OTHER INFORMATION: Xaa can be any naturally occurring amino acid
<220> FEATURE:
<221> NAME/KEY: misc_feature
<222> LOCATION: (962)..(962)
<223> OTHER INFORMATION: Xaa can be any naturally occurring amino acid
```

```
<220> FEATURE:
<221> NAME/KEY: misc_feature
<222> LOCATION: (982)..(982)
<223> OTHER INFORMATION: Xaa can be any naturally occurring amino acid

<400> SEQUENCE: 14
```

Met Pro Ser Gly Gly Asp Gln Ser Pro Pro Pro Pro Pro Pro
1               5                   10

Ala Ala Ala Ala Ser Asp Glu Glu Glu Asp Asp Gly Glu Ala Glu
            20                  25                  30

Asp Ala Ala Pro Pro Ala Glu Ser Pro Thr Pro Gln Ile Gln Gln Arg
            35                  40                  45

Phe Asp Glu Leu Cys Ser Arg Leu Asn Met Asp Glu Ala Ala Arg Ala
50                  55                  60

Glu Ala Trp Asp Ser Tyr Arg Ser Met Ser Glu Ser Tyr Thr Leu Glu
65                  70                  75                  80

Gly Asn Asp Leu His Trp Leu Ala Cys Ala Leu Tyr Val Ala Cys Arg
                85                  90                  95

Lys Ser Val Pro Thr Val Ser Lys Gly Thr Val Glu Gly Asn Tyr Val
                100                 105                 110

Ser Leu Thr Arg Ile Leu Lys Cys Ser Glu Gln Ser Leu Ile Glu Phe
                115                 120                 125

Phe Asn Lys Met Lys Lys Trp Glu Asp Met Ala Asn Leu Pro Pro His
130                 135                 140

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
                165                 170                 175

Pro Gln Glu Glu Gln Pro Arg Gln Gln Arg Gly Arg Lys Gln Arg Arg
                180                 185                 190

Gln Pro Cys Thr Val Ser Glu Ile Phe His Phe Cys Trp Val Leu Phe
                195                 200                 205

Ile Tyr Ala Lys Gly Asn Phe Pro Met Ile Ser Asp Asp Leu Val Asn
                210                 215                 220

Ser Tyr His Leu Leu Leu Cys Ala Leu Asp Leu Val Tyr Gly Asn Ala
225                 230                 235                 240

Leu Gln Cys Ser Asn Arg Lys Glu Leu Val Asn Pro Asn Phe Lys Gly
                245                 250                 255

Leu Ser Glu Asp Phe His Ala Lys Asp Ser Lys Pro Ser Ser Asp Pro
                260                 265                 270

Pro Cys Ile Ile Glu Lys Leu Cys Ser Leu His Asp Gly Leu Val Leu
                275                 280                 285

Glu Ala Lys Gly Ile Lys Glu His Phe Trp Lys Pro Tyr Ile Arg Lys
                290                 295                 300

Leu Tyr Glu Lys Lys Leu Leu Lys Gly Lys Glu Glu Asn Leu Thr Gly
305                 310                 315                 320

Phe Leu Glu Pro Gly Asn Phe Gly Glu Ser Phe Lys Ala Ile Asn Lys
                325                 330                 335

Ala Tyr Glu Glu Tyr Val Leu Ser Val Gly Asn Leu Asp Glu Arg Ile
                340                 345                 350

Phe Leu Gly Glu Asp Ala Glu Glu Ile Gly Thr Leu Ser Arg Cys
                355                 360                 365

Leu Asn Ala Gly Ser Gly Thr Glu Thr Ala Glu Arg Val Gln Met Lys
370                 375                 380

```
Asn Ile Leu Gln Gln His Phe Asp Lys Ser Lys Ala Leu Arg Ile Ser
385                 390                 395                 400

Thr Pro Leu Thr Gly Val Arg Tyr Ile Lys Glu Asn Ser Pro Cys Val
            405                 410                 415

Thr Pro Val Ser Thr Ala Thr His Ser Leu Ser Arg Leu His Thr Met
        420                 425                 430

Leu Thr Gly Leu Arg Asn Ala Pro Ser Glu Lys Leu Glu Gln Ile Leu
    435                 440                 445

Arg Thr Cys Ser Arg Asp Pro Thr Gln Ala Ile Ala Asn Arg Leu Lys
450                 455                 460

Glu Met Phe Glu Ile Tyr Ser Gln His Phe Gln Pro Asp Glu Asp Phe
465                 470                 475                 480

Ser Asn Cys Ala Lys Glu Ile Ala Ser Lys His Phe Arg Phe Ala Glu
            485                 490                 495

Met Leu Tyr Tyr Lys Val Leu Glu Ser Val Ile Glu Gln Glu Gln Lys
        500                 505                 510

Arg Leu Gly Asp Met Asp Leu Ser Gly Ile Leu Glu Gln Asp Ala Phe
    515                 520                 525

His Arg Ser Leu Leu Ala Cys Cys Leu Glu Val Val Thr Phe Ser Tyr
530                 535                 540

Lys Pro Pro Gly Asn Phe Pro Phe Ile Thr Glu Ile Phe Asp Val Pro
545                 550                 555                 560

Leu Tyr His Phe Tyr Lys Val Ile Glu Val Phe Ile Arg Ala Glu Asp
            565                 570                 575

Gly Leu Cys Arg Glu Val Val Lys His Leu Asn Gln Ile Glu Glu Gln
        580                 585                 590

Ile Leu Asp His Leu Ala Trp Lys Pro Glu Ser Pro Leu Trp Glu Lys
    595                 600                 605

Ile Arg Asp Asn Glu Asn Arg Val Pro Thr Cys Glu Glu Val Met Pro
610                 615                 620

Pro Gln Asn Leu Glu Arg Ala Asp Glu Ile Cys Ile Ala Gly Ser Pro
625                 630                 635                 640

Leu Thr Pro Arg Arg Val Thr Glu Val Arg Ala Asp Thr Gly Gly Leu
            645                 650                 655

Gly Arg Ser Ile Thr Ser Pro Thr Thr Leu Tyr Asp Arg Tyr Ser Ser
        660                 665                 670

Pro Pro Ala Ser Thr Thr Arg Arg Leu Phe Val Glu Asn Asp Ser
    675                 680                 685

Pro Ser Asp Gly Gly Thr Pro Gly Arg Met Pro Pro Gln Pro Leu Val
690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
            725                 730                 735

Ala Asn Asn Gly Gln Thr Val Thr Ile Pro Val Gln Gly Ile Ala Asn
        740                 745                 750

Glu Asn Gly Gly Ile Thr Phe Phe Pro Val Gln Val Asn Val Gly Gly
    755                 760                 765

Gln Ala Gln Ala Val Thr Gly Ser Ile Gln Pro Leu Ser Ala Gln Ala
770                 775                 780

Leu Ala Gly Ser Leu Ser Ser Gln Gln Val Thr Gly Thr Thr Leu Gln
785                 790                 795                 800

Val Pro Gly Gln Val Ala Ile Gln Gln Ile Ser Pro Gly Gly Gln Gln
```

```
                    805                 810                 815
Gln Lys Gln Gly Gln Ser Val Thr Ser Ser Ser Asn Arg Pro Arg Lys
            820                 825                 830
Thr Ser Ser Leu Ser Leu Phe Phe Arg Lys Val Tyr His Leu Ala Ala
            835                 840                 845
Val Arg Leu Arg Asp Leu Cys Ala Lys Leu Asp Ile Ser Asp Glu Leu
            850                 855                 860
Arg Lys Lys Ile Trp Thr Cys Phe Glu Phe Ser Ile Ile Gln Cys Pro
865                 870                 875                 880
Glu Leu Met Met Asp Arg His Leu Asp Gln Leu Leu Met Cys Ala Ile
                885                 890                 895
Tyr Val Met Ala Lys Val Thr Lys Glu Asp Lys Ser Phe Gln Asn Ile
            900                 905                 910
Met Arg Cys Tyr Arg Thr Gln Pro Gln Ala Arg Ser Gln Val Tyr Arg
            915                 920                 925
Ser Val Leu Ile Lys Gly Lys Arg Lys Arg Arg Asn Ser Gly Ser Ser
            930                 935                 940
Asp Ser Arg Xaa His Gln Asn Ser Pro Thr Glu Leu Asn Lys Asp Arg
945                 950                 955                 960
Thr Xaa Arg Asp Ser Ser Pro Val Met Arg Ser Ser Thr Leu Pro
                965                 970                 975
Val Pro Gln Pro Ser Xaa Ala Pro Pro Thr Pro Thr Arg Leu Thr Gly
            980                 985                 990
Ala Asn Ser Asp Met Glu Glu Glu Glu Arg Gly Asp Leu Ile Gln Phe
            995                 1000                1005
Tyr Asn Asn Ile Tyr Ile Lys Gln Ile Lys Thr Phe Ala Met Lys
    1010                1015                1020
Tyr Ser Gln Ala Asn Met Asp Ala Pro Pro Leu Ser Pro Tyr Pro
    1025                1030                1035
Phe Val Arg Thr Gly Ser Pro Arg Arg Ile Gln Leu Ser Gln Asn
    1040                1045                1050
His Pro Val Tyr Ile Ser Pro His Lys Asn Glu Thr Met Leu Ser
    1055                1060                1065
Pro Arg Glu Lys Ile Phe Tyr Tyr Phe Ser Asn Ser Pro Ser Lys
    1070                1075                1080
Arg Leu Arg Glu Ile Asn Ser Met Ile Arg Thr Gly Glu Thr Pro
    1085                1090                1095
Thr Lys Lys Arg Gly Ile Leu Leu Glu Asp Gly Ser Glu Ser Pro
    1100                1105                1110
Ala Lys Arg Ile Cys Pro Glu Asn His Ser Ala Leu Leu Arg Arg
    1115                1120                1125
Leu Gln Asp Val Ala Asn Asp Arg Gly Ser His
    1130                1135

<210> SEQ ID NO 15
<211> LENGTH: 721
<212> TYPE: PRT
<213> ORGANISM: Homo sapiens
<220> FEATURE:
<221> NAME/KEY: misc_feature
<222> LOCATION: (540)..(540)
<223> OTHER INFORMATION: Xaa can be any naturally occurring amino acid

<400> SEQUENCE: 15

Met Ala Ala Pro Val Val Ala Pro Pro Gly Val Val Val Ser Arg Ala
1               5                   10                  15
```

```
Asn Lys Arg Ser Gly Ala Gly Pro Gly Gly Gly Gly Gly Ala
        20              25              30

Arg Gly Ala Glu Glu Pro Pro Pro Leu Gln Ala Val Leu Val
        35              40              45

Ala Asp Ser Phe Asp Arg Phe Phe Pro Ile Ser Lys Asp Gln Pro
50              55              60

Arg Val Leu Leu Pro Leu Ala Asn Val Ala Leu Ile Asp Tyr Thr Leu
65              70              75              80

Glu Phe Leu Thr Ala Thr Gly Val Gln Glu Thr Phe Val Phe Cys Cys
                85              90              95

Trp Lys Ala Ala Gln Ile Lys Glu His Leu Leu Lys Ser Lys Trp Cys
            100             105             110

Arg Pro Thr Ser Leu Asn Val Val Arg Ile Ile Thr Ser Glu Leu Tyr
            115             120             125

Arg Ser Leu Gly Asp Val Leu Arg Asp Val Asp Ala Lys Ala Leu Val
        130             135             140

Arg Ser Asp Phe Leu Leu Val Tyr Gly Asp Val Ile Ser Asn Ile Asn
145             150             155             160

Ile Thr Arg Ala Leu Glu Glu His Arg Leu Arg Lys Leu Glu Lys
            165             170             175

Asn Val Ser Val Met Thr Met Ile Phe Lys Glu Ser Pro Ser His
        180             185             190

Pro Thr Arg Cys His Glu Asp Asn Val Val Ala Val Asp Ser Thr
        195             200             205

Thr Asn Arg Val Leu His Phe Gln Lys Thr Gln Gly Leu Arg Arg Phe
        210             215             220

Ala Phe Pro Leu Ser Leu Phe Gln Gly Ser Ser Asp Gly Val Glu Val
225             230             235             240

Arg Tyr Asp Leu Leu Asp Cys His Ile Ser Ile Cys Ser Pro Gln Val
            245             250             255

Ala Gln Leu Phe Thr Asp Asn Phe Asp Tyr Gln Thr Arg Asp Asp Phe
        260             265             270

Val Arg Gly Leu Leu Val Asn Glu Glu Ile Leu Gly Asn Gln Ile His
        275             280             285

Met His Val Thr Ala Lys Glu Tyr Gly Ala Arg Val Ser Asn Leu His
290             295             300

Met Tyr Ser Ala Val Cys Ala Asp Val Ile Arg Arg Trp Val Tyr Pro
305             310             315             320

Leu Thr Pro Glu Ala Asn Phe Thr Asp Ser Thr Thr Gln Ser Cys Thr
            325             330             335

His Ser Arg His Asn Ile Tyr Arg Gly Pro Glu Val Ser Leu Gly His
            340             345             350

Gly Ser Ile Leu Glu Glu Asn Val Leu Leu Gly Ser Gly Thr Val Ile
        355             360             365

Gly Ser Asn Cys Phe Ile Thr Asn Ser Val Ile Gly Pro Gly Cys His
        370             375             380

Ile Gly Asp Asn Val Val Leu Asp Gln Thr Tyr Leu Trp Gln Gly Val
385             390             395             400

Arg Val Ala Ala Gly Ala Gln Ile His Gln Ser Leu Leu Cys Asp Asn
            405             410             415

Ala Glu Val Lys Glu Arg Val Thr Leu Lys Pro Arg Ser Val Leu Thr
            420             425             430
```

```
Ser Gln Val Val Gly Pro Asn Ile Thr Leu Pro Glu Gly Ser Val
            435                 440                 445

Ile Ser Leu His Pro Pro Asp Ala Glu Asp Glu Asp Asp Gly Glu
450                 455                 460

Phe Ser Asp Asp Ser Gly Ala Asp Gln Glu Lys Asp Lys Val Lys Met
465                 470                 475                 480

Lys Gly Tyr Asn Pro Ala Glu Val Gly Ala Gly Lys Gly Tyr Leu
                485                 490                 495

Trp Lys Ala Ala Gly Met Asn Met Glu Glu Glu Glu Leu Gln Gln
            500                 505                 510

Asn Leu Trp Gly Leu Lys Ile Asn Met Glu Glu Glu Ser Glu Ser Glu
            515                 520                 525

Ser Glu Gln Ser Met Asp Ser Glu Pro Asp Xaa Arg Gly Gly Ser
530                 535                 540

Pro Gln Met Asp Asp Ile Lys Val Phe Gln Asn Glu Val Leu Gly Thr
545                 550                 555                 560

Leu Gln Arg Gly Lys Glu Glu Asn Ile Ser Cys Asp Asn Leu Val Leu
                565                 570                 575

Glu Ile Asn Ser Leu Lys Tyr Ala Tyr Asn Val Ser Leu Lys Glu Val
            580                 585                 590

Met Gln Val Leu Ser His Val Val Leu Glu Phe Pro Leu Gln Gln Met
            595                 600                 605

Asp Ser Pro Leu Asp Ser Ser Arg Tyr Cys Ala Leu Leu Pro Leu
            610                 615                 620

Leu Lys Ala Trp Ser Pro Val Phe Arg Asn Tyr Ile Lys Arg Ala Ala
625                 630                 635                 640

Asp His Leu Glu Ala Leu Ala Ala Ile Glu Asp Phe Leu Glu His
            645                 650                 655

Glu Ala Leu Gly Ile Ser Met Ala Lys Val Leu Met Ala Phe Tyr Gln
            660                 665                 670

Leu Glu Ile Leu Ala Glu Glu Thr Ile Leu Ser Trp Phe Ser Gln Arg
            675                 680                 685

Asp Thr Thr Asp Lys Gly Gln Gln Leu Arg Lys Asn Gln Gln Leu Gln
690                 695                 700

Arg Phe Ile Gln Trp Leu Lys Glu Ala Glu Glu Ser Ser Glu Asp
705                 710                 715                 720

Asp

<210> SEQ ID NO 16
<211> LENGTH: 1101
<212> TYPE: PRT
<213> ORGANISM: Homo sapiens
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid

<400> SEQUENCE: 16

Met Ser Ala Lys Ala Ile Ser Glu Gln Thr Gly Lys Glu Leu Leu Tyr
1               5                   10                  15
```

-continued

```
Lys Phe Ile Cys Thr Thr Ser Ala Ile Gln Asn Arg Phe Lys Tyr Ala
             20                  25                  30
Arg Val Thr Pro Asp Thr Asp Trp Ala Arg Leu Leu Gln Asp His Pro
             35                  40                  45
Trp Leu Leu Ser Gln Asn Leu Val Val Lys Pro Asp Gln Leu Ile Lys
         50                  55                  60
Arg Arg Gly Lys Leu Gly Leu Val Gly Val Asn Leu Thr Leu Asp Gly
65                  70                  75                  80
Val Lys Ser Trp Leu Lys Pro Arg Leu Gly Gln Glu Ala Thr Val Gly
                 85                  90                  95
Lys Ala Thr Gly Phe Leu Lys Asn Phe Leu Ile Glu Pro Phe Val Pro
                100                 105                 110
His Ser Gln Ala Glu Glu Phe Tyr Val Cys Ile Tyr Ala Thr Arg Glu
            115                 120                 125
Gly Asp Tyr Val Leu Phe His His Glu Gly Gly Val Asp Val Gly Asp
        130                 135                 140
Val Asp Ala Lys Ala Gln Lys Leu Leu Val Gly Val Asp Glu Lys Leu
145                 150                 155                 160
Asn Pro Glu Asp Ile Lys Lys His Leu Leu Val His Ala Pro Glu Asp
                165                 170                 175
Lys Lys Glu Ile Leu Ala Ser Phe Ile Ser Gly Leu Phe Asn Phe Tyr
                180                 185                 190
Glu Asp Leu Tyr Phe Thr Tyr Leu Glu Ile Asn Pro Leu Val Val Thr
            195                 200                 205
Lys Asp Gly Val Tyr Val Leu Asp Leu Ala Ala Lys Val Asp Ala Thr
        210                 215                 220
Ala Asp Tyr Ile Cys Lys Val Lys Trp Gly Asp Ile Glu Phe Pro Pro
225                 230                 235                 240
Pro Phe Gly Arg Glu Ala Tyr Pro Glu Glu Ala Tyr Ile Ala Asp Leu
                245                 250                 255
Asp Ala Lys Ser Gly Ala Ser Leu Lys Leu Thr Leu Leu Asn Pro Lys
                260                 265                 270
Gly Arg Ile Trp Thr Met Val Ala Gly Gly Ala Ser Val Val Tyr
            275                 280                 285
Ser Asp Thr Ile Cys Asp Leu Gly Gly Val Asn Glu Leu Ala Asn Tyr
        290                 295                 300
Gly Glu Tyr Ser Gly Ala Pro Ser Glu Gln Gln Thr Tyr Asp Tyr Ala
305                 310                 315                 320
Lys Thr Ile Leu Ser Leu Met Thr Arg Glu Lys His Pro Asp Gly Lys
                325                 330                 335
Ile Leu Ile Ile Gly Gly Ser Ile Ala Asn Phe Thr Asn Val Ala Ala
                340                 345                 350
Thr Phe Lys Gly Ile Val Arg Ala Ile Arg Asp Tyr Gln Gly Pro Leu
            355                 360                 365
Lys Glu His Glu Val Thr Ile Phe Val Arg Arg Gly Gly Pro Asn Tyr
        370                 375                 380
Gln Glu Gly Leu Arg Val Met Gly Glu Val Gly Lys Thr Thr Gly Ile
385                 390                 395                 400
Pro Ile His Val Phe Gly Thr Glu Thr His Met Thr Ala Ile Val Gly
                405                 410                 415
Met Ala Leu Gly His Arg Pro Ile Pro Asn Gln Pro Pro Thr Ala Ala
                420                 425                 430
His Thr Ala Asn Phe Leu Leu Asn Ala Ser Gly Ser Thr Ser Xaa Pro
```

```
                435                 440                 445
Ala Pro Xaa Arg Thr Ala Xaa Phe Ser Glu Ser Arg Ala Asp Glu Val
450                 455                 460
Ala Pro Ala Lys Lys Ala Lys Pro Ala Met Pro Gln Asp Ser Val Pro
465                 470                 475                 480
Ser Pro Arg Ser Leu Gln Gly Lys Ser Thr Thr Leu Phe Ser Arg His
                485                 490                 495
Thr Lys Ala Ile Val Trp Gly Met Gln Thr Arg Ala Val Gln Gly Met
                500                 505                 510
Leu Asp Phe Asp Tyr Val Cys Ser Arg Asp Glu Pro Ser Val Ala Ala
                515                 520                 525
Met Val Tyr Pro Phe Thr Gly Asp His Lys Gln Lys Phe Tyr Trp Gly
530                 535                 540
His Lys Glu Ile Leu Ile Pro Val Phe Lys Asn Met Ala Asp Ala Met
545                 550                 555                 560
Arg Lys His Pro Glu Val Asp Val Leu Ile Asn Phe Ala Ser Leu Arg
                565                 570                 575
Ser Ala Tyr Asp Ser Thr Met Glu Thr Met Asn Tyr Ala Gln Ile Arg
                580                 585                 590
Thr Ile Ala Ile Ile Ala Glu Gly Ile Pro Glu Ala Leu Thr Arg Lys
                595                 600                 605
Leu Ile Lys Lys Ala Asp Gln Lys Gly Val Thr Ile Ile Gly Pro Ala
610                 615                 620
Thr Val Gly Gly Ile Lys Pro Gly Cys Phe Lys Ile Gly Asn Thr Gly
625                 630                 635                 640
Gly Met Leu Asp Asn Ile Leu Ala Ser Lys Leu Tyr Arg Pro Gly Ser
                645                 650                 655
Val Ala Tyr Val Ser Arg Ser Gly Gly Met Ser Asn Glu Leu Asn Asn
                660                 665                 670
Ile Ile Ser Arg Thr Thr Asp Gly Val Tyr Glu Gly Val Ala Ile Gly
                675                 680                 685
Gly Asp Arg Tyr Pro Gly Ser Thr Phe Met Asp His Val Leu Arg Tyr
                690                 695                 700
Gln Asp Thr Pro Gly Val Lys Met Ile Val Val Leu Gly Glu Ile Gly
705                 710                 715                 720
Gly Thr Glu Glu Tyr Lys Ile Cys Arg Gly Ile Lys Glu Gly Arg Leu
                725                 730                 735
Thr Lys Pro Ile Val Cys Trp Cys Ile Gly Thr Cys Ala Thr Met Phe
                740                 745                 750
Ser Ser Glu Val Gln Phe Gly His Ala Gly Ala Cys Ala Asn Gln Ala
                755                 760                 765
Ser Glu Thr Ala Val Ala Lys Asn Gln Ala Leu Lys Glu Ala Gly Val
                770                 775                 780
Phe Val Pro Arg Ser Phe Asp Glu Leu Gly Glu Ile Ile Gln Ser Val
785                 790                 795                 800
Tyr Glu Asp Leu Val Ala Asn Gly Val Ile Val Pro Ala Gln Glu Val
                805                 810                 815
Pro Pro Pro Thr Val Pro Met Asp Tyr Ser Trp Ala Arg Glu Leu Gly
                820                 825                 830
Leu Ile Arg Lys Pro Ala Ser Phe Met Thr Ser Ile Cys Asp Glu Arg
                835                 840                 845
Gly Gln Glu Leu Ile Tyr Ala Gly Met Pro Ile Thr Glu Val Phe Lys
                850                 855                 860
```

-continued

```
Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
                885                 890                 895

Thr Ala Asp His Gly Pro Ala Val Ser Gly Ala His Asn Thr Ile Ile
            900                 905                 910

Cys Ala Arg Ala Gly Lys Asp Leu Val Ser Ser Leu Thr Ser Gly Leu
        915                 920                 925

Leu Thr Ile Gly Asp Arg Phe Gly Gly Ala Leu Asp Ala Ala Ala Lys
    930                 935                 940

Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
                965                 970                 975

Val Lys Ser Ile Asn Asn Pro Asp Met Arg Val Gln Ile Leu Lys Asp
            980                 985                 990

Tyr Val Arg Gln His Phe Pro Ala  Thr Pro Leu Leu Asp  Tyr Ala Leu
        995                 1000                1005

Glu Val Glu Lys Ile Thr Thr  Ser Lys Lys Pro Asn  Leu Ile Leu
    1010                1015                1020

Asn Val Asp Gly Leu Ile Gly  Val Ala Phe Val Asp  Met Leu Arg
    1025                1030                1035

Asn Cys Gly Ser Phe Thr Arg  Glu Glu Ala Asp Glu  Tyr Ile Asp
    1040                1045                1050

Ile Gly Ala Leu Asn Gly Ile  Phe Val Leu Gly Arg  Ser Met Gly
    1055                1060                1065

Phe Ile Gly His Tyr Leu Asp  Gln Lys Arg Leu Lys  Gln Gly Leu
    1070                1075                1080

Tyr Arg His Pro Trp Asp Asp  Ile Ser Tyr Val Leu  Pro Glu His
    1085                1090                1095

Met Ser Met
    1100

<210> SEQ ID NO 17
<211> LENGTH: 862
<212> TYPE: PRT
<213> ORGANISM: Homo sapiens
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid

<400> SEQUENCE: 17

Met Asn Ile Gln Glu Gln Gly Phe Pro Leu Asp Leu Gly Ala Ser Phe
1               5                   10                  15

Thr Glu Asp Ala Pro Arg Pro Pro Val Pro Gly Glu Glu Gly Glu Leu
            20                  25                  30

Val Ser Thr Asp Pro Arg Pro Ala Ser Tyr Ser Phe Cys Ser Gly Lys
        35                  40                  45

Gly Val Gly Ile Lys Gly Glu Thr Ser Thr Ala Thr Pro Arg Arg Ser
    50                  55                  60

Asp Leu Asp Leu Gly Tyr Glu Pro Glu Gly Ser Ala Ser Pro Thr Pro
65                  70                  75                  80
```

```
Pro Tyr Leu Lys Trp Ala Glu Ser Leu His Ser Leu Leu Asp Asp Gln
            85                  90                  95

Asp Gly Ile Ser Leu Phe Arg Thr Phe Leu Lys Gln Glu Gly Cys Ala
                100                 105                 110

Asp Leu Leu Asp Phe Trp Phe Ala Cys Thr Gly Phe Arg Lys Leu Glu
            115                 120                 125

Pro Cys Asp Ser Asn Glu Glu Lys Arg Leu Lys Leu Ala Arg Ala Ile
        130                 135                 140

Tyr Arg Lys Tyr Ile Leu Asp Asn Asn Gly Ile Val Ser Arg Gln Thr
145                 150                 155                 160

Lys Pro Ala Thr Lys Ser Phe Ile Lys Gly Cys Ile Met Lys Gln Leu
                165                 170                 175

Ile Asp Pro Ala Met Phe Asp Gln Ala Gln Thr Glu Ile Gln Ala Thr
            180                 185                 190

Met Glu Glu Asn Thr Tyr Pro Ser Phe Leu Lys Ser Asp Ile Tyr Leu
        195                 200                 205

Glu Tyr Thr Arg Thr Gly Ser Glu Ser Pro Lys Val Cys Ser Asp Gln
210                 215                 220

Ser Ser Gly Ser Gly Thr Gly Lys Gly Ile Ser Gly Tyr Leu Pro Thr
225                 230                 235                 240

Leu Asn Glu Asp Glu Glu Trp Lys Cys Asp Gln Asp Met Asp Glu Asp
                245                 250                 255

Asp Gly Arg Asp Ala Ala Pro Pro Gly Arg Leu Pro Gln Lys Leu Leu
            260                 265                 270

Leu Glu Thr Ala Ala Pro Arg Val Ser Ser Arg Arg Tyr Ser Glu
                275                 280                 285

Gly Arg Glu Phe Arg Tyr Gly Ser Trp Arg Glu Pro Val Asn Pro Tyr
        290                 295                 300

Tyr Val Asn Ala Gly Tyr Ala Leu Ala Pro Ala Thr Xaa Ala Asn Asp
305                 310                 315                 320

Xaa Glu Gln Gln Ser Leu Ser Ser Asp Ala Asp Thr Leu Ser Leu Thr
                325                 330                 335

Asp Ser Ser Val Asp Gly Ile Pro Pro Tyr Arg Ile Arg Lys Gln His
            340                 345                 350

Arg Arg Glu Met Gln Glu Ser Val Gln Val Asn Gly Arg Val Pro Leu
        355                 360                 365

Pro His Ile Pro Arg Thr Tyr Arg Val Pro Lys Glu Val Arg Val Glu
    370                 375                 380

Pro Gln Lys Phe Ala Glu Glu Leu Ile His Arg Leu Glu Ala Val Gln
385                 390                 395                 400

Arg Thr Arg Glu Ala Glu Glu Lys Leu Glu Glu Arg Leu Lys Arg Val
                405                 410                 415

Arg Met Glu Glu Glu Gly Glu Asp Gly Asp Pro Ser Ser Gly Pro Pro
            420                 425                 430

Gly Pro Cys His Lys Leu Pro Pro Ala Pro Ala Trp His His Phe Pro
        435                 440                 445

Pro Arg Cys Val Asp Met Gly Cys Ala Gly Leu Arg Asp Ala His Glu
    450                 455                 460

Glu Asn Pro Glu Ser Ile Leu Asp Glu His Val Gln Arg Val Leu Arg
465                 470                 475                 480

Thr Pro Gly Arg Gln Ser Pro Gly Pro Gly His Arg Ser Pro Asp Ser
                485                 490                 495
```

```
Gly His Val Ala Lys Met Pro Val Ala Leu Gly Gly Ala Ala Ser Gly
            500                 505                 510

His Gly Lys His Val Pro Lys Ser Gly Ala Lys Leu Asp Ala Ala Gly
        515                 520                 525

Leu His His Arg His Val His His Val His His Ser Thr Ala
    530                 535                 540

Arg Pro Lys Glu Gln Val Glu Ala Glu Ala Thr Arg Arg Ala Gln Ser
545                 550                 555                 560

Ser Phe Ala Trp Gly Leu Glu Pro His Ser His Gly Ala Arg Ser Arg
                565                 570                 575

Gly Tyr Ser Glu Ser Val Gly Ala Ala Pro Asn Ala Ser Asp Gly Leu
                580                 585                 590

Ala His Ser Gly Lys Val Gly Val Ala Cys Lys Arg Asn Ala Lys Lys
            595                 600                 605

Ala Glu Ser Gly Lys Ser Ala Ser Thr Glu Val Pro Gly Ala Ser Glu
        610                 615                 620

Asp Ala Glu Lys Asn Gln Lys Ile Met Gln Trp Ile Ile Glu Gly Glu
625                 630                 635                 640

Lys Glu Ile Ser Arg His Arg Arg Thr Gly His Gly Ser Ser Gly Thr
                645                 650                 655

Arg Lys Pro Gln Pro His Glu Asn Ser Arg Pro Leu Ser Leu Glu His
                660                 665                 670

Pro Trp Ala Gly Pro Gln Leu Arg Thr Ser Val Gln Pro Ser His Leu
            675                 680                 685

Phe Ile Gln Asp Pro Thr Met Pro Pro His Pro Ala Pro Asn Pro Leu
690                 695                 700

Thr Gln Leu Glu Glu Ala Arg Arg Leu Glu Glu Glu Lys Arg
705                 710                 715                 720

Ala Ser Arg Ala Pro Ser Lys Gln Arg Tyr Val Gln Glu Val Met Arg
                725                 730                 735

Arg Gly Arg Ala Cys Val Arg Pro Ala Cys Ala Pro Val Leu His Val
            740                 745                 750

Val Pro Ala Val Ser Asp Met Glu Leu Ser Glu Thr Glu Thr Arg Ser
        755                 760                 765

Gln Arg Lys Val Gly Gly Ser Ala Gln Pro Cys Asp Ser Ile Val
770                 775                 780

Val Ala Tyr Tyr Phe Cys Gly Glu Pro Ile Pro Tyr Arg Thr Leu Val
785                 790                 795                 800

Arg Gly Arg Ala Val Thr Leu Gly Gln Phe Lys Glu Leu Leu Thr Lys
                805                 810                 815

Lys Gly Ser Tyr Arg Tyr Tyr Phe Lys Lys Val Ser Asp Glu Phe Asp
                820                 825                 830

Cys Gly Val Val Phe Glu Glu Val Arg Glu Asp Glu Ala Val Leu Pro
            835                 840                 845

Val Phe Glu Glu Lys Ile Ile Gly Lys Val Glu Lys Val Asp
        850                 855                 860

<210> SEQ ID NO 18
<211> LENGTH: 781
<212> TYPE: PRT
<213> ORGANISM: Homo sapiens
<220> FEATURE:
<221> NAME/KEY: misc_feature
<222> LOCATION: (33)..(33)
<223> OTHER INFORMATION: Xaa can be any naturally occurring amino acid
<220> FEATURE:
```

-continued

```
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 18

Met Ala Thr Gln Ala Asp Leu Met Glu Leu Asp Met Ala Met Glu Pro
1               5                   10                  15

Asp Arg Lys Ala Ala Val Ser His Trp Gln Gln Ser Tyr Leu Asp
            20                  25                  30

Xaa Gly Ile His Xaa Gly Ala Thr Xaa Thr Ala Pro Ser Leu Ser Gly
                35                  40                  45

Lys Gly Asn Pro Glu Glu Asp Val Asp Thr Ser Gln Val Leu Tyr
            50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
        130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
            245                 250                 255

Thr Thr Leu His Asn Leu Leu Leu His Gln Glu Gly Ala Lys Met Ala
        260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
        340                 345                 350

Asn Lys Pro Ala Ile Val Glu Ala Gly Gly Met Gln Ala Leu Gly Leu
        355                 360                 365
```

```
His Leu Thr Asp Pro Ser Gln Arg Leu Val Gln Asn Cys Leu Trp Thr
    370                 375                 380
Leu Arg Asn Leu Ser Asp Ala Ala Thr Lys Gln Glu Gly Met Glu Gly
385                 390                 395                 400
Leu Leu Gly Thr Leu Val Gln Leu Leu Gly Ser Asp Asp Ile Asn Val
            405                 410                 415
Val Thr Cys Ala Ala Gly Ile Leu Ser Asn Leu Thr Cys Asn Asn Tyr
        420                 425                 430
Lys Asn Lys Met Met Val Cys Gln Val Gly Gly Ile Glu Ala Leu Val
            435                 440                 445
Arg Thr Val Leu Arg Ala Gly Asp Arg Glu Asp Ile Thr Glu Pro Ala
450                 455                 460
Ile Cys Ala Leu Arg His Leu Thr Ser Arg His Gln Glu Ala Glu Met
465                 470                 475                 480
Ala Gln Asn Ala Val Arg Leu His Tyr Gly Leu Pro Val Val Val Lys
                485                 490                 495
Leu Leu His Pro Pro Ser His Trp Pro Leu Ile Lys Ala Thr Val Gly
            500                 505                 510
Leu Ile Arg Asn Leu Ala Leu Cys Pro Ala Asn His Ala Pro Leu Arg
        515                 520                 525
Glu Gln Gly Ala Ile Pro Arg Leu Val Gln Leu Leu Val Arg Ala His
    530                 535                 540
Gln Asp Thr Gln Arg Arg Thr Ser Met Gly Gly Thr Gln Gln Gln Phe
545                 550                 555                 560
Val Glu Gly Val Arg Met Glu Glu Ile Val Glu Gly Cys Thr Gly Ala
                565                 570                 575
Leu His Ile Leu Ala Arg Asp Val His Asn Arg Ile Val Ile Arg Gly
            580                 585                 590
Leu Asn Thr Ile Pro Leu Phe Val Gln Leu Leu Tyr Ser Pro Ile Glu
        595                 600                 605
Asn Ile Gln Arg Val Ala Ala Gly Val Leu Cys Glu Leu Ala Gln Asp
    610                 615                 620
Lys Glu Ala Ala Glu Ala Ile Glu Ala Glu Gly Ala Thr Ala Pro Leu
625                 630                 635                 640
Thr Glu Leu Leu His Ser Arg Asn Glu Gly Val Ala Thr Tyr Ala Ala
            645                 650                 655
Ala Val Leu Phe Arg Met Ser Glu Asp Lys Pro Gln Asp Tyr Lys Lys
        660                 665                 670
Arg Leu Ser Val Glu Leu Thr Ser Ser Leu Phe Arg Thr Glu Pro Met
    675                 680                 685
Ala Trp Asn Glu Thr Ala Asp Leu Gly Leu Asp Ile Gly Ala Gln Gly
690                 695                 700
Glu Pro Leu Gly Tyr Arg Gln Asp Pro Ser Tyr Arg Ser Phe His
705                 710                 715                 720
Ser Gly Gly Tyr Gly Gln Asp Ala Leu Gly Met Asp Pro Met Met Glu
                725                 730                 735
His Glu Met Gly Gly His His Pro Gly Ala Asp Tyr Pro Val Asp Gly
            740                 745                 750
Leu Pro Asp Leu Gly His Ala Gln Asp Leu Met Asp Gly Leu Pro Pro
        755                 760                 765
Gly Asp Ser Asn Gln Leu Ala Trp Phe Asp Thr Asp Leu
770                 775                 780
```

-continued

```
<210> SEQ ID NO 19
<211> LENGTH: 2843
<212> TYPE: PRT
<213> ORGANISM: Homo sapiens
<220> FEATURE:
<221> NAME/KEY: misc_feature
<222> LOCATION: (1340)..(1340)
<223> OTHER INFORMATION: Xaa can be any naturally occurring amino acid
<220> FEATURE:
<221> NAME/KEY: misc_feature
<222> LOCATION: (1356)..(1356)
<223> OTHER INFORMATION: Xaa can be any naturally occurring amino acid
<220> FEATURE:
<221> NAME/KEY: misc_feature
<222> LOCATION: (1391)..(1391)
<223> OTHER INFORMATION: Xaa can be any naturally occurring amino acid
<220> FEATURE:
<221> NAME/KEY: misc_feature
<222> LOCATION: (1400)..(1400)
<223> OTHER INFORMATION: Xaa can be any naturally occurring amino acid
<220> FEATURE:
<221> NAME/KEY: misc_feature
<222> LOCATION: (1407)..(1407)
<223> OTHER INFORMATION: Xaa can be any naturally occurring amino acid
<220> FEATURE:
<221> NAME/KEY: misc_feature
<222> LOCATION: (1411)..(1411)
<223> OTHER INFORMATION: Xaa can be any naturally occurring amino acid
<220> FEATURE:
<221> NAME/KEY: misc_feature
<222> LOCATION: (1415)..(1415)
<223> OTHER INFORMATION: Xaa can be any naturally occurring amino acid
<220> FEATURE:
<221> NAME/KEY: misc_feature
<222> LOCATION: (1426)..(1426)
<223> OTHER INFORMATION: Xaa can be any naturally occurring amino acid
<220> FEATURE:
<221> NAME/KEY: misc_feature
<222> LOCATION: (1430)..(1430)
<223> OTHER INFORMATION: Xaa can be any naturally occurring amino acid
<220> FEATURE:
<221> NAME/KEY: misc_feature
<222> LOCATION: (1434)..(1434)
<223> OTHER INFORMATION: Xaa can be any naturally occurring amino acid

<400> SEQUENCE: 19

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
                20                  25                  30

His Leu Thr Lys Leu Glu Thr Glu Ala Ser Asn Met Lys Glu Val Leu
            35                  40                  45

Lys Gln Leu Gln Gly Ser Ile Glu Asp Glu Ala Met Ala Ser Ser Gly
        50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175
```

```
Asn Phe Ser Leu Gln Thr Asp Met Thr Arg Arg Gln Leu Glu Tyr Glu
                180                 185                 190

Ala Arg Gln Ile Arg Val Ala Met Glu Glu Gln Leu Gly Thr Cys Gln
            195                 200                 205

Asp Met Glu Lys Arg Ala Gln Arg Ile Ala Arg Ile Gln Gln Ile
        210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590
```

```
Trp Asn Leu Ser Ala His Cys Thr Glu Asn Lys Ala Asp Ile Cys Ala
            595                 600                 605
Val Asp Gly Ala Leu Ala Phe Leu Val Gly Thr Leu Thr Tyr Arg Ser
    610                 615                 620
Gln Thr Asn Thr Leu Ala Ile Ile Glu Ser Gly Gly Gly Ile Leu Arg
625                 630                 635                 640
Asn Val Ser Ser Leu Ile Ala Thr Asn Glu Asp His Arg Gln Ile Leu
                645                 650                 655
Arg Glu Asn Asn Cys Leu Gln Thr Leu Leu Gln His Leu Lys Ser His
            660                 665                 670
Ser Leu Thr Ile Val Ser Asn Ala Cys Gly Thr Leu Trp Asn Leu Ser
        675                 680                 685
Ala Arg Asn Pro Lys Asp Gln Glu Ala Leu Trp Asp Met Gly Ala Val
    690                 695                 700
Ser Met Leu Lys Asn Leu Ile His Ser Lys His Lys Met Ile Ala Met
705                 710                 715                 720
Gly Ser Ala Ala Leu Arg Asn Leu Met Ala Asn Arg Pro Ala Lys
                725                 730                 735
Tyr Lys Asp Ala Asn Ile Met Ser Pro Gly Ser Ser Leu Pro Ser Leu
            740                 745                 750
His Val Arg Lys Gln Lys Ala Leu Glu Ala Glu Leu Asp Ala Gln His
        755                 760                 765
Leu Ser Glu Thr Phe Asp Asn Ile Asp Asn Leu Ser Pro Lys Ala Ser
    770                 775                 780
His Arg Ser Lys Gln Arg His Lys Gln Ser Leu Tyr Gly Asp Tyr Val
785                 790                 795                 800
Phe Asp Thr Asn Arg His Asp Asp Asn Arg Ser Asp Asn Phe Asn Thr
                805                 810                 815
Gly Asn Met Thr Val Leu Ser Pro Tyr Leu Asn Thr Thr Val Leu Pro
            820                 825                 830
Ser Ser Ser Ser Ser Arg Gly Ser Leu Asp Ser Ser Arg Ser Glu Lys
        835                 840                 845
Asp Arg Ser Leu Glu Arg Glu Arg Gly Ile Gly Leu Gly Asn Tyr His
    850                 855                 860
Pro Ala Thr Glu Asn Pro Gly Thr Ser Ser Lys Arg Gly Leu Gln Ile
865                 870                 875                 880
Ser Thr Thr Ala Ala Gln Ile Ala Lys Val Met Glu Glu Val Ser Ala
                885                 890                 895
Ile His Thr Ser Gln Glu Asp Arg Ser Ser Gly Ser Thr Thr Glu Leu
            900                 905                 910
His Cys Val Thr Asp Glu Arg Asn Ala Leu Arg Arg Ser Ser Ala Ala
        915                 920                 925
His Thr His Ser Asn Thr Tyr Asn Phe Thr Lys Ser Glu Asn Ser Asn
    930                 935                 940
Arg Thr Cys Ser Met Pro Tyr Ala Lys Leu Glu Tyr Lys Arg Ser Ser
945                 950                 955                 960
Asn Asp Ser Leu Asn Ser Val Ser Ser Asp Gly Tyr Gly Lys Arg
                965                 970                 975
Gly Gln Met Lys Pro Ser Ile Glu Ser Tyr Ser Glu Asp Asp Glu Ser
            980                 985                 990
Lys Phe Cys Ser Tyr Gly Gln Tyr  Pro Ala Asp Leu Ala  His Lys Ile
        995                 1000                1005
His Ser  Ala Asn His Met Asp  Asp Asn Asp Gly Glu  Leu Asp Thr
```

```
              1010                1015                1020

Pro Ile Asn Tyr Ser Leu Lys Tyr Ser Asp Glu Gln Leu Asn Ser
    1025                1030                1035

Gly Arg Gln Ser Pro Ser Gln Asn Glu Arg Trp Ala Arg Pro Lys
    1040                1045                1050

His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110

Arg Val Gly Ser Asn His Gly Ile Asn Gln Asn Val Ser Gln Ser
    1115                1120                1125

Leu Cys Gln Glu Asp Asp Tyr Glu Asp Asp Lys Pro Thr Asn Tyr
    1130                1135                1140

Ser Glu Arg Tyr Ser Glu Glu Glu Gln His Glu Glu Glu Glu Arg
    1145                1150                1155

Pro Thr Asn Tyr Ser Ile Lys Tyr Asn Glu Glu Lys Arg His Val
    1160                1165                1170

Asp Gln Pro Ile Asp Tyr Ser Leu Lys Tyr Ala Thr Asp Ile Pro
    1175                1180                1185

Ser Ser Gln Lys Gln Ser Phe Ser Phe Ser Lys Ser Ser Ser Gly
    1190                1195                1200

Gln Ser Ser Lys Thr Glu His Met Ser Ser Ser Glu Asn Thr
    1205                1210                1215

Ser Thr Pro Ser Ser Asn Ala Lys Arg Gln Asn Gln Leu His Pro
    1220                1225                1230

Ser Ser Ala Gln Ser Arg Ser Gly Gln Pro Gln Lys Ala Ala Thr
    1235                1240                1245

Cys Lys Val Ser Ser Ile Asn Gln Glu Thr Ile Gln Thr Tyr Cys
    1250                1255                1260

Val Glu Asp Thr Pro Ile Cys Phe Ser Arg Cys Ser Ser Leu Ser
    1265                1270                1275

Ser Leu Ser Ser Ala Glu Asp Glu Ile Gly Cys Asn Gln Thr Thr
    1280                1285                1290

Gln Glu Ala Asp Ser Ala Asn Thr Leu Gln Ile Ala Glu Ile Lys
    1295                1300                1305

Glu Lys Ile Gly Thr Arg Ser Ala Glu Asp Pro Val Ser Glu Val
    1310                1315                1320

Pro Ala Val Ser Gln His Pro Arg Thr Lys Ser Ser Arg Leu Gln
    1325                1330                1335

Gly Xaa Ser Leu Ser Ser Glu Ser Ala Arg His Lys Ala Val Glu
    1340                1345                1350

Phe Ser Xaa Gly Ala Lys Ser Pro Ser Lys Ser Gly Ala Gln Thr
    1355                1360                1365

Pro Lys Ser Pro Pro Glu His Tyr Val Gln Glu Thr Pro Leu Met
    1370                1375                1380

Phe Ser Arg Cys Thr Ser Val Xaa Ser Leu Asp Ser Phe Glu Ser
    1385                1390                1395

Arg Xaa Ile Ala Ser Ser Val Gln Xaa Glu Pro Cys Xaa Gly Met
    1400                1405                1410
```

```
Val Xaa Gly Ile Ile Ser Pro Ser Asp Leu Pro Asp Xaa Pro Gly
    1415            1420                1425

Gln Xaa Met Pro Pro Xaa Arg Ser Lys Thr Pro Pro Pro Pro
    1430            1435                1440

Gln Thr Ala Gln Thr Lys Arg Glu Val Pro Lys Asn Lys Ala Pro
    1445            1450                1455

Thr Ala Glu Lys Arg Glu Ser Gly Pro Lys Gln Ala Ala Val Asn
    1460            1465                1470

Ala Ala Val Gln Arg Val Gln Val Leu Pro Asp Ala Asp Thr Leu
    1475            1480                1485

Leu His Phe Ala Thr Glu Ser Thr Pro Asp Gly Phe Ser Cys Ser
    1490            1495                1500

Ser Ser Leu Ser Ala Leu Ser Leu Asp Glu Pro Phe Ile Gln Lys
    1505            1510                1515

Asp Val Glu Leu Arg Ile Met Pro Pro Val Gln Glu Asn Asp Asn
    1520            1525                1530

Gly Asn Glu Thr Glu Ser Glu Gln Pro Lys Glu Ser Asn Glu Asn
    1535            1540                1545

Gln Glu Lys Glu Ala Glu Lys Thr Ile Asp Ser Glu Lys Asp Leu
    1550            1555                1560

Leu Asp Asp Ser Asp Asp Asp Asp Ile Glu Ile Leu Glu Glu Cys
    1565            1570                1575

Ile Ile Ser Ala Met Pro Thr Lys Ser Ser Arg Lys Ala Lys Lys
    1580            1585                1590

Pro Ala Gln Thr Ala Ser Lys Leu Pro Pro Pro Val Ala Arg Lys
    1595            1600                1605

Pro Ser Gln Leu Pro Val Tyr Lys Leu Leu Pro Ser Gln Asn Arg
    1610            1615                1620

Leu Gln Pro Gln Lys His Val Ser Phe Thr Pro Gly Asp Asp Met
    1625            1630                1635

Pro Arg Val Tyr Cys Val Glu Gly Thr Pro Ile Asn Phe Ser Thr
    1640            1645                1650

Ala Thr Ser Leu Ser Asp Leu Thr Ile Glu Ser Pro Pro Asn Glu
    1655            1660                1665

Leu Ala Ala Gly Glu Gly Val Arg Gly Gly Ala Gln Ser Gly Glu
    1670            1675                1680

Phe Glu Lys Arg Asp Thr Ile Pro Thr Glu Gly Arg Ser Thr Asp
    1685            1690                1695

Glu Ala Gln Gly Gly Lys Thr Ser Ser Val Thr Ile Pro Glu Leu
    1700            1705                1710

Asp Asp Asn Lys Ala Glu Glu Gly Asp Ile Leu Ala Glu Cys Ile
    1715            1720                1725

Asn Ser Ala Met Pro Lys Gly Lys Ser His Lys Pro Phe Arg Val
    1730            1735                1740

Lys Lys Ile Met Asp Gln Val Gln Gln Ala Ser Ala Ser Ser Ser
    1745            1750                1755

Ala Pro Asn Lys Asn Gln Leu Asp Gly Lys Lys Lys Lys Pro Thr
    1760            1765                1770

Ser Pro Val Lys Pro Ile Pro Gln Asn Thr Glu Tyr Arg Thr Arg
    1775            1780                1785

Val Arg Lys Asn Ala Asp Ser Lys Asn Asn Leu Asn Ala Glu Arg
    1790            1795                1800
```

```
Val Phe Ser Asp Asn Lys Asp Ser Lys Gln Asn Leu Lys Asn
    1805                1810                1815

Asn Ser Lys Val Phe Asn Asp Lys Leu Pro Asn Glu Asp Arg
    1820                1825                1830

Val Arg Gly Ser Phe Ala Phe Asp Ser Pro His His Tyr Thr Pro
    1835                1840                1845

Ile Glu Gly Thr Pro Tyr Cys Phe Ser Arg Asn Asp Ser Leu Ser
    1850                1855                1860

Ser Leu Asp Phe Asp Asp Asp Val Asp Leu Ser Arg Glu Lys
    1865                1870                1875

Ala Glu Leu Arg Lys Ala Lys Glu Asn Lys Glu Ser Glu Ala Lys
    1880                1885                1890

Val Thr Ser His Thr Glu Leu Thr Ser Asn Gln Gln Ser Ala Asn
    1895                1900                1905

Lys Thr Gln Ala Ile Ala Lys Gln Pro Ile Asn Arg Gly Gln Pro
    1910                1915                1920

Lys Pro Ile Leu Gln Lys Gln Ser Thr Phe Pro Gln Ser Ser Lys
    1925                1930                1935

Asp Ile Pro Asp Arg Gly Ala Ala Thr Asp Glu Lys Leu Gln Asn
    1940                1945                1950

Phe Ala Ile Glu Asn Thr Pro Val Cys Phe Ser His Asn Ser Ser
    1955                1960                1965

Leu Ser Ser Leu Ser Asp Ile Asp Gln Glu Asn Asn Asn Lys Glu
    1970                1975                1980

Asn Glu Pro Ile Lys Glu Thr Glu Pro Pro Asp Ser Gln Gly Glu
    1985                1990                1995

Pro Ser Lys Pro Gln Ala Ser Gly Tyr Ala Pro Lys Ser Phe His
    2000                2005                2010

Val Glu Asp Thr Pro Val Cys Phe Ser Arg Asn Ser Ser Leu Ser
    2015                2020                2025

Ser Leu Ser Ile Asp Ser Glu Asp Asp Leu Leu Gln Glu Cys Ile
    2030                2035                2040

Ser Ser Ala Met Pro Lys Lys Lys Lys Pro Ser Arg Leu Lys Gly
    2045                2050                2055

Asp Asn Glu Lys His Ser Pro Arg Asn Met Gly Gly Ile Leu Gly
    2060                2065                2070

Glu Asp Leu Thr Leu Asp Leu Lys Asp Ile Gln Arg Pro Asp Ser
    2075                2080                2085

Glu His Gly Leu Ser Pro Asp Ser Glu Asn Phe Asp Trp Lys Ala
    2090                2095                2100

Ile Gln Glu Gly Ala Asn Ser Ile Val Ser Ser Leu His Gln Ala
    2105                2110                2115

Ala Ala Ala Ala Cys Leu Ser Arg Gln Ala Ser Ser Asp Ser Asp
    2120                2125                2130

Ser Ile Leu Ser Leu Lys Ser Gly Ile Ser Leu Gly Ser Pro Phe
    2135                2140                2145

His Leu Thr Pro Asp Gln Glu Glu Lys Pro Phe Thr Ser Asn Lys
    2150                2155                2160

Gly Pro Arg Ile Leu Lys Pro Gly Glu Lys Ser Thr Leu Glu Thr
    2165                2170                2175

Lys Lys Ile Glu Ser Glu Ser Lys Gly Ile Lys Gly Gly Lys Lys
    2180                2185                2190

Val Tyr Lys Ser Leu Ile Thr Gly Lys Val Arg Ser Asn Ser Glu
```

```
                2195                2200                2205
Ile Ser Gly Gln Met Lys Gln Pro Leu Gln Ala Asn Met Pro Ser
    2210                2215                2220
Ile Ser Arg Gly Arg Thr Met Ile His Ile Pro Gly Val Arg Asn
    2225                2230                2235
Ser Ser Ser Ser Thr Ser Pro Val Ser Lys Lys Gly Pro Pro Leu
    2240                2245                2250
Lys Thr Pro Ala Ser Lys Ser Pro Ser Glu Gly Gln Thr Ala Thr
    2255                2260                2265
Thr Ser Pro Arg Gly Ala Lys Pro Ser Val Lys Ser Glu Leu Ser
    2270                2275                2280
Pro Val Ala Arg Gln Thr Ser Gln Ile Gly Gly Ser Ser Lys Ala
    2285                2290                2295
Pro Ser Arg Ser Gly Ser Arg Asp Ser Thr Pro Ser Arg Pro Ala
    2300                2305                2310
Gln Gln Pro Leu Ser Arg Pro Ile Gln Ser Pro Gly Arg Asn Ser
    2315                2320                2325
Ile Ser Pro Gly Arg Asn Gly Ile Ser Pro Pro Asn Lys Leu Ser
    2330                2335                2340
Gln Leu Pro Arg Thr Ser Ser Pro Ser Thr Ala Ser Thr Lys Ser
    2345                2350                2355
Ser Gly Ser Gly Lys Met Ser Tyr Thr Ser Pro Gly Arg Gln Met
    2360                2365                2370
Ser Gln Gln Asn Leu Thr Lys Gln Thr Gly Leu Ser Lys Asn Ala
    2375                2380                2385
Ser Ser Ile Pro Arg Ser Glu Ser Ala Ser Lys Gly Leu Asn Gln
    2390                2395                2400
Met Asn Asn Gly Asn Gly Ala Asn Lys Lys Val Glu Leu Ser Arg
    2405                2410                2415
Met Ser Ser Thr Lys Ser Ser Gly Ser Glu Ser Asp Arg Ser Glu
    2420                2425                2430
Arg Pro Val Leu Val Arg Gln Ser Thr Phe Ile Lys Glu Ala Pro
    2435                2440                2445
Ser Pro Thr Leu Arg Arg Lys Leu Glu Glu Ser Ala Ser Phe Glu
    2450                2455                2460
Ser Leu Ser Pro Ser Ser Arg Pro Ala Ser Pro Thr Arg Ser Gln
    2465                2470                2475
Ala Gln Thr Pro Val Leu Ser Pro Ser Leu Pro Asp Met Ser Leu
    2480                2485                2490
Ser Thr His Ser Ser Val Gln Ala Gly Gly Trp Arg Lys Leu Pro
    2495                2500                2505
Pro Asn Leu Ser Pro Thr Ile Glu Tyr Asn Asp Gly Arg Pro Ala
    2510                2515                2520
Lys Arg His Asp Ile Ala Arg Ser His Ser Glu Ser Pro Ser Arg
    2525                2530                2535
Leu Pro Ile Asn Arg Ser Gly Thr Trp Lys Arg Glu His Ser Lys
    2540                2545                2550
His Ser Ser Ser Leu Pro Arg Val Ser Thr Trp Arg Arg Thr Gly
    2555                2560                2565
Ser Ser Ser Ser Ile Leu Ser Ala Ser Ser Glu Ser Ser Glu Lys
    2570                2575                2580
Ala Lys Ser Glu Asp Glu Lys His Val Asn Ser Ile Ser Gly Thr
    2585                2590                2595
```

```
Lys Gln Ser Lys Glu Asn Gln Val Ser Ala Lys Gly Thr Trp Arg
        2600                2605                2610

Lys Ile Lys Glu Asn Glu Phe Ser Pro Thr Asn Ser Thr Ser Gln
    2615                2620                2625

Thr Val Ser Ser Gly Ala Thr Asn Gly Ala Glu Ser Lys Thr Leu
    2630                2635                2640

Ile Tyr Gln Met Ala Pro Ala Val Ser Lys Thr Glu Asp Val Trp
    2645                2650                2655

Val Arg Ile Glu Asp Cys Pro Ile Asn Asn Pro Arg Ser Gly Arg
    2660                2665                2670

Ser Pro Thr Gly Asn Thr Pro Pro Val Ile Asp Ser Val Ser Glu
    2675                2680                2685

Lys Ala Asn Pro Asn Ile Lys Asp Ser Lys Asp Asn Gln Ala Lys
    2690                2695                2700

Gln Asn Val Gly Asn Gly Ser Val Pro Met Arg Thr Val Gly Leu
    2705                2710                2715

Glu Asn Arg Leu Asn Ser Phe Ile Gln Val Asp Ala Pro Asp Gln
    2720                2725                2730

Lys Gly Thr Glu Ile Lys Pro Gly Gln Asn Asn Pro Val Pro Val
    2735                2740                2745

Ser Glu Thr Asn Glu Ser Ser Ile Val Glu Arg Thr Pro Phe Ser
    2750                2755                2760

Ser Ser Ser Ser Ser Lys His Ser Ser Pro Ser Gly Thr Val Ala
    2765                2770                2775

Ala Arg Val Thr Pro Phe Asn Tyr Asn Pro Ser Pro Arg Lys Ser
    2780                2785                2790

Ser Ala Asp Ser Thr Ser Ala Arg Pro Ser Gln Ile Pro Thr Pro
    2795                2800                2805

Val Asn Asn Asn Thr Lys Lys Arg Asp Ser Lys Thr Asp Ser Thr
    2810                2815                2820

Glu Ser Ser Gly Thr Gln Ser Pro Lys Arg His Ser Gly Ser Tyr
    2825                2830                2835

Leu Val Thr Ser Val
    2840

<210> SEQ ID NO 20
<211> LENGTH: 1255
<212> TYPE: PRT
<213> ORGANISM: Homo sapiens
<220> FEATURE:
<221> NAME/KEY: misc_feature
<222> LOCATION: (1223)..(1223)
<223> OTHER INFORMATION: Xaa can be any naturally occurring amino acid

<400> SEQUENCE: 20

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80
```

```
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
            100                 105                 110
Pro Pro Ala His Asp Val Thr Ser Ala Pro Asp Asn Lys Pro Ala Pro
            115                 120                 125
Gly Ser Thr Ala Pro Pro Ala His Gly Val Thr Ser Ala Pro Asp Thr
        130                 135                 140
Arg Pro Ala Pro Gly Ser Thr Ala Pro Pro Ala His Gly Val Thr Ser
145                 150                 155                 160
Ala Pro Asp Thr Arg Pro Ala Pro Gly Ser Thr Ala Pro Pro Ala His
                165                 170                 175
Gly Val Thr Ser Ala Pro Asp Thr Arg Pro Ala Pro Gly Ser Thr Ala
            180                 185                 190
Pro Pro Ala His Gly Val Thr Ser Ala Pro Asp Thr Arg Pro Ala Pro
            195                 200                 205
Gly Ser Thr Ala Pro Pro Ala His Gly Val Thr Ser Ala Pro Asp Thr
        210                 215                 220
Arg Pro Ala Pro Gly Ser Thr Ala Pro Pro Ala His Gly Val Thr Ser
225                 230                 235                 240
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
            260                 265                 270
Pro Pro Ala His Gly Val Thr Ser Ala Pro Asp Thr Arg Pro Ala Pro
            275                 280                 285
Gly Ser Thr Ala Pro Pro Ala His Gly Val Thr Ser Ala Pro Asp Thr
        290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
                325                 330                 335
Gly Val Thr Ser Ala Pro Asp Thr Arg Pro Ala Pro Gly Ser Thr Ala
            340                 345                 350
Pro Pro Ala His Gly Val Thr Ser Ala Pro Asp Thr Arg Pro Ala Pro
            355                 360                 365
Gly Ser Thr Ala Pro Pro Ala His Gly Val Thr Ser Ala Pro Asp Thr
        370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
        450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
```

```
                500                 505                 510
Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
        530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925
```

Gly Ser Thr Ala Pro Pro Ala His Gly Val Thr Ser Ala Pro Asp Asn
            930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
        995                 1000                1005

Ser Thr Lys Thr Asp Ala Ser Ser Thr His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Xaa Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Ala Ser Ala Asn Leu
    1250                1255

<210> SEQ ID NO 21
<211> LENGTH: 295
<212> TYPE: PRT
<213> ORGANISM: Homo sapiens
<220> FEATURE:
<221> NAME/KEY: misc_feature
<222> LOCATION: (286)..(286)
<223> OTHER INFORMATION: Xaa can be any naturally occurring amino acid

<400> SEQUENCE: 21

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
            85                  90                  95

Ser Arg Leu Gln Leu Leu Gly Ala Thr Cys Met Phe Val Ala Ser Lys
        100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
        130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
            165                 170                 175

Ile Ile Arg Lys His Ala Gln Thr Phe Val Ala Leu Cys Ala Thr Asp
        180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
            245                 250                 255

Ser Ser Leu Arg Gln Ala Gln Gln Asn Met Asp Pro Lys Ala Ala Glu
        260                 265                 270

Glu Glu Glu Glu Glu Glu Glu Val Asp Leu Ala Cys Xaa Pro Thr
        275                 280                 285

Asp Val Arg Asp Val Asp Ile
        290                 295

<210> SEQ ID NO 22
<211> LENGTH: 331
<212> TYPE: PRT
<213> ORGANISM: Homo sapiens
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid

<400> SEQUENCE: 22

Met Thr Ala Lys Met Glu Thr Thr Phe Tyr Asp Asp Ala Leu Asn Ala
1               5                   10                  15
```

```
Ser Phe Leu Pro Ser Glu Ser Gly Pro Tyr Gly Tyr Ser Asn Pro Lys
         20                  25                  30

Ile Leu Lys Gln Ser Met Thr Leu Asn Leu Ala Asp Pro Val Gly Ser
     35                  40                  45

Leu Lys Pro His Leu Arg Ala Lys Asn Ser Asp Leu Leu Thr Ser Pro
 50                  55                  60

Asp Val Gly Leu Leu Lys Leu Ala Ser Pro Glu Leu Glu Arg Leu Ile
 65                  70                  75                  80

Ile Gln Ser Ser Asn Gly His Ile Thr Thr Thr Pro Thr Pro Thr Gln
                 85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Gln Pro Pro
            195                 200                 205

His His Leu Pro Gln Gln Met Pro Val Gln His Pro Arg Leu Gln Ala
        210                 215                 220

Leu Lys Glu Glu Pro Gln Thr Val Pro Glu Met Pro Gly Glu Xaa Pro
225                 230                 235                 240

Pro Leu Xaa Pro Ile Asp Met Glu Xaa Gln Glu Arg Ile Lys Ala Glu
            245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
            275                 280                 285

Ala Gln Asn Ser Glu Leu Ala Ser Thr Ala Asn Met Leu Arg Glu Gln
        290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 23
<211> LENGTH: 344
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid

<400> SEQUENCE: 23
```

```
Met Cys Thr Lys Met Glu Gln Ala Phe Tyr His Asp Asp Ser Tyr Ala
1               5                   10                  15

Ala Ala Gly Tyr Gly Arg Ser Pro Gly Ser Leu Ser Leu His Asp Tyr
            20                  25                  30

Lys Leu Leu Lys Pro Thr Leu Ala Leu Asn Leu Ala Asp Pro Tyr Arg
            35                  40                  45

Gly Leu Lys Gly Pro Gly Ala Arg Gly Pro Gly Pro Glu Gly Ser Gly
50              55                  60

Ala Gly Ser Tyr Phe Ser Gly Gln Gly Ser Asp Thr Gly Ala Ser Leu
65                  70                  75                  80

Lys Leu Ala Ser Thr Glu Leu Glu Arg Leu Ile Val Pro Asn Ser Asn
                85                  90                  95

Gly Val Ile Thr Thr Thr Pro Thr Pro Pro Gly Gln Tyr Phe Tyr Pro
                100                 105                 110

Arg Gly Gly Gly Ser Gly Gly Gly Thr Gly Gly Gly Val Thr Glu Glu
            115                 120                 125

Gln Glu Gly Phe Ala Asp Gly Phe Val Lys Ala Leu Asp Asp Leu Gln
    130                 135                 140

Lys Met Asn His Val Thr Pro Pro Asn Val Ser Leu Gly Ala Ser Gly
145                 150                 155                 160

Gly Pro Gln Ala Gly Pro Gly Gly Val Tyr Ala Gly Pro Glu Pro Pro
            165                 170                 175

Pro Val Tyr Thr Asn Leu Ser Ser Tyr Ser Pro Ala Ser Ala Pro Ser
            180                 185                 190

Gly Gly Ser Gly Thr Ala Val Gly Thr Gly Ser Ser Tyr Pro Thr Ala
            195                 200                 205

Thr Ile Ser Tyr Leu Pro His Ala Pro Pro Phe Ala Gly His Pro
210                 215                 220

Ala Gln Leu Gly Leu Ser Arg Gly Ala Ser Ala Phe Lys Glu Glu Pro
225                 230                 235                 240

Gln Thr Val Pro Glu Ala Arg Ser Arg Asp Ala Xaa Pro Pro Val Xaa
            245                 250                 255

Pro Ile Asn Met Glu Asp Gln Glu Arg Ile Lys Val Glu Arg Lys Arg
            260                 265                 270

Leu Arg Asn Arg Leu Ala Ala Thr Lys Cys Arg Lys Arg Lys Leu Glu
            275                 280                 285

Arg Ile Ala Arg Leu Glu Asp Lys Val Lys Thr Leu Lys Ala Glu Asn
            290                 295                 300

Ala Gly Leu Ser Ser Ala Ala Gly Leu Leu Arg Glu Gln Val Ala Gln
305                 310                 315                 320

Leu Lys Gln Lys Val Met Thr His Val Ser Asn Gly Cys Gln Leu Leu
            325                 330                 335

Leu Gly Val Lys Gly His Ala Phe
            340
```

<210> SEQ ID NO 24
<211> LENGTH: 341
<212> TYPE: PRT
<213> ORGANISM: Mus musculus
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid

```
<220> FEATURE:
<221> NAME/KEY: misc_feature
<222> LOCATION: (259)..(259)
<223> OTHER INFORMATION: Xaa can be any naturally occurring amino acid

<400> SEQUENCE: 24
```

Met Glu Thr Pro Phe Tyr Gly Glu Glu Ala Leu Ser Gly Leu Ala Ala
1               5                   10                  15

Gly Ala Ser Ser Val Ala Gly Ala Thr Gly Ala Pro Gly Gly Gly Gly
            20                  25                  30

Phe Ala Pro Pro Gly Arg Ala Phe Pro Gly Ala Pro Pro Thr Ser Ser
        35                  40                  45

Met Leu Lys Lys Asp Ala Leu Thr Leu Ser Leu Ala Glu Gln Gly Ala
50                  55                  60

Ala Gly Leu Lys Pro Gly Ser Ala Thr Ala Pro Ser Ala Leu Arg Pro
65                  70                  75                  80

Asp Gly Ala Pro Asp Gly Leu Leu Ala Ser Pro Asp Leu Gly Leu Leu
                85                  90                  95

Lys Leu Ala Ser Pro Glu Leu Glu Arg Leu Ile Ile Gln Ser Asn Gly
            100                 105                 110

Leu Val Thr Thr Thr Pro Thr Ser Thr Gln Phe Leu Tyr Pro Lys Val
            115                 120                 125

Ala Ala Ser Glu Glu Gln Glu Phe Ala Glu Gly Phe Val Lys Ala Leu
130                 135                 140

Glu Asp Leu His Lys Gln Ser Gln Leu Gly Ala Ala Thr Ala Ala Thr
145                 150                 155                 160

Ser Gly Ala Pro Ala Pro Pro Ala Pro Ala Asp Leu Ala Ala Thr Pro
                165                 170                 175

Gly Ala Thr Glu Thr Pro Val Tyr Ala Asn Leu Ser Ser Phe Ala Gly
            180                 185                 190

Gly Ala Gly Pro Pro Gly Gly Ala Ala Thr Val Ala Phe Ala Ala Glu
            195                 200                 205

Pro Val Pro Phe Pro Pro Pro Gly Ala Leu Gly Pro Pro Pro Pro
210                 215                 220

Pro His Pro Pro Arg Leu Ala Ala Leu Lys Asp Glu Pro Gln Thr Val
225                 230                 235                 240

Pro Asp Val Pro Ser Phe Gly Asp Xaa Pro Pro Leu Xaa Pro Ile Asp
                245                 250                 255

Met Asp Xaa Gln Glu Arg Ile Lys Ala Glu Arg Lys Arg Leu Arg Asn
            260                 265                 270

Arg Ile Ala Ala Ser Lys Cys Arg Lys Arg Lys Leu Glu Arg Ile Ser
            275                 280                 285

Arg Leu Glu Glu Lys Val Lys Thr Leu Lys Ser Gln Asn Thr Glu Leu
290                 295                 300

Ala Ser Thr Ala Ser Leu Leu Arg Glu Gln Val Ala Gln Leu Lys Gln
305                 310                 315                 320

Lys Val Leu Ser His Val Asn Ser Gly Cys Gln Leu Leu Pro Gln His
                325                 330                 335

Gln Val Pro Ala Tyr
            340

```
<210> SEQ ID NO 25
<211> LENGTH: 439
<212> TYPE: PRT
<213> ORGANISM: Homo sapiens
<220> FEATURE:
```

```
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid

<400> SEQUENCE: 25

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Xaa Pro Pro Leu Ser Pro Ser
50                  55                  60

Arg Arg Xaa Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
            85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Lys Leu
130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
            165                 170                 175

Tyr Leu Gln Asp Leu Ser Ala Ala Ser Glu Cys Ile Asp Pro Ser
            180                 185                 190

Val Val Phe Pro Tyr Pro Leu Asn Asp Ser Ser Ser Pro Lys Ser Cys
            195                 200                 205

Ala Ser Gln Asp Ser Ser Ala Phe Ser Pro Ser Ser Asp Ser Leu Leu
        210                 215                 220

Ser Xaa Thr Glu Ser Xaa Pro Gln Gly Ser Pro Glu Pro Leu Val Leu
225                 230                 235                 240

His Glu Glu Thr Pro Pro Thr Thr Ser Ser Asp Ser Glu Glu Glu Gln
            245                 250                 255

Glu Asp Glu Glu Glu Ile Asp Val Val Ser Val Glu Lys Arg Gln Ala
            260                 265                 270

Pro Gly Lys Arg Xaa Glu Ser Gly Ser Pro Ser Ala Gly Gly His Ser
        275                 280                 285

Lys Pro Pro His Ser Pro Leu Val Leu Lys Arg Cys His Val Ser Thr
            290                 295                 300
```

```
His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
            325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
            355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
            405                 410                 415

Glu Asp Leu Leu Arg Lys Arg Arg Glu Gln Leu Lys His Lys Leu Glu
            420                 425                 430

Gln Leu Arg Asn Ser Cys Ala
            435

<210> SEQ ID NO 26
<211> LENGTH: 825
<212> TYPE: PRT
<213> ORGANISM: Homo sapiens
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid

<400> SEQUENCE: 26

Met Pro Ser Thr Ser Phe Pro Val Pro Ser Lys Phe Pro Leu Gly Pro
1               5                   10                  15

Ala Ala Ala Val Phe Gly Arg Gly Glu Thr Leu Gly Pro Ala Pro Arg
            20                  25                  30

Ala Gly Gly Thr Met Lys Ser Ala Glu Glu His Tyr Gly Tyr Ala
            35                  40                  45

Ser Ser Asn Val Ser Pro Ala Leu Pro Leu Pro Thr Ala His Ser Thr
    50                  55                  60
```

```
Leu Pro Ala Pro Cys His Asn Leu Gln Thr Ser Thr Pro Gly Ile Ile
 65                  70                  75                  80

Pro Pro Ala Asp His Pro Ser Gly Tyr Gly Ala Ala Leu Asp Gly Gly
                 85                  90                  95

Pro Ala Gly Tyr Phe Leu Ser Ser Gly His Thr Arg Pro Asp Gly Ala
            100                 105                 110

Pro Ala Leu Glu Ser Pro Arg Ile Glu Ile Thr Ser Cys Leu Gly Leu
        115                 120                 125

Tyr His Asn Asn Asn Gln Phe Phe His Asp Val Glu Val Glu Asp Val
    130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
            180                 185                 190

Tyr Ser Tyr Pro Tyr Ala Xaa Pro Gln Thr Xaa Pro Trp Gln Xaa Pro
        195                 200                 205

Cys Val Ser Pro Lys Thr Thr Asp Pro Glu Glu Gly Phe Pro Arg Gly
    210                 215                 220

Leu Gly Ala Cys Thr Leu Leu Gly Xaa Pro Arg His Xaa Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Xaa Pro His His Xaa Pro Thr Pro Xaa Pro His
        275                 280                 285

Gly Ser Pro Arg Val Ser Val Thr Asp Asp Ser Trp Leu Gly Asn Thr
    290                 295                 300

Thr Gln Tyr Thr Ser Ser Ala Ile Val Ala Ala Ile Asn Ala Leu Thr
305                 310                 315                 320

Thr Asp Ser Ser Leu Asp Leu Gly Asp Gly Val Pro Val Lys Ser Arg
                325                 330                 335

Lys Thr Thr Leu Glu Gln Pro Pro Ser Val Ala Leu Lys Val Glu Pro
            340                 345                 350

Val Gly Glu Asp Leu Gly Ser Pro Pro Pro Ala Asp Phe Ala Pro
        355                 360                 365

Glu Asp Tyr Ser Ser Phe Gln His Ile Arg Lys Gly Gly Phe Cys Asp
    370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro Ala Leu Asp
                405                 410                 415

Trp Gln Leu Pro Ser His Ser Gly Pro Tyr Glu Leu Arg Ile Glu Val
            420                 425                 430

Gln Pro Lys Ser His His Arg Ala His Tyr Glu Thr Glu Gly Ser Arg
        435                 440                 445

Gly Ala Val Lys Ala Ser Ala Gly Gly His Pro Ile Val Gln Leu His
    450                 455                 460

Gly Tyr Leu Glu Asn Glu Pro Leu Met Leu Gln Leu Phe Ile Gly Thr
465                 470                 475                 480

Ala Asp Asp Arg Leu Leu Arg Pro His Ala Phe Tyr Gln Val His Arg
```

```
                    485                 490                 495
Ile Thr Gly Lys Thr Val Ser Thr Thr Ser His Glu Ala Ile Leu Ser
            500                 505                 510

Asn Thr Lys Val Leu Glu Ile Pro Leu Leu Pro Glu Asn Ser Met Arg
        515                 520                 525

Ala Val Ile Asp Cys Ala Gly Ile Leu Lys Leu Arg Asn Ser Asp Ile
    530                 535                 540

Glu Leu Arg Lys Gly Glu Thr Asp Ile Gly Arg Lys Asn Thr Arg Val
545                 550                 555                 560

Arg Leu Val Phe Arg Val His Val Pro Gln Pro Ser Gly Arg Thr Leu
                565                 570                 575

Ser Leu Gln Val Ala Ser Asn Pro Ile Glu Cys Ser Gln Arg Ser Ala
            580                 585                 590

Gln Glu Leu Pro Leu Val Glu Lys Gln Ser Thr Asp Ser Tyr Pro Val
        595                 600                 605

Val Gly Gly Lys Lys Met Val Leu Ser Gly His Asn Phe Leu Gln Asp
    610                 615                 620

Ser Lys Val Ile Phe Val Glu Lys Ala Pro Asp Gly His His Val Trp
625                 630                 635                 640

Glu Met Glu Ala Lys Thr Asp Arg Asp Leu Cys Lys Pro Asn Ser Leu
                645                 650                 655

Val Val Glu Ile Pro Pro Phe Arg Asn Gln Arg Ile Thr Ser Pro Val
            660                 665                 670

His Val Ser Phe Tyr Val Cys Asn Gly Lys Arg Lys Arg Ser Gln Tyr
        675                 680                 685

Gln Arg Phe Thr Tyr Leu Pro Ala Asn Val Pro Ile Ile Lys Thr Glu
    690                 695                 700

Pro Thr Asp Asp Tyr Glu Pro Ala Pro Thr Cys Gly Pro Val Ser Gln
705                 710                 715                 720

Gly Leu Ser Pro Leu Pro Arg Pro Tyr Tyr Ser Gln Gln Leu Ala Met
                725                 730                 735

Pro Pro Asp Pro Ser Ser Cys Leu Val Ala Gly Phe Pro Pro Cys Pro
            740                 745                 750

Gln Arg Ser Thr Leu Met Pro Ala Ala Pro Gly Val Ser Pro Lys Leu
        755                 760                 765

His Asp Leu Ser Pro Ala Ala Tyr Thr Lys Gly Val Ala Ser Pro Gly
    770                 775                 780

His Cys His Leu Gly Leu Pro Gln Pro Ala Gly Glu Ala Pro Ala Val
785                 790                 795                 800

Gln Asp Val Pro Arg Pro Val Ala Thr His Pro Gly Ser Pro Gly Gln
                805                 810                 815

Pro Pro Pro Ala Leu Leu Pro Gln Gln
            820                 825

<210> SEQ ID NO 27
<211> LENGTH: 358
<212> TYPE: PRT
<213> ORGANISM: Homo sapiens
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
```

<400> SEQUENCE: 27

```
Met Glu Ser Ala Asp Phe Tyr Glu Ala Glu Pro Arg Pro Pro Met Ser
1               5                   10                  15

Ser His Leu Gln Ser Pro His Ala Pro Ser Ser Ala Ala Phe Gly
            20                  25                  30

Phe Pro Arg Gly Ala Gly Pro Lys Pro Pro Ala Pro Ala Ala
        35                  40                  45

Pro Glu Pro Leu Gly Gly Ile Cys Glu His Glu Thr Ser Ile Asp Ile
50                  55                  60

Ser Ala Tyr Ile Asp Pro Ala Ala Phe Asn Asp Glu Phe Leu Ala Asp
65                  70                  75                  80

Leu Phe Gln His Ser Arg Gln Gln Glu Lys Ala Lys Ala Ala Val Gly
                85                  90                  95

Pro Thr Gly Gly Gly Gly Gly Asp Phe Asp Tyr Pro Gly Ala Pro
                100                 105                 110

Ala Gly Pro Gly Gly Ala Val Met Pro Gly Gly Ala His Gly Pro Pro
                115                 120                 125

Pro Gly Tyr Gly Cys Ala Ala Ala Gly Tyr Leu Asp Gly Arg Leu Glu
    130                 135                 140

Pro Leu Tyr Glu Arg Val Gly Ala Pro Ala Leu Arg Pro Leu Val Ile
145                 150                 155                 160

Lys Gln Glu Pro Arg Glu Glu Asp Glu Ala Lys Gln Leu Ala Leu Ala
                165                 170                 175

Gly Leu Phe Pro Tyr Gln Pro Pro Pro Pro Pro Ser His Pro
            180                 185                 190

His Pro His Pro Pro Ala His Leu Ala Ala Pro His Leu Gln Phe
    195                 200                 205

Gln Ile Ala His Cys Gly Gln Thr Thr Met His Leu Gln Pro Gly His
    210                 215                 220

Pro Xaa Pro Pro Xaa Pro Val Pro Ser Pro His Pro Ala Pro Ala
225                 230                 235                 240

Leu Gly Ala Ala Gly Leu Pro Gly Pro Gly Ser Ala Leu Lys Gly Leu
                245                 250                 255

Gly Ala Ala His Pro Asp Leu Arg Ala Ser Gly Gly Thr Gly Ala Gly
                260                 265                 270

Lys Ala Lys Lys Ser Val Asp Lys Asn Ser Asn Glu Tyr Arg Val Arg
            275                 280                 285

Arg Glu Arg Asn Asn Ile Ala Val Arg Lys Ser Arg Asp Lys Ala Lys
        290                 295                 300

Gln Arg Asn Val Glu Thr Gln Gln Lys Val Leu Glu Leu Thr Ser Asp
305                 310                 315                 320

Asn Asp Arg Leu Arg Lys Arg Val Glu Gln Leu Ser Arg Glu Leu Asp
                325                 330                 335

Thr Leu Arg Gly Ile Phe Arg Gln Leu Pro Glu Ser Ser Leu Val Lys
            340                 345                 350

Ala Met Gly Asn Cys Ala
        355
```

<210> SEQ ID NO 28
<211> LENGTH: 296
<212> TYPE: PRT
<213> ORGANISM: Mus musculus
<220> FEATURE:
<221> NAME/KEY: misc_feature
<222> LOCATION: (180)..(180)

<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid

<400> SEQUENCE: 28

```
Met His Arg Leu Leu Ala Trp Asp Ala Ala Cys Leu Pro Pro Pro Pro
1               5                   10                  15
Ala Ala Phe Arg Pro Met Glu Val Ala Asn Phe Tyr Tyr Glu Pro Asp
            20                  25                  30
Cys Leu Ala Tyr Gly Ala Lys Ala Ala Arg Ala Ala Pro Arg Ala Pro
        35                  40                  45
Ala Ala Glu Pro Ala Ile Gly Glu His Glu Arg Ala Ile Asp Phe Ser
    50                  55                  60
Pro Tyr Leu Glu Pro Leu Ala Pro Ala Ala Asp Phe Ala Ala Pro Ala
65                  70                  75                  80
Pro Ala His His Asp Phe Leu Ser Asp Leu Phe Ala Asp Asp Tyr Gly
                85                  90                  95
Ala Lys Pro Ser Lys Lys Pro Ala Asp Tyr Gly Tyr Val Ser Leu Gly
            100                 105                 110
Arg Ala Gly Ala Lys Ala Ala Pro Ala Cys Phe Pro Pro Pro Pro Pro
        115                 120                 125
Pro Ala Ala Leu Lys Ala Glu Pro Gly Phe Glu Pro Ala Asp Cys Lys
    130                 135                 140
Arg Ala Asp Asp Ala Pro Ala Met Ala Ala Gly Phe Pro Phe Ala Leu
145                 150                 155                 160
Arg Ala Tyr Leu Gly Tyr Gln Ala Thr Pro Ser Gly Ser Ser Gly Ser
                165                 170                 175
Leu Ser Thr Xaa Ser Ser Ser Xaa Pro Pro Gly Thr Pro Ser Pro Ala
            180                 185                 190
Asp Ala Lys Ala Ala Pro Ala Ala Cys Phe Ala Gly Pro Pro Ala Ala
        195                 200                 205
Pro Ala Lys Ala Lys Ala Lys Lys Thr Val Asp Lys Leu Ser Asp Glu
    210                 215                 220
Tyr Lys Met Arg Arg Glu Arg Asn Asn Ile Ala Val Arg Lys Ser Arg
225                 230                 235                 240
Asp Lys Ala Lys Met Arg Asn Leu Glu Thr Gln His Lys Val Leu Glu
                245                 250                 255
Leu Thr Ala Glu Asn Glu Arg Leu Gln Lys Lys Val Glu Gln Leu Ser
            260                 265                 270
Arg Glu Leu Ser Thr Leu Arg Asn Leu Phe Lys Gln Leu Pro Glu Pro
        275                 280                 285
Leu Leu Ala Ser Ala Gly His Cys
    290                 295
```

<210> SEQ ID NO 29
<211> LENGTH: 345
<212> TYPE: PRT
<213> ORGANISM: Homo sapiens
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid

<400> SEQUENCE: 29

```
Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65              70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Xaa Ser Ser Ser Xaa Pro Pro Gly Thr Pro Ser Pro Ala Asp
225                 230                 235                 240

Ala Lys Ala Pro Pro Thr Ala Cys Tyr Ala Gly Ala Ala Pro Ala Pro
            245                 250                 255

Ser Gln Val Lys Ser Lys Ala Lys Lys Thr Val Asp Lys His Ser Asp
        260                 265                 270

Glu Tyr Lys Ile Arg Arg Glu Arg Asn Asn Ile Ala Val Arg Lys Ser
    275                 280                 285

Arg Asp Lys Ala Lys Met Arg Asn Leu Glu Thr Gln His Lys Val Leu
290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345
```

<210> SEQ ID NO 30
<211> LENGTH: 230
<212> TYPE: PRT
<213> ORGANISM: Homo sapiens
<220> FEATURE:
<221> NAME/KEY: misc_feature
<222> LOCATION: (129)..(129)
<223> OTHER INFORMATION: Xaa can be any naturally occurring amino acid

<400> SEQUENCE: 30

```
Met Thr Met Glu Ser Gly Ala Glu Asn Gln Gln Ser Gly Asp Ala Ala
1               5                   10                  15

Val Thr Glu Ala Glu Asn Gln Gln Met Thr Val Gln Ala Gln Pro Gln
                20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
50                  55                  60

Gln Val His Gly Val Ile Gln Ala Ala Gln Pro Ser Val Ile Gln Ser
65                  70                  75                  80

Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
            115                 120                 125

Xaa Arg Arg Pro Ser Tyr Arg Lys Ile Leu Asn Asp Leu Ser Ser Asp
            130                 135                 140

Ala Pro Gly Val Pro Arg Ile Glu Glu Glu Lys Ser Glu Glu Glu Thr
145                 150                 155                 160

Ser Ala Leu Pro Thr Gln Pro Ala Glu Glu Ala Ala Arg Lys Arg Glu
                165                 170                 175

Val Arg Leu Met Glu Asn Arg Glu Ala Ala Arg Glu Cys Arg Arg Lys
            180                 185                 190

Lys Lys Glu Tyr Val Lys Cys Leu Glu Asn Arg Val Ala Val Leu Glu
            195                 200                 205

Asn Gln Asn Lys Thr Leu Ile Glu Glu Leu Lys Ala Leu Lys Asp Leu
210                 215                 220

Tyr Cys His Lys Ser Asp
225                 230

<210> SEQ ID NO 31
<211> LENGTH: 419
<212> TYPE: PRT
<213> ORGANISM: Mus musculus
<220> FEATURE:
<221> NAME/KEY: misc_feature
<222> LOCATION: (298)..(298)
<223> OTHER INFORMATION: Xaa can be any naturally occurring amino acid

<400> SEQUENCE: 31

Met Leu Glu Met Leu Glu Tyr Ser His Tyr Gln Val Gln Thr His Leu
1               5                   10                  15

Glu Asn Pro Thr Lys Tyr His Ile Gln Gln Ala Gln Arg His Gln Val
                20                  25                  30

Lys Gln Tyr Leu Ser Thr Thr Leu Ala Asn Lys His Ala Ser Gln Val
            35                  40                  45

Leu Ser Ser Pro Cys Pro Asn Gln Pro Gly Asp His Ala Met Pro Pro
50                  55                  60

Val Pro Gly Ser Ser Ala Pro Asn Ser Pro Met Ala Met Leu Thr Leu
65                  70                  75                  80

Asn Ser Asn Cys Glu Lys Glu Ala Phe Tyr Lys Phe Glu Glu Gln Ser
                85                  90                  95

Arg Ala Glu Ser Glu Cys Pro Gly Met Asn Thr His Ser Arg Ala Ser
            100                 105                 110
```

```
Cys Met Gln Met Asp Asp Val Ile Asp Asp Ile Ile Ser Leu Glu Ser
            115                 120                 125

Ser Tyr Asn Glu Glu Ile Leu Gly Leu Met Asp Pro Ala Leu Gln Met
130                 135                 140

Ala Asn Thr Leu Pro Val Ser Gly Asn Leu Ile Asp Leu Tyr Ser Asn
145                 150                 155                 160

Gln Gly Leu Pro Pro Pro Gly Leu Thr Ile Ser Asn Ser Cys Pro Ala
            165                 170                 175

Asn Leu Pro Asn Ile Lys Arg Glu Leu Thr Ala Cys Ile Phe Pro Thr
            180                 185                 190

Glu Ser Glu Ala Arg Ala Leu Ala Lys Glu Arg Gln Lys Lys Asp Asn
            195                 200                 205

His Asn Leu Ile Glu Arg Arg Arg Arg Phe Asn Ile Asn Asp Arg Ile
            210                 215                 220

Lys Glu Leu Gly Thr Leu Ile Pro Lys Ser Asn Asp Pro Asp Met Arg
225                 230                 235                 240

Trp Asn Lys Gly Thr Ile Leu Lys Ala Ser Val Asp Tyr Ile Arg Lys
            245                 250                 255

Leu Gln Arg Glu Gln Gln Arg Ala Lys Asp Leu Glu Asn Arg Gln Lys
            260                 265                 270

Lys Leu Glu His Ala Asn Arg His Leu Leu Leu Arg Val Gln Glu Leu
            275                 280                 285

Glu Met Gln Ala Arg Ala His Gly Leu Xaa Leu Ile Pro Ser Thr Gly
            290                 295                 300

Leu Cys Ser Pro Asp Leu Val Asn Arg Ile Ile Lys Gln Glu Pro Val
305                 310                 315                 320

Leu Glu Asn Cys Ser Gln Glu Leu Val Gln His Gln Ala Asp Leu Thr
            325                 330                 335

Cys Thr Thr Thr Leu Asp Leu Thr Asp Gly Thr Ile Thr Phe Thr Asn
            340                 345                 350

Asn Leu Gly Thr Met Pro Glu Ser Ser Pro Ala Tyr Ser Ile Pro Arg
            355                 360                 365

Lys Met Gly Ser Asn Leu Glu Asp Ile Leu Met Asp Asp Ala Leu Ser
370                 375                 380

Pro Val Gly Val Thr Asp Pro Leu Leu Ser Ser Val Ser Pro Gly Ala
385                 390                 395                 400

Ser Lys Thr Ser Ser Arg Arg Ser Ser Met Ser Ala Glu Glu Thr Glu
            405                 410                 415

His Ala Cys

<210> SEQ ID NO 32
<211> LENGTH: 504
<212> TYPE: PRT
<213> ORGANISM: Homo sapiens
<220> FEATURE:
<221> NAME/KEY: misc_feature
<222> LOCATION: (383)..(383)
<223> OTHER INFORMATION: Xaa can be any naturally occurring amino acid

<400> SEQUENCE: 32

Met Glu Ala Leu Arg Val Gln Met Phe Met Pro Cys Ser Phe Glu Ser
1               5                   10                  15

Leu Tyr Leu Ser Ser Ala Glu His Pro Gly Ala Ser Lys Pro Pro Ile
            20                  25                  30

Ser Ser Ser Ser Met Thr Ser Arg Ile Leu Leu Arg Gln Gln Leu Met
            35                  40                  45
```

```
Arg Glu Gln Met Gln Glu Gln Glu Arg Arg Glu Gln Gln Gln Lys Leu
        50                  55                  60

Gln Ala Ala Gln Phe Met Gln Gln Arg Val Pro Val Ser Gln Thr Pro
 65                  70                  75                  80

Ala Ile Asn Val Ser Val Pro Thr Thr Leu Pro Ser Ala Thr Gln Val
                 85                  90                  95

Pro Met Glu Val Leu Lys Val Gln Thr His Leu Glu Asn Pro Thr Lys
                100                 105                 110

Tyr His Ile Gln Gln Ala Gln Arg Gln Gln Val Lys Gln Tyr Leu Ser
                115                 120                 125

Thr Thr Leu Ala Asn Lys His Ala Asn Gln Val Leu Ser Leu Pro Cys
                130                 135                 140

Pro Asn Gln Pro Gly Asp His Val Met Pro Val Pro Gly Ser Ser
145                 150                 155                 160

Ala Pro Asn Ser Pro Met Ala Met Leu Thr Leu Asn Ser Asn Cys Glu
                165                 170                 175

Lys Glu Gly Phe Tyr Lys Phe Glu Glu Gln Asn Arg Ala Glu Ser Glu
                180                 185                 190

Cys Pro Gly Met Asn Thr His Ser Arg Ala Ser Cys Met Gln Met Asp
                195                 200                 205

Asp Val Ile Asp Ile Ile Ser Leu Glu Ser Ser Tyr Asn Glu Glu
                210                 215                 220

Ile Leu Gly Leu Met Asp Pro Ala Leu Gln Met Ala Asn Thr Leu Pro
225                 230                 235                 240

Val Ser Gly Asn Leu Ile Asp Leu Tyr Gly Asn Gln Gly Leu Pro Pro
                245                 250                 255

Pro Gly Leu Thr Ile Ser Asn Ser Cys Pro Ala Asn Leu Pro Asn Ile
                260                 265                 270

Lys Arg Glu Leu Thr Glu Ser Glu Ala Arg Ala Leu Ala Lys Glu Arg
                275                 280                 285

Gln Lys Lys Asp Asn His Asn Leu Ile Glu Arg Arg Arg Arg Phe Asn
                290                 295                 300

Ile Asn Asp Arg Ile Lys Glu Leu Gly Thr Leu Ile Pro Lys Ser Asn
305                 310                 315                 320

Asp Pro Asp Met Arg Trp Asn Lys Gly Thr Ile Leu Lys Ala Ser Val
                325                 330                 335

Asp Tyr Ile Arg Lys Leu Gln Arg Glu Gln Gln Arg Ala Lys Glu Leu
                340                 345                 350

Glu Asn Arg Gln Lys Lys Leu Glu His Ala Asn Arg His Leu Leu Leu
                355                 360                 365

Arg Ile Gln Glu Leu Glu Met Gln Ala Arg Ala His Gly Leu Xaa Leu
370                 375                 380

Ile Pro Ser Thr Gly Leu Cys Ser Pro Asp Leu Val Asn Arg Ile Ile
385                 390                 395                 400

Lys Gln Glu Pro Val Leu Glu Asn Cys Ser Gln Asp Leu Leu Gln His
                405                 410                 415

His Ala Asp Leu Thr Cys Thr Thr Thr Leu Asp Leu Thr Asp Gly Thr
                420                 425                 430

Ile Thr Phe Asn Asn Asn Leu Gly Thr Gly Thr Glu Ala Asn Gln Ala
                435                 440                 445

Tyr Ser Val Pro Thr Lys Met Gly Ser Lys Leu Glu Asp Ile Leu Met
450                 455                 460
```

```
Asp Asp Thr Leu Ser Pro Val Gly Val Thr Asp Pro Leu Leu Ser Ser
465                 470                 475                 480

Val Ser Pro Gly Ala Ser Lys Thr Ser Ser Arg Arg Ser Ser Met Ser
            485                 490                 495

Met Glu Glu Thr Glu His Thr Cys
            500

<210> SEQ ID NO 33
<211> LENGTH: 529
<212> TYPE: PRT
<213> ORGANISM: Homo sapiens
<220> FEATURE:
<221> NAME/KEY: misc_feature
<222> LOCATION: (303)..(303)
<223> OTHER INFORMATION: Xaa can be any naturally occurring amino acid

<400> SEQUENCE: 33

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
                20                  25                  30

Ala Leu Ile Cys Trp Ser Pro Ser Gly Asn Ser Phe His Val Phe Asp
            35                  40                  45

Gln Gly Gln Phe Ala Lys Glu Val Leu Pro Lys Tyr Phe Lys His Asn
50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
            180                 185                 190

Leu Ile Ser Leu Val Gln Ser Asn Arg Ile Leu Gly Val Lys Arg Lys
        195                 200                 205

Ile Pro Leu Met Leu Asn Asp Ser Gly Ser Ala His Ser Met Pro Lys
    210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
        275                 280                 285

Leu Ser Ser Ser Pro Leu Val Arg Val Lys Glu Glu Pro Pro Xaa Pro
    290                 295                 300

Pro Gln Ser Pro Arg Val Glu Glu Ala Ser Pro Gly Arg Pro Ser Ser
```

```
                       305                 310                 315                 320
Val Asp Thr Leu Leu Ser Pro Thr Ala Leu Ile Asp Ser Ile Leu Arg
                    325                 330                 335
Glu Ser Glu Pro Ala Pro Ala Ser Val Thr Ala Leu Thr Asp Ala Arg
                340                 345                 350
Gly His Thr Asp Thr Glu Gly Arg Pro Pro Ser Pro Pro Thr Ser
            355                 360                 365
Thr Pro Glu Lys Cys Leu Ser Val Ala Cys Leu Asp Lys Asn Glu Leu
370                 375                 380
Ser Asp His Leu Asp Ala Met Asp Ser Asn Leu Asp Asn Leu Gln Thr
385                 390                 395                 400
Met Leu Ser Ser His Gly Phe Ser Val Asp Thr Ser Ala Leu Leu Asp
                405                 410                 415
Leu Phe Ser Pro Ser Val Thr Val Pro Asp Met Ser Leu Pro Asp Leu
                420                 425                 430
Asp Ser Ser Leu Ala Ser Ile Gln Glu Leu Leu Ser Pro Gln Glu Pro
                435                 440                 445
Pro Arg Pro Pro Glu Ala Glu Asn Ser Ser Pro Asp Ser Gly Lys Gln
            450                 455                 460
Leu Val His Tyr Thr Ala Gln Pro Leu Phe Leu Leu Asp Pro Gly Ser
465                 470                 475                 480
Val Asp Thr Gly Ser Asn Asp Leu Pro Val Leu Phe Glu Leu Gly Glu
                485                 490                 495
Gly Ser Tyr Phe Ser Glu Gly Asp Gly Phe Ala Glu Asp Pro Thr Ile
                500                 505                 510
Ser Leu Leu Thr Gly Ser Glu Pro Pro Lys Ala Lys Asp Pro Thr Val
            515                 520                 525
Ser

<210> SEQ ID NO 34
<211> LENGTH: 758
<212> TYPE: PRT
<213> ORGANISM: Homo sapiens
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid

<400> SEQUENCE: 34

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Xaa Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
            100                 105                 110
```

```
Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Xaa Pro Gln Asp Ser Pro Pro Ser Lys Ala Ser Pro Ala
225                 230                 235                 240

Gln Asp Gly Arg Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
    275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525
```

```
Thr Pro Ser Leu Pro Thr Pro Pro Thr Arg Glu Pro Lys Lys Val Ala
        530                 535                 540

Val Val Arg Thr Pro Pro Lys Ser Pro Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 35
<211> LENGTH: 2468
<212> TYPE: PRT
<213> ORGANISM: Homo sapiens
<220> FEATURE:
<221> NAME/KEY: misc_feature
<222> LOCATION: (1205)..(1205)
<223> OTHER INFORMATION: Xaa can be any naturally occurring amino acid
<220> FEATURE:
<221> NAME/KEY: misc_feature
<222> LOCATION: (1244)..(1244)
<223> OTHER INFORMATION: Xaa can be any naturally occurring amino acid
<220> FEATURE:
<221> NAME/KEY: misc_feature
<222> LOCATION: (1248)..(1248)
<223> OTHER INFORMATION: Xaa can be any naturally occurring amino acid
<220> FEATURE:
<221> NAME/KEY: misc_feature
<222> LOCATION: (1252)..(1252)
<223> OTHER INFORMATION: Xaa can be any naturally occurring amino acid
<220> FEATURE:
<221> NAME/KEY: misc_feature
<222> LOCATION: (1256)..(1256)
<223> OTHER INFORMATION: Xaa can be any naturally occurring amino acid

<400> SEQUENCE: 35

Met Ala Thr Val Val Glu Ala Thr Glu Pro Glu Pro Ser Gly Ser
1               5                   10                  15

Ile Ala Asn Pro Ala Ala Ser Thr Ser Pro Ser Leu Ser His Arg Phe
            20                  25                  30
```

```
Leu Asp Ser Lys Phe Tyr Leu Val Val Gly Glu Ile Val Thr
         35                  40              45

Glu Glu His Leu Arg Arg Ala Ile Gly Asn Ile Glu Leu Gly Ile Arg
 50                  55                  60

Ser Trp Asp Thr Asn Leu Ile Glu Cys Asn Leu Asp Gln Glu Leu Lys
 65              70                  75                      80

Leu Phe Val Ser Arg His Ser Ala Arg Phe Ser Pro Glu Val Pro Gly
                 85                  90                  95

Gln Lys Ile Leu His His Arg Ser Asp Val Leu Glu Thr Val Val Leu
            100                 105                 110

Ile Asn Pro Ser Asp Glu Ala Val Ser Thr Glu Val Arg Leu Met Ile
            115                 120                 125

Thr Asp Ala Ala Arg His Lys Leu Leu Val Leu Thr Gly Gln Cys Phe
130                 135                 140

Glu Asn Thr Gly Glu Leu Ile Leu Gln Ser Gly Ser Phe Ser Phe Gln
145                 150                 155                 160

Asn Phe Ile Glu Ile Phe Thr Asp Gln Glu Ile Gly Glu Leu Leu Ser
                165                 170                 175

Thr Thr His Pro Ala Asn Lys Ala Ser Leu Thr Leu Phe Cys Pro Glu
            180                 185                 190

Glu Gly Asp Trp Lys Asn Ser Asn Leu Asp Arg His Asn Leu Gln Asp
            195                 200                 205

Phe Ile Asn Ile Lys Leu Asn Ser Ala Ser Ile Leu Pro Glu Met Glu
210                 215                 220

Gly Leu Ser Glu Phe Thr Glu Tyr Leu Ser Glu Ser Val Glu Val Pro
225                 230                 235                 240

Ser Pro Phe Asp Ile Leu Glu Pro Pro Thr Ser Gly Gly Phe Leu Lys
                245                 250                 255

Leu Ser Lys Pro Cys Cys Tyr Ile Phe Pro Gly Gly Arg Gly Asp Ser
            260                 265                 270

Ala Leu Phe Ala Val Asn Gly Phe Asn Met Leu Ile Asn Gly Gly Ser
            275                 280                 285

Glu Arg Lys Ser Cys Phe Trp Lys Leu Ile Arg His Leu Asp Arg Val
290                 295                 300

Asp Ser Ile Leu Leu Thr His Ile Gly Asp Asp Asn Leu Pro Gly Ile
305                 310                 315                 320

Asn Ser Met Leu Gln Arg Lys Ile Ala Glu Leu Glu Glu Glu Gln Ser
                325                 330                 335

Gln Gly Ser Thr Thr Asn Ser Asp Trp Met Lys Asn Leu Ile Ser Pro
            340                 345                 350

Asp Leu Gly Val Val Phe Leu Asn Val Pro Glu Asn Leu Lys Asn Pro
            355                 360                 365

Glu Pro Asn Ile Lys Met Lys Arg Ser Ile Glu Glu Ala Cys Phe Thr
370                 375                 380

Leu Gln Tyr Leu Asn Lys Leu Ser Met Lys Pro Glu Pro Leu Phe Arg
385                 390                 395                 400

Ser Val Gly Asn Thr Ile Asp Pro Val Ile Leu Phe Gln Lys Met Gly
                405                 410                 415

Val Gly Lys Leu Glu Met Tyr Val Leu Asn Pro Val Lys Ser Ser Lys
            420                 425                 430

Glu Met Gln Tyr Phe Met Gln Gln Trp Thr Gly Thr Asn Lys Asp Lys
            435                 440                 445

Ala Glu Phe Ile Leu Pro Asn Gly Gln Glu Val Asp Leu Pro Ile Ser
```

```
                450             455             460
Tyr Leu Thr Ser Val Ser Ser Leu Ile Val Trp His Pro Ala Asn Pro
465                     470                 475                 480

Ala Glu Lys Ile Ile Arg Val Leu Phe Pro Gly Asn Ser Thr Gln Tyr
                    485                 490                 495

Asn Ile Leu Glu Gly Leu Glu Lys Leu Lys His Leu Asp Phe Leu Lys
                500                 505                 510

Gln Pro Leu Ala Thr Gln Lys Asp Leu Thr Gly Gln Val Pro Thr Pro
                515                 520                 525

Val Val Lys Gln Thr Lys Leu Lys Gln Arg Ala Asp Ser Arg Glu Ser
        530                 535                 540

Leu Lys Pro Ala Ala Lys Pro Leu Pro Ser Lys Ser Val Arg Lys Glu
545                 550                 555                 560

Ser Lys Glu Glu Thr Pro Glu Val Thr Lys Val Asn His Val Glu Lys
                    565                 570                 575

Pro Pro Lys Val Glu Ser Lys Glu Lys Val Met Val Lys Lys Asp Lys
                580                 585                 590

Pro Val Lys Thr Glu Thr Lys Pro Ser Val Thr Glu Lys Glu Val Pro
                595                 600                 605

Ser Lys Glu Glu Pro Ser Pro Val Lys Ala Glu Val Ala Glu Lys Gln
                610                 615                 620

Ala Thr Asp Val Lys Pro Lys Ala Ala Lys Glu Lys Thr Val Lys Lys
625                 630                 635                 640

Glu Thr Lys Val Lys Pro Glu Asp Lys Lys Glu Glu Lys Glu Lys Pro
                    645                 650                 655

Lys Lys Glu Val Ala Lys Lys Glu Asp Lys Thr Pro Ile Lys Lys Glu
                660                 665                 670

Glu Lys Pro Lys Lys Glu Val Lys Lys Glu Val Lys Lys Glu Lys Ile
                675                 680                 685

Lys Lys Glu Glu Lys Lys Glu Pro Lys Lys Glu Val Lys Lys Glu Thr
            690                 695                 700

Pro Pro Lys Glu Val Lys Lys Glu Val Lys Lys Glu Glu Lys Lys Glu
705                 710                 715                 720

Val Lys Lys Glu Glu Lys Pro Lys Lys Glu Ile Lys Lys Glu Leu Pro
                    725                 730                 735

Lys Asp Ala Lys Lys Ser Ser Thr Pro Leu Ser Glu Ala Lys Lys Pro
                740                 745                 750

Ala Ala Leu Lys Pro Lys Val Pro Lys Glu Glu Ser Val Lys Lys Lys
                755                 760                 765

Asp Ser Val Ala Ala Gly Lys Pro Lys Glu Lys Gly Lys Ile Lys Val
                770                 775                 780

Ile Lys Lys Glu Gly Lys Ala Ala Glu Ala Ala Ala Ala Val Gly
785                 790                 795                 800

Thr Gly Ala Thr Thr Ala Ala Val Met Ala Ala Gly Ile Ala Ala
                    805                 810                 815

Ile Gly Pro Ala Lys Glu Leu Glu Ala Glu Arg Ser Leu Met Ser Ser
                820                 825                 830

Pro Glu Asp Leu Thr Lys Asp Phe Glu Glu Leu Lys Ala Glu Glu Val
                835                 840                 845

Asp Val Thr Lys Asp Ile Lys Pro Gln Leu Glu Leu Ile Glu Asp Glu
            850                 855                 860

Glu Lys Leu Lys Glu Thr Glu Pro Val Glu Ala Tyr Val Ile Gln Lys
865                 870                 875                 880
```

```
Glu Arg Glu Val Thr Lys Gly Pro Ala Glu Ser Pro Asp Glu Gly Ile
            885                 890                 895

Thr Thr Thr Glu Gly Glu Gly Glu Cys Glu Gln Thr Pro Glu Glu Leu
            900                 905                 910

Glu Pro Val Glu Lys Gln Gly Val Asp Asp Ile Glu Lys Phe Glu Asp
            915                 920                 925

Glu Gly Ala Gly Phe Glu Glu Ser Ser Glu Thr Gly Asp Tyr Glu Glu
            930                 935                 940

Lys Ala Glu Thr Glu Glu Ala Glu Glu Pro Glu Glu Asp Gly Glu Glu
945                 950                 955                 960

His Val Cys Val Ser Ala Ser Lys His Ser Pro Thr Glu Asp Glu Glu
            965                 970                 975

Ser Ala Lys Ala Glu Ala Asp Ala Tyr Ile Arg Glu Lys Arg Glu Ser
            980                 985                 990

Val Ala Ser Gly Asp Asp Arg Ala Glu Glu Asp Met Asp Glu Ala Ile
            995                 1000                1005

Glu Lys Gly Glu Ala Glu Gln Ser Glu Glu Ala Asp Glu Glu
            1010                1015                1020

Asp Lys Ala Glu Asp Ala Arg Glu Glu Glu Tyr Glu Pro Glu Lys
            1025                1030                1035

Met Glu Ala Glu Asp Tyr Val Met Ala Val Val Asp Lys Ala Ala
            1040                1045                1050

Glu Ala Gly Gly Ala Glu Glu Gln Tyr Gly Phe Leu Thr Thr Pro
            1055                1060                1065

Thr Lys Gln Leu Gly Ala Gln Ser Pro Gly Arg Glu Pro Ala Ser
            1070                1075                1080

Ser Ile His Asp Glu Thr Leu Pro Gly Gly Ser Glu Ser Glu Ala
            1085                1090                1095

Thr Ala Ser Asp Glu Glu Asn Arg Glu Asp Gln Pro Glu Glu Phe
            1100                1105                1110

Thr Ala Thr Ser Gly Tyr Thr Gln Ser Thr Ile Glu Ile Ser Ser
            1115                1120                1125

Glu Pro Thr Pro Met Asp Glu Met Ser Thr Pro Arg Asp Val Met
            1130                1135                1140

Ser Asp Glu Thr Asn Asn Glu Glu Thr Glu Ser Pro Ser Gln Glu
            1145                1150                1155

Phe Val Asn Ile Thr Lys Tyr Glu Ser Ser Leu Tyr Ser Gln Glu
            1160                1165                1170

Tyr Ser Lys Pro Ala Asp Val Thr Pro Leu Asn Gly Phe Ser Glu
            1175                1180                1185

Gly Ser Lys Thr Asp Ala Thr Asp Gly Lys Asp Tyr Asn Ala Ser
            1190                1195                1200

Ala Xaa Thr Ile Ser Pro Pro Ser Ser Met Glu Glu Asp Lys Phe
            1205                1210                1215

Ser Arg Ser Ala Leu Arg Asp Ala Tyr Cys Ser Glu Val Lys Ala
            1220                1225                1230

Ser Thr Thr Leu Asp Ile Lys Asp Ser Ile Xaa Ala Val Ser Xaa
            1235                1240                1245

Glu Lys Val Xaa Pro Ser Lys Xaa Pro Ser Leu Ser Pro Ser Pro
            1250                1255                1260

Pro Ser Pro Leu Glu Lys Thr Pro Leu Gly Glu Arg Ser Val Asn
            1265                1270                1275
```

```
Phe Ser Leu Thr Pro Asn Glu Ile Lys Val Ser Ala Glu Ala Glu
    1280             1285             1290

Val Ala Pro Val Ser Pro Glu Val Thr Gln Glu Val Val Glu Glu
    1295             1300             1305

His Cys Ala Ser Pro Glu Asp Lys Thr Leu Glu Val Val Ser Pro
    1310             1315             1320

Ser Gln Ser Val Thr Gly Ser Ala Gly His Thr Pro Tyr Tyr Gln
    1325             1330             1335

Ser Pro Thr Asp Glu Lys Ser Ser His Leu Pro Thr Glu Val Ile
    1340             1345             1350

Glu Lys Pro Pro Ala Val Pro Val Ser Phe Glu Phe Ser Asp Ala
    1355             1360             1365

Lys Asp Glu Asn Glu Arg Ala Ser Val Ser Pro Met Asp Glu Pro
    1370             1375             1380

Val Pro Asp Ser Glu Ser Pro Ile Glu Lys Val Leu Ser Pro Leu
    1385             1390             1395

Arg Ser Pro Pro Leu Ile Gly Ser Glu Ser Ala Tyr Glu Ser Phe
    1400             1405             1410

Leu Ser Ala Asp Asp Lys Ala Ser Gly Arg Gly Ala Glu Ser Pro
    1415             1420             1425

Phe Glu Glu Lys Ser Gly Lys Gln Gly Ser Pro Asp Gln Val Ser
    1430             1435             1440

Pro Val Ser Glu Met Thr Ser Thr Ser Leu Tyr Gln Asp Lys Gln
    1445             1450             1455

Glu Gly Lys Ser Thr Asp Phe Ala Pro Ile Lys Glu Asp Phe Gly
    1460             1465             1470

Gln Glu Lys Lys Thr Asp Val Glu Ala Met Ser Ser Gln Pro
    1475             1480             1485

Ala Leu Ala Leu Asp Glu Arg Lys Leu Gly Asp Val Ser Pro Thr
    1490             1495             1500

Gln Ile Asp Val Ser Gln Phe Gly Ser Phe Lys Glu Asp Thr Lys
    1505             1510             1515

Met Ser Ile Ser Glu Gly Thr Val Ser Asp Lys Ser Ala Thr Pro
    1520             1525             1530

Val Asp Glu Gly Val Ala Glu Asp Thr Tyr Ser His Met Glu Gly
    1535             1540             1545

Val Ala Ser Val Ser Thr Ala Ser Val Ala Thr Ser Ser Phe Pro
    1550             1555             1560

Glu Pro Thr Thr Asp Asp Val Ser Pro Ser Leu His Ala Glu Val
    1565             1570             1575

Gly Ser Pro His Ser Thr Glu Val Asp Asp Ser Leu Ser Val Ser
    1580             1585             1590

Val Val Gln Thr Pro Thr Thr Phe Gln Glu Thr Glu Met Ser Pro
    1595             1600             1605

Ser Lys Glu Glu Cys Pro Arg Pro Met Ser Ile Ser Pro Pro Asp
    1610             1615             1620

Phe Ser Pro Lys Thr Ala Lys Ser Arg Thr Pro Val Gln Asp His
    1625             1630             1635

Arg Ser Glu Gln Ser Ser Met Ser Ile Glu Phe Gly Gln Glu Ser
    1640             1645             1650

Pro Glu Gln Ser Leu Ala Met Asp Phe Ser Arg Gln Ser Pro Asp
    1655             1660             1665

His Pro Thr Val Gly Ala Gly Val Leu His Ile Thr Glu Asn Gly
```

```
            1670                1675                1680

Pro Thr Glu Val Asp Tyr Ser Pro Ser Asp Met Gln Asp Ser Ser
        1685                1690                1695

Leu Ser His Lys Ile Pro Pro Met Glu Glu Pro Ser Tyr Thr Gln
        1700                1705                1710

Asp Asn Asp Leu Ser Glu Leu Ile Ser Val Ser Gln Val Glu Ala
        1715                1720                1725

Ser Pro Ser Thr Ser Ser Ala His Thr Pro Ser Gln Ile Ala Ser
        1730                1735                1740

Pro Leu Gln Glu Asp Thr Leu Ser Asp Val Ala Pro Pro Arg Asp
        1745                1750                1755

Met Ser Leu Tyr Ala Ser Leu Thr Ser Glu Lys Val Gln Ser Leu
        1760                1765                1770

Glu Gly Glu Lys Leu Ser Pro Lys Ser Asp Ile Ser Pro Leu Thr
        1775                1780                1785

Pro Arg Glu Ser Ser Pro Leu Tyr Ser Pro Thr Phe Ser Asp Ser
        1790                1795                1800

Thr Ser Ala Val Lys Glu Lys Thr Ala Thr Cys His Ser Ser Ser
        1805                1810                1815

Ser Pro Pro Ile Asp Ala Ala Ser Ala Glu Pro Tyr Gly Phe Arg
        1820                1825                1830

Ala Ser Val Leu Phe Asp Thr Met Gln His His Leu Ala Leu Asn
        1835                1840                1845

Arg Asp Leu Ser Thr Pro Gly Leu Glu Lys Asp Ser Gly Gly Lys
        1850                1855                1860

Thr Pro Gly Asp Phe Ser Tyr Ala Tyr Gln Lys Pro Glu Glu Thr
        1865                1870                1875

Thr Arg Ser Pro Asp Glu Glu Asp Tyr Asp Tyr Glu Ser Tyr Glu
        1880                1885                1890

Lys Thr Thr Arg Thr Ser Asp Val Gly Gly Tyr Tyr Tyr Glu Lys
        1895                1900                1905

Ile Glu Arg Thr Thr Lys Ser Pro Ser Asp Ser Gly Tyr Ser Tyr
        1910                1915                1920

Glu Thr Ile Gly Lys Thr Thr Lys Thr Pro Glu Asp Gly Asp Tyr
        1925                1930                1935

Ser Tyr Glu Ile Ile Glu Lys Thr Thr Arg Thr Pro Glu Glu Gly
        1940                1945                1950

Gly Tyr Ser Tyr Asp Ile Ser Glu Lys Thr Thr Ser Pro Pro Glu
        1955                1960                1965

Val Ser Gly Tyr Ser Tyr Glu Lys Thr Glu Arg Ser Arg Arg Leu
        1970                1975                1980

Leu Asp Asp Ile Ser Asn Gly Tyr Asp Asp Ser Glu Asp Gly Gly
        1985                1990                1995

His Thr Leu Gly Asp Pro Ser Tyr Ser Tyr Glu Thr Thr Glu Lys
        2000                2005                2010

Ile Thr Ser Phe Pro Glu Ser Glu Gly Tyr Ser Tyr Glu Thr Ser
        2015                2020                2025

Thr Lys Thr Thr Arg Thr Pro Asp Thr Ser Thr Tyr Cys Tyr Glu
        2030                2035                2040

Thr Ala Glu Lys Ile Thr Arg Thr Pro Gln Ala Ser Thr Tyr Ser
        2045                2050                2055

Tyr Glu Thr Ser Asp Leu Cys Tyr Thr Ala Glu Lys Lys Ser Pro
        2060                2065                2070
```

```
Ser Glu Ala Arg Gln Asp Val Asp Leu Cys Leu Val Ser Ser Cys
2075                2080                2085

Glu Tyr Lys His Pro Lys Thr Glu Leu Ser Pro Ser Phe Ile Asn
2090                2095                2100

Pro Asn Pro Leu Glu Trp Phe Ala Ser Glu Glu Pro Thr Glu Glu
2105                2110                2115

Ser Glu Lys Pro Leu Thr Gln Ser Gly Gly Ala Pro Pro Pro Pro
2120                2125                2130

Gly Gly Lys Gln Gln Gly Arg Gln Cys Asp Glu Thr Pro Pro Thr
2135                2140                2145

Ser Val Ser Glu Ser Ala Pro Ser Gln Thr Asp Ser Asp Val Pro
2150                2155                2160

Pro Glu Thr Glu Glu Cys Pro Ser Ile Thr Ala Asp Ala Asn Ile
2165                2170                2175

Asp Ser Glu Asp Glu Ser Glu Thr Ile Pro Thr Asp Lys Thr Val
2180                2185                2190

Thr Tyr Lys His Met Asp Pro Pro Ala Pro Val Gln Asp Arg
2195                2200                2205

Ser Pro Ser Pro Arg His Pro Asp Val Ser Met Val Asp Pro Glu
2210                2215                2220

Ala Leu Ala Ile Glu Gln Asn Leu Gly Lys Ala Leu Lys Lys Asp
2225                2230                2235

Leu Lys Glu Lys Thr Lys Thr Lys Lys Pro Gly Thr Lys Thr Lys
2240                2245                2250

Ser Ser Ser Pro Val Lys Lys Ser Asp Gly Lys Ser Lys Pro Leu
2255                2260                2265

Ala Ala Ser Pro Lys Pro Ala Gly Leu Lys Glu Ser Ser Asp Lys
2270                2275                2280

Val Ser Arg Val Ala Ser Pro Lys Lys Lys Glu Ser Val Glu Lys
2285                2290                2295

Ala Ala Lys Pro Thr Thr Thr Pro Glu Val Lys Ala Ala Arg Gly
2300                2305                2310

Glu Glu Lys Asp Lys Glu Thr Lys Asn Ala Ala Asn Ala Ser Ala
2315                2320                2325

Ser Lys Ser Ala Lys Thr Ala Thr Ala Gly Pro Gly Thr Thr Lys
2330                2335                2340

Thr Thr Lys Ser Ser Ala Val Pro Pro Gly Leu Pro Val Tyr Leu
2345                2350                2355

Asp Leu Cys Tyr Ile Pro Asn His Ser Asn Ser Lys Asn Val Asp
2360                2365                2370

Val Glu Phe Phe Lys Arg Val Arg Ser Ser Tyr Tyr Val Val Ser
2375                2380                2385

Gly Asn Asp Pro Ala Ala Glu Glu Pro Ser Arg Ala Val Leu Asp
2390                2395                2400

Ala Leu Leu Glu Gly Lys Ala Gln Trp Gly Ser Asn Met Gln Val
2405                2410                2415

Thr Leu Ile Pro Thr His Asp Ser Glu Val Met Arg Glu Trp Tyr
2420                2425                2430

Gln Glu Thr His Glu Lys Gln Gln Asp Leu Asn Ile Met Val Leu
2435                2440                2445

Ala Ser Ser Ser Thr Val Val Met Gln Asp Glu Ser Phe Pro Ala
2450                2455                2460
```

```
Cys Lys Ile Glu Leu
    2465
```

<210> SEQ ID NO 36
<211> LENGTH: 467
<212> TYPE: PRT
<213> ORGANISM: Homo sapiens
<220> FEATURE:
<221> NAME/KEY: misc_feature
<222> LOCATION: (353)..(353)
<223> OTHER INFORMATION: Xaa can be any naturally occurring amino acid

<400> SEQUENCE: 36

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
```

```
                    340                 345                 350
Xaa Thr Pro Glu Ser Arg Ala Ala Val Gln Glu Leu Ser Ser Ser Ile
            355                 360                 365

Leu Ala Gly Glu Asp Pro Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
            405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
    450                 455                 460

Phe Tyr Ile
465

<210> SEQ ID NO 37
<211> LENGTH: 595
<212> TYPE: PRT
<213> ORGANISM: Homo sapiens
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 37

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Xaa Val Xaa Pro Xaa Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175
```

```
Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
```

```
<210> SEQ ID NO 38
<211> LENGTH: 309
<212> TYPE: PRT
<213> ORGANISM: cytomegalovirus
<220> FEATURE:
<221> NAME/KEY: misc_feature
<222> LOCATION: (231)..(231)
<223> OTHER INFORMATION: Xaa can be any naturally occurring amino acid

<400> SEQUENCE: 38
```

Met Ser His Pro Met Ser Ala Val Ala Thr Pro Ala Ala Ser Thr Val
1               5                   10                  15

Ala Pro Ser Gln Ala Pro Leu Ala Leu Ala His Asp Gly Val Tyr Leu
            20                  25                  30

Pro Lys Asp Ala Phe Phe Ser Leu Ile Gly Ala Ser Arg Pro Leu Ala
        35                  40                  45

Glu Ala Ala Gly Ala Arg Ala Ala Tyr Pro Ala Val Pro Pro Pro Pro
50                  55                  60

Ala Tyr Pro Val Met Asn Tyr Glu Asp Pro Ser Ser Arg His Phe Asp
65                  70                  75                  80

Tyr Ser Ala Trp Leu Arg Arg Pro Ala Tyr Asp Ala Val Pro Pro Leu
                85                  90                  95

Pro Pro Pro Pro Val Met Pro Met Pro Tyr Arg Arg Arg Asp Pro Met
            100                 105                 110

Met Glu Glu Ala Glu Arg Ala Ala Trp Glu Arg Gly Tyr Ala Pro Ser
        115                 120                 125

Ala Tyr Asp His Tyr Val Asn Asn Gly Ser Trp Ser Arg Ser Arg Ser
130                 135                 140

Gly Ala Leu Lys Arg Arg Arg Glu Arg Asp Ala Ser Ser Asp Glu Glu
145                 150                 155                 160

Glu Asp Met Ser Phe Pro Gly Glu Ala Asp His Gly Lys Ala Arg Lys
                165                 170                 175

Arg Leu Lys Ala His His Gly Arg Asp Asn Asn Asn Ser Gly Ser Asp
            180                 185                 190

Ala Lys Gly Asp Arg Tyr Asp Asp Ile Arg Glu Ala Leu Gln Glu Leu
        195                 200                 205

Lys Arg Glu Met Leu Ala Val Arg Gln Ile Ala Pro Arg Ala Leu Leu
210                 215                 220

Ala Pro Ala Gln Leu Ala Xaa Pro Val Ala Ser Pro Thr Thr Thr Thr
225                 230                 235                 240

Ser His Gln Ala Glu Ala Ser Glu Pro Gln Ala Ser Thr Ala Ala Ala
                245                 250                 255

Ala Pro Ser Thr Ala Ser Ser His Gly Ser Lys Ser Ala Glu Arg Gly
            260                 265                 270

Val Val Asn Ala Ser Cys Arg Val Ala Pro Leu Glu Ala Val Asn
        275                 280                 285

Pro Pro Lys Asp Met Val Asp Leu Asn Arg Arg Leu Phe Val Ala Ala
290                 295                 300

Leu Asn Lys Met Glu
305

```
<210> SEQ ID NO 39
<211> LENGTH: 707
<212> TYPE: PRT
<213> ORGANISM: Homo sapiens
```

-continued

```
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid

<400> SEQUENCE: 39

Met Ala Ala Glu Val Tyr Phe Gly Asp Leu Glu Leu Phe Glu Pro Phe
1               5                   10                  15

Asp His Pro Glu Glu Ser Ile Pro Lys Pro Val His Thr Arg Phe Lys
            20                  25                  30

Asp Asp Asp Gly Asp Glu Glu Asp Glu Asn Gly Val Gly Asp Ala Glu
        35                  40                  45

Leu Arg Glu Arg Leu Arg Gln Cys Glu Glu Thr Ile Glu Gln Leu Arg
    50                  55                  60

Ala Glu Asn Gln Glu Leu Lys Arg Lys Leu Asn Ile Leu Thr Arg Pro
65                  70                  75                  80

Ser Gly Ile Leu Val Asn Asp Thr Lys Leu Asp Gly Pro Ile Leu Gln
                85                  90                  95

Ile Leu Phe Met Asn Asn Ala Ile Ser Lys Gln Tyr His Gln Glu Ile
            100                 105                 110

Glu Glu Phe Val Ser Asn Leu Val Lys Arg Phe Glu Glu Gln Gln Lys
        115                 120                 125

Asn Asp Val Glu Lys Thr Ser Phe Asn Leu Leu Pro Gln Pro Ser Ser
130                 135                 140

Ile Val Leu Glu Glu Asp His Lys Val Glu Glu Ser Cys Ala Ile Lys
145                 150                 155                 160

Asn Asn Lys Glu Ala Phe Ser Val Gly Ser Val Leu Tyr Phe Thr
                165                 170                 175

Asn Phe Cys Leu Asp Lys Leu Gly Gln Pro Leu Leu Asn Glu Asn Pro
            180                 185                 190

Gln Leu Ser Glu Gly Trp Glu Ile Pro Lys Tyr His Gln Val Phe Ser
        195                 200                 205

His Ile Val Ser Leu Glu Gly Gln Glu Ile Gln Val Lys Ala Lys Arg
    210                 215                 220

Pro Lys Pro His Cys Phe Asn Cys Gly Ser Glu Glu His Gln Met Lys
225                 230                 235                 240

Asp Cys Pro Met Pro Arg Asn Ala Ala Arg Ile Ser Glu Lys Arg Lys
                245                 250                 255

Glu Tyr Met Asp Ala Cys Gly Glu Ala Asn Asn Gln Asn Phe Gln Gln
            260                 265                 270

Arg Tyr His Ala Glu Glu Val Glu Glu Arg Phe Gly Arg Phe Lys Pro
        275                 280                 285

Gly Val Ile Ser Glu Glu Leu Gln Asp Ala Leu Gly Val Thr Asp Lys
    290                 295                 300

Ser Leu Pro Pro Phe Ile Tyr Arg Met Arg Gln Leu Gly Tyr Pro Pro
305                 310                 315                 320
```

```
Gly Trp Leu Lys Glu Ala Glu Leu Glu Asn Ser Gly Leu Ala Leu Tyr
                325                 330                 335

Asp Gly Lys Asp Gly Thr Asp Gly Glu Thr Glu Val Gly Glu Ile Gln
            340                 345                 350

Gln Asn Lys Ser Val Thr Tyr Asp Leu Ser Lys Leu Val Asn Tyr Pro
        355                 360                 365

Gly Phe Asn Ile Ser Thr Pro Arg Gly Ile Pro Asp Glu Trp Arg Ile
370                 375                 380

Phe Gly Ser Ile Pro Met Gln Ala Cys Gln Lys Asp Val Phe Ala
385                 390                 395                 400

Asn Tyr Leu Thr Ser Asn Phe Gln Ala Pro Gly Val Lys Ser Gly Asn
                405                 410                 415

Lys Arg Xaa Ser Ser His Xaa Ser Pro Gly Ser Pro Lys Lys Gln Lys
            420                 425                 430

Asn Glu Ser Asn Ser Ala Gly Ser Pro Ala Asp Met Glu Leu Asp Ser
        435                 440                 445

Asp Met Glu Val Pro His Gly Ser Gln Ser Ser Glu Ser Phe Gln Phe
    450                 455                 460

Gln Pro Pro Leu Pro Pro Asp Thr Pro Leu Pro Arg Gly Thr Pro
465                 470                 475                 480

Pro Pro Val Phe Thr Pro Leu Pro Lys Gly Xaa Pro Pro Leu Xaa
                485                 490                 495

Pro Ser Asp Ser Pro Gln Thr Arg Thr Ala Ser Gly Ala Val Asp Glu
            500                 505                 510

Asp Ala Leu Thr Leu Glu Glu Leu Glu Glu Gln Arg Arg Ile Trp
        515                 520                 525

Ala Ala Leu Glu Gln Ala Glu Ser Val Asn Ser Asp Ser Asp Val Pro
    530                 535                 540

Val Asp Thr Pro Leu Thr Gly Asn Ser Val Ala Ser Ser Pro Cys Pro
545                 550                 555                 560

Asn Glu Leu Asp Leu Pro Val Pro Glu Gly Lys Thr Ser Glu Lys Gln
                565                 570                 575

Thr Leu Asp Glu Pro Glu Val Pro Glu Ile Phe Thr Lys Lys Ser Glu
            580                 585                 590

Ala Gly His Ala Ser Ser Pro Asp Ser Glu Val Thr Ser Leu Cys Gln
        595                 600                 605

Lys Glu Lys Ala Glu Leu Ala Pro Val Asn Thr Glu Gly Ala Leu Leu
    610                 615                 620

Asp Asn Gly Ser Val Val Pro Asn Cys Asp Ile Ser Asn Gly Gly Ser
625                 630                 635                 640

Gln Lys Leu Phe Pro Ala Asp Thr Ser Pro Ser Thr Ala Thr Lys Ile
                645                 650                 655

His Ser Pro Ile Pro Asp Met Ser Lys Phe Ala Thr Gly Ile Thr Pro
            660                 665                 670

Phe Glu Phe Glu Asn Met Ala Glu Ser Thr Gly Met Tyr Leu Arg Ile
        675                 680                 685

Arg Ser Leu Leu Lys Asn Ser Pro Arg Asn Gln Gln Lys Asn Lys Lys
    690                 695                 700

Ala Ser Glu
705

<210> SEQ ID NO 40
<211> LENGTH: 1242
<212> TYPE: PRT
```

<213> ORGANISM: Homo sapiens
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid

<400> SEQUENCE: 40

```
Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Val Val Leu Gln Leu
        195                 200                 205

Met Asn Ile Arg Arg Cys Gly His Ser Glu Asn Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
    290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Xaa Arg Pro Ala Xaa Val Asp Gly Ser Pro Val Ser Pro Ser Thr Asn
            340                 345                 350

Arg Thr His Ala His Arg His Arg Gly Ser Ala Arg Leu His Pro Pro
```

```
                355                 360                 365
Leu Asn His Ser Arg Ser Ile Pro Met Pro Ala Ser Arg Cys Ser Pro
    370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Ser Phe Arg Ser Val Thr Pro Asp
            435                 440                 445

Ser Leu Gly His Thr Pro Pro Ala Arg Gly Glu Glu Glu Leu Ser Asn
        450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
                500                 505                 510

Ser Ala Ala Asp Leu Asp Asn Arg Phe Arg Lys Arg Thr His Ser Ala
            515                 520                 525

Gly Thr Ser Pro Thr Ile Thr His Gln Lys Thr Pro Ser Gln Ser Ser
        530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
                580                 585                 590

Glu Arg Arg Gly Gly His His Arg Pro Asp Ser Ser Thr Leu His Thr
            595                 600                 605

Asp Asp Gly Tyr Met Pro Met Ser Pro Gly Val Ala Pro Val Pro Ser
        610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
                660                 665                 670

Pro Asp Ile Gly Gly Gly Pro Ser Ser Ser Ser Ser Ser Ser Asn Ala
            675                 680                 685

Val Pro Ser Gly Thr Ser Tyr Gly Lys Leu Trp Thr Asn Gly Val Gly
        690                 695                 700

Gly His His Ser His Val Leu Pro His Pro Lys Pro Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
                740                 745                 750

Pro Glu Asp Pro Gln His Lys Pro Val Leu Ser Tyr Tyr Ser Leu Pro
            755                 760                 765

Arg Ser Phe Lys His Thr Gln Arg Pro Gly Glu Pro Glu Glu Gly Ala
        770                 775                 780
```

```
Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
                805                 810                 815

Gly Gly Gly Tyr Cys Gly Ala Arg Leu Glu Pro Ser Leu Pro His Pro
                820                 825                 830

His His Gln Val Leu Gln Pro His Leu Pro Arg Lys Val Asp Thr Ala
                835                 840                 845

Ala Gln Thr Asn Ser Arg Leu Ala Arg Pro Thr Arg Leu Ser Leu Gly
850                 855                 860

Asp Pro Lys Ala Ser Thr Leu Pro Arg Ala Arg Glu Gln Gln Gln Gln
865                 870                 875                 880

Gln Gln Pro Leu Leu His Pro Pro Glu Pro Lys Ser Pro Gly Glu Tyr
                885                 890                 895

Val Asn Ile Glu Phe Gly Ser Asp Gln Ser Gly Tyr Leu Ser Gly Pro
                900                 905                 910

Val Ala Phe His Ser Ser Pro Ser Val Arg Cys Pro Ser Gln Leu Gln
                915                 920                 925

Pro Ala Pro Arg Glu Glu Glu Thr Gly Thr Glu Tyr Met Lys Met
930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
                980                 985                 990

Gln Met Ser Cys Pro Arg Gln Ser Tyr Val Asp Thr Ser Pro Ala Ala
                995                 1000                1005

Pro Val Ser Tyr Ala Asp Met Arg Thr Gly Ile Ala Ala Glu Glu
    1010                1015                1020

Val Ser Leu Pro Arg Ala Thr Met Ala Ala Ala Ser Ser Ser
    1025                1030                1035

Ala Ala Ser Ala Ser Pro Thr Gly Pro Gln Gly Ala Ala Glu Leu
    1040                1045                1050

Ala Ala His Ser Ser Leu Leu Gly Gly Pro Gln Gly Pro Gly Gly
    1055                1060                1065

Met Ser Ala Phe Thr Arg Val Asn Leu Ser Pro Asn Arg Asn Gln
    1070                1075                1080

Ser Ala Lys Val Ile Arg Ala Asp Pro Gln Gly Cys Arg Arg Arg
    1085                1090                1095

His Ser Ser Glu Thr Phe Ser Ser Thr Pro Ser Ala Thr Arg Val
    1100                1105                1110

Gly Asn Thr Val Pro Phe Gly Ala Gly Ala Ala Val Gly Gly Gly
    1115                1120                1125

Gly Gly Ser Ser Ser Ser Ser Glu Asp Val Lys Arg His Ser Ser
    1130                1135                1140

Ala Ser Phe Glu Asn Val Trp Leu Arg Pro Gly Glu Leu Gly Gly
    1145                1150                1155

Ala Pro Lys Glu Pro Ala Lys Leu Cys Gly Ala Ala Gly Gly Leu
    1160                1165                1170

Glu Asn Gly Leu Asn Tyr Ile Asp Leu Asp Leu Val Lys Asp Phe
    1175                1180                1185
```

-continued

```
Lys Gln Cys Pro Gln Glu Cys Thr Pro Glu Pro Gln Pro Pro Pro
    1190                1195                1200

Pro Pro Pro Pro His Gln Pro Leu Gly Ser Gly Glu Ser Ser Ser
    1205                1210                1215

Thr Arg Arg Ser Ser Glu Asp Leu Ser Ala Tyr Ala Ser Ile Ser
    1220                1225                1230

Phe Gln Lys Gln Pro Glu Asp Arg Gln
    1235                1240

<210> SEQ ID NO 41
<211> LENGTH: 1231
<212> TYPE: PRT
<213> ORGANISM: Mus musculus
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid

<400> SEQUENCE: 41

Met Ala Ser Pro Pro Asp Thr Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Ala His His Asp Gly Ala Gly Gly Gly Cys
        115                 120                 125

Gly Gly Ser Cys Ser Gly Ser Ser Gly Val Gly Glu Ala Gly Glu Asp
    130                 135                 140

Leu Ser Tyr Asp Thr Gly Pro Gly Pro Ala Phe Lys Glu Val Trp Gln
145                 150                 155                 160

Val Ile Leu Lys Pro Lys Gly Leu Gly Gln Thr Lys Asn Leu Ile Gly
                165                 170                 175

Ile Tyr Arg Leu Cys Leu Thr Ser Lys Thr Ile Ser Phe Val Lys Leu
            180                 185                 190

Asn Ser Glu Ala Ala Ala Val Val Leu Gln Leu Met Asn Ile Arg Arg
        195                 200                 205

Cys Gly His Ser Glu Asn Phe Phe Phe Ile Glu Val Gly Arg Ser Ala
    210                 215                 220

Val Thr Gly Pro Gly Glu Phe Trp Met Gln Val Asp Asp Ser Val Val
225                 230                 235                 240

Ala Gln Asn Met His Glu Thr Ile Leu Glu Ala Met Arg Ala Met Ser
                245                 250                 255

Asp Glu Phe Arg Pro Arg Ser Lys Ser Gln Ser Ser Ser Cys Ser
            260                 265                 270
```

-continued

```
Asn Pro Ile Ser Val Pro Leu Arg Arg His His Leu Asn Asn Pro Pro
            275                 280                 285

Pro Ser Gln Val Gly Leu Thr Arg Arg Ser Arg Thr Glu Ser Ile Thr
290                 295                 300

Ala Thr Ser Pro Ala Ser Met Val Gly Lys Pro Gly Ser Phe Arg
305                 310                 315                 320

Val Arg Ala Ser Ser Asp Gly Glu Gly Thr Met Xaa Arg Pro Ala Xaa
                325                 330                 335

Val Asp Gly Ser Pro Val Ser Pro Ser Thr Asn Arg Thr His Ala His
                340                 345                 350

Arg His Arg Gly Ser Ser Arg Leu His Pro Pro Leu Asn His Ser Arg
            355                 360                 365

Ser Ile Pro Met Pro Ser Ser Arg Cys Ser Pro Ser Ala Thr Ser Pro
370                 375                 380

Val Ser Leu Ser Ser Ser Ser Thr Ser Gly His Gly Ser Thr Ser Asp
385                 390                 395                 400

Cys Leu Phe Pro Arg Arg Ser Ser Ala Ser Val Ser Gly Ser Pro Ser
                405                 410                 415

Asp Gly Gly Phe Ile Ser Ser Asp Glu Tyr Gly Ser Ser Pro Cys Asp
                420                 425                 430

Phe Arg Ser Ser Phe Arg Ser Val Thr Pro Asp Ser Leu Gly His Thr
            435                 440                 445

Pro Pro Ala Arg Gly Glu Glu Glu Leu Ser Asn Tyr Ile Cys Met Gly
450                 455                 460

Gly Lys Gly Ala Ser Thr Leu Ala Ala Pro Asn Gly His Tyr Ile Leu
465                 470                 475                 480

Ser Arg Gly Gly Asn Gly His Arg Tyr Ile Pro Gly Ala Asn Leu Gly
                485                 490                 495

Thr Ser Pro Ala Leu Pro Gly Asp Glu Ala Ala Gly Ala Ala Asp Leu
            500                 505                 510

Asp Asn Arg Phe Arg Lys Arg Thr His Ser Ala Gly Thr Ser Pro Thr
            515                 520                 525

Ile Ser His Gln Lys Thr Pro Ser Gln Ser Ser Val Ala Ser Ile Glu
530                 535                 540

Glu Tyr Thr Glu Met Met Pro Ala Ala Tyr Pro Pro Gly Gly Gly Ser
545                 550                 555                 560

Gly Gly Arg Leu Pro Gly Tyr Arg His Ser Ala Phe Val Pro Thr His
                565                 570                 575

Ser Tyr Pro Glu Glu Gly Leu Glu Met His His Leu Glu Arg Arg Gly
            580                 585                 590

Gly His His Arg Pro Asp Thr Ser Asn Leu His Thr Asp Asp Gly Tyr
            595                 600                 605

Met Pro Met Ser Pro Gly Val Ala Pro Val Pro Ser Asn Arg Lys Gly
610                 615                 620

Asn Gly Asp Tyr Met Pro Met Ser Pro Lys Ser Val Ser Ala Pro Gln
625                 630                 635                 640

Gln Ile Ile Asn Pro Ile Arg Arg His Pro Gln Arg Val Asp Pro Asn
                645                 650                 655

Gly Tyr Met Met Met Ser Pro Ser Gly Ser Cys Ser Pro Asp Ile Gly
                660                 665                 670

Gly Gly Ser Ser Ser Ser Ser Ser Ile Ser Ala Ala Pro Ser Gly Ser
            675                 680                 685

Ser Tyr Gly Lys Pro Trp Thr Asn Gly Val Gly Gly His His Thr His
```

```
            690                 695                 700
Ala Leu Pro His Ala Lys Pro Val Glu Ser Gly Gly Lys Leu
705                 710                 715                 720

Leu Pro Cys Thr Gly Asp Tyr Met Asn Met Ser Pro Val Asp Ser
                    725                 730                 735

Asn Thr Ser Ser Pro Ser Glu Cys Tyr Tyr Gly Pro Glu Asp Pro Gln
                740                 745                 750

His Lys Pro Val Leu Ser Tyr Tyr Ser Leu Pro Arg Ser Phe Lys His
            755                 760                 765

Thr Gln Arg Pro Gly Glu Pro Glu Gly Ala Arg His Gln His Leu
        770                 775                 780

Arg Leu Ser Ser Ser Gly Arg Leu Arg Tyr Thr Ala Thr Ala Glu
785                 790                 795                 800

Asp Ser Ser Ser Thr Ser Ser Asp Ser Leu Gly Gly Gly Tyr Cys
                805                 810                 815

Gly Ala Arg Pro Glu Ser Ser Leu Thr His Pro His His His Val Leu
                820                 825                 830

Gln Pro His Leu Pro Arg Lys Val Asp Thr Ala Ala Gln Thr Asn Ser
            835                 840                 845

Arg Leu Ala Arg Pro Thr Arg Leu Ser Leu Gly Asp Pro Lys Ala Ser
850                 855                 860

Thr Leu Pro Arg Val Arg Glu Gln Gln Gln Gln Gln Ser Ser Leu
865                 870                 875                 880

His Pro Pro Glu Pro Lys Ser Pro Gly Glu Tyr Val Asn Ile Glu Phe
                885                 890                 895

Gly Ser Gly Gln Pro Gly Tyr Leu Ala Gly Pro Ala Thr Ser Arg Ser
                900                 905                 910

Ser Pro Ser Val Arg Cys Pro Pro Gln Leu His Pro Ala Pro Arg Glu
            915                 920                 925

Glu Thr Gly Ser Glu Glu Tyr Met Asn Met Asp Leu Gly Pro Gly Arg
930                 935                 940

Arg Ala Thr Trp Gln Glu Ser Gly Gly Val Glu Leu Gly Arg Ile Gly
945                 950                 955                 960

Pro Ala Pro Pro Gly Ser Ala Thr Val Cys Arg Pro Thr Arg Ser Val
                965                 970                 975

Pro Asn Ser Arg Gly Asp Tyr Met Thr Met Gln Ile Gly Cys Pro Arg
            980                 985                 990

Gln Ser Tyr Val Asp Thr Ser Pro Val Ala Pro Val Ser Tyr Ala Asp
        995                 1000                1005

Met Arg Thr Gly Ile Ala Ala Glu Lys Ala Ser Leu Pro Arg Pro
1010                1015                1020

Thr Gly Ala Ala Pro Pro Ser Ser Thr Ala Ser Ser Ser Val
        1025                1030                1035

Thr Pro Gln Gly Ala Thr Ala Glu Gln Ala Thr His Ser Ser Leu
    1040                1045                1050

Leu Gly Gly Pro Gln Gly Pro Gly Gly Met Ser Ala Phe Thr Arg
    1055                1060                1065

Val Asn Leu Ser Pro Asn His Asn Gln Ser Ala Lys Val Ile Arg
    1070                1075                1080

Ala Asp Thr Gln Gly Cys Arg Arg Arg His Ser Ser Glu Thr Phe
    1085                1090                1095

Ser Ala Pro Thr Arg Ala Gly Asn Thr Val Pro Phe Gly Ala Gly
    1100                1105                1110
```

```
Ala Ala Val Gly Gly Ser Gly Gly Gly Gly Gly Ser Glu
    1115                1120                1125

Asp Val Lys Arg His Ser Ser Ala Ser Phe Glu Asn Val Trp Leu
    1130                1135                1140

Arg Pro Gly Asp Leu Gly Gly Val Ser Lys Glu Ser Ala Pro Val
    1145                1150                1155

Cys Gly Ala Ala Gly Gly Leu Glu Lys Ser Leu Asn Tyr Ile Asp
    1160                1165                1170

Leu Asp Leu Ala Lys Glu Arg Ser Gln Asp Cys Pro Ser Gln Gln
    1175                1180                1185

Gln Ser Leu Pro Pro Pro Pro His Gln Pro Leu Gly Ser Asn
    1190                1195                1200

Glu Gly Asn Ser Pro Arg Arg Ser Ser Glu Asp Leu Ser Asn Tyr
    1205                1210                1215

Ala Ser Ile Ser Phe Gln Lys Gln Pro Glu Asp Arg Gln
    1220                1225                1230

<210> SEQ ID NO 42
<211> LENGTH: 572
<212> TYPE: PRT
<213> ORGANISM: Homo sapiens
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid

<400> SEQUENCE: 42

Met Ser Tyr Gln Gly Lys Lys Asn Ile Pro Arg Ile Thr Ser Asp Arg
1               5                   10                  15

Leu Leu Ile Lys Gly Gly Lys Ile Val Asn Asp Asp Gln Ser Phe Tyr
            20                  25                  30

Ala Asp Ile Tyr Met Glu Asp Gly Leu Ile Lys Gln Ile Gly Glu Asn
        35                  40                  45

Leu Ile Val Pro Gly Gly Val Lys Thr Ile Glu Ala His Ser Arg Met
    50                  55                  60

Val Ile Pro Gly Gly Ile Asp Val His Thr Arg Phe Gln Met Pro Asp
65                  70                  75                  80

Gln Gly Met Thr Ser Ala Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Gly Thr Ser Leu Leu Ala Ala Phe Asp Gln Trp Arg Glu Trp Ala Asp
        115                 120                 125

Ser Lys Ser Cys Cys Asp Tyr Ser Leu His Val Asp Ile Ser Glu Trp
    130                 135                 140

His Lys Gly Ile Gln Glu Glu Met Glu Ala Leu Val Lys Asp His Gly
145                 150                 155                 160

Val Asn Ser Phe Leu Val Tyr Met Ala Phe Lys Asp Arg Phe Gln Leu
                165                 170                 175

Thr Asp Cys Gln Ile Tyr Glu Val Leu Ser Val Ile Arg Asp Ile Gly
```

```
                180              185              190
Ala Ile Ala Gln Val His Ala Glu Asn Gly Asp Ile Ile Ala Glu Glu
            195                  200              205
Gln Gln Arg Ile Leu Asp Leu Gly Ile Thr Gly Pro Glu Gly His Val
            210              215              220
Leu Ser Arg Pro Glu Val Glu Ala Glu Val Asn Arg Ala Ile
225              230              235              240
Thr Ile Ala Asn Gln Thr Asn Cys Pro Leu Tyr Ile Thr Lys Val Met
                245              250              255
Ser Lys Ser Ser Ala Glu Val Ile Ala Gln Ala Arg Lys Lys Gly Thr
            260              265              270
Val Val Tyr Gly Glu Pro Ile Thr Ala Ser Leu Gly Thr Asp Gly Ser
        275              280              285
His Tyr Trp Ser Lys Asn Trp Ala Lys Ala Ala Phe Val Thr Ser
    290              295              300
Pro Pro Leu Ser Pro Asp Pro Thr Thr Pro Asp Phe Leu Asn Ser Leu
305              310              315              320
Leu Ser Cys Gly Asp Leu Gln Val Thr Gly Ser Ala His Cys Thr Phe
                325              330              335
Asn Thr Ala Gln Lys Ala Val Gly Lys Asp Asn Phe Thr Leu Ile Pro
            340              345              350
Glu Gly Thr Asn Gly Thr Glu Glu Arg Met Ser Val Ile Trp Asp Lys
            355              360              365
Ala Val Val Thr Gly Lys Met Asp Glu Asn Gln Phe Val Ala Val Thr
        370              375              380
Ser Thr Asn Ala Ala Lys Val Phe Asn Leu Tyr Pro Arg Lys Gly Arg
385              390              395              400
Ile Ala Val Gly Ser Asp Ala Asp Leu Val Ile Trp Asp Pro Asp Ser
                405              410              415
Val Lys Thr Ile Ser Ala Lys Thr His Asn Ser Ser Leu Glu Tyr Asn
            420              425              430
Ile Phe Glu Gly Met Glu Cys Arg Gly Ser Pro Leu Val Val Ile Ser
            435              440              445
Gln Gly Lys Ile Val Leu Glu Asp Gly Thr Leu His Val Thr Glu Gly
        450              455              460
Ser Gly Arg Tyr Ile Pro Arg Lys Pro Phe Pro Asp Phe Val Tyr Lys
465              470              475              480
Arg Ile Lys Ala Arg Ser Arg Leu Ala Glu Leu Arg Gly Val Pro Arg
            485              490              495
Gly Leu Tyr Asp Gly Pro Val Cys Glu Val Ser Val Xaa Pro Lys Thr
            500              505              510
Val Xaa Pro Ala Ser Xaa Ala Lys Thr Ser Pro Ala Lys Gln Gln Ala
        515              520              525
Pro Pro Val Arg Asn Leu His Gln Ser Gly Phe Ser Leu Ser Gly Ala
            530              535              540
Gln Ile Asp Asp Asn Ile Pro Arg Arg Thr Thr Gln Arg Ile Val Ala
545              550              555              560
Pro Pro Gly Gly Arg Ala Asn Ile Thr Ser Leu Gly
            565              570

<210> SEQ ID NO 43
<211> LENGTH: 1129
<212> TYPE: PRT
<213> ORGANISM: herpes virus
```

```
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (261)..(261)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 43

Met Ala Pro Pro Gly Met Arg Leu Arg Ser Gly Arg Ser Thr Gly Ala
1               5                   10                  15

Pro Leu Thr Arg Gly Ser Cys Arg Lys Arg Asn Arg Ser Pro Glu Arg
            20                  25                  30

Cys Asp Leu Gly Asp Asp Leu His Leu Gln Pro Arg Arg Lys His Val
        35                  40                  45

Ala Asp Ser Val Asp Gly Arg Glu Cys Gly Pro His Thr Leu Pro Ile
    50                  55                  60

Pro Gly Ser Pro Thr Val Phe Thr Ser Gly Leu Pro Ala Phe Val Ser
65                  70                  75                  80

Ser Pro Thr Leu Pro Val Ala Pro Ile Pro Ser Pro Ala Pro Ala Thr
                85                  90                  95

Pro Leu Pro Pro Pro Ala Leu Leu Pro Pro Val Thr Thr Ser Ser Ser
            100                 105                 110

Pro Ile Pro Pro Xaa His Pro Val Xaa Pro Gly Thr Xaa Asp Thr His
        115                 120                 125

Ser Pro Ser Pro Ala Leu Pro Pro Thr Gln Ser Pro Glu Ser Ser Gln
    130                 135                 140

Arg Pro Pro Leu Ser Ser Pro Thr Gly Arg Pro Asp Ser Ser Thr Pro
```

```
                145                 150                 155                 160
         Met Arg Pro Pro Pro Xaa Gln Gln Thr Xaa Pro Pro His Ser Pro Thr
                         165                 170                 175

Thr Pro Pro Pro Glu Pro Pro Ser Lys Xaa Ser Pro Asp Xaa Leu Ala
                         180                 185                 190

Pro Xaa Thr Leu Arg Ser Leu Arg Lys Arg Arg Leu Ser Ser Pro Gln
                         195                 200                 205

Gly Pro Ser Thr Leu Asn Pro Ile Cys Gln Xaa Pro Pro Val Ser Pro
                         210                 215                 220

Pro Arg Cys Asp Phe Ala Asn Arg Ser Val Tyr Pro Pro Trp Ala Thr
         225                 230                 235                 240

Glu Ser Pro Ile Tyr Val Gly Ser Ser Xaa Asp Gly Asp Thr Pro Pro
                         245                 250                 255

Arg Gln Pro Pro Xaa Ser Pro Ile Xaa Ile Gly Ser Ser Ser Pro Ser
                         260                 265                 270

Glu Gly Ser Trp Gly Asp Asp Thr Ala Met Leu Val Leu Leu Ala Glu
                         275                 280                 285

Ile Ala Glu Glu Ala Ser Lys Asn Glu Lys Glu Cys Ser Glu Asn Asn
         290                 295                 300

Gln Ala Gly Glu Asp Asn Gly Asp Asn Glu Ile Ser Lys Glu Ser Gln
         305                 310                 315                 320

Val Asp Lys Asp Asp Asn Asp Asn Lys Asp Asp Glu Glu Glu Gln Glu
                         325                 330                 335

Thr Asp Glu Glu Asp Glu Glu Asp Glu Asp Asp Glu Glu Asp
                         340                 345                 350

Asp Glu Glu Asp Asp Glu Glu Asp Asp Glu Asp Asp Glu Glu Asp
                         355                 360                 365

Asp Glu Glu Asp Glu Glu Asp Glu Glu Asp Glu Glu Glu
                         370                 375                 380

Asp Glu Glu Glu Glu Asp Glu Glu Asp Asp Asp Glu Asp Asn
         385                 390                 395                 400

Glu Asp Glu Glu Asp Asp Glu Glu Asp Lys Lys Glu Asp Glu Glu
                         405                 410                 415

Asp Gly Gly Asp Gly Asn Lys Thr Leu Ser Ile Gln Ser Ser Gln Gln
                         420                 425                 430

Gln Gln Glu Pro Gln Gln Glu Pro Gln Gln Glu Pro Gln Gln
                         435                 440                 445

Gln Glu Pro Gln Gln Glu Pro Gln Gln Glu Pro Gln Gln Gln
         450                 455                 460

Glu Pro Gln Gln Glu Pro Gln Gln Arg Glu Pro Gln Gln Arg Glu
         465                 470                 475                 480

Pro Gln Gln Arg Glu Pro Gln Gln Arg Glu Pro Gln Gln Arg Glu Pro
                         485                 490                 495

Gln Gln Arg Glu Pro Gln Gln Arg Glu Pro Gln Gln Arg Glu Pro Gln
                         500                 505                 510

Gln Arg Glu Pro Gln Gln Arg Glu Pro Gln Gln Arg Glu Pro Gln Gln
                         515                 520                 525

Arg Glu Pro Gln Gln Glu Pro Gln Gln Glu Pro Gln Gln Gln
                         530                 535                 540

Glu Pro Gln Gln Glu Pro Gln Gln Glu Pro Gln Gln Glu
         545                 550                 555                 560

Pro Gln Gln Glu Pro Gln Gln Glu Pro Gln Gln Glu Pro
                         565                 570                 575
```

```
Gln Gln Gln Glu Pro Gln Gln Glu Pro Gln Gln Glu Pro Gln
            580                 585                 590

Gln Gln Asp Glu Gln Gln Asp Glu Gln Gln Asp Glu Gln Gln
            595                 600                 605

Gln Asp Glu Gln Gln Asp Glu Gln Gln Asp Glu Gln Gln Gln
            610                 615                 620

Asp Glu Gln Gln Asp Glu Gln Gln Asp Glu Gln Gln Gln Gln
625                 630                 635                 640

Asp Glu Gln Gln Gln Asp Glu Gln Gln Glu Glu Gln Gln Glu
            645                 650                 655

Gln Gln Glu Gln Gln Gln Asp Glu Gln Gln Asp Glu Gln Gln
            660                 665                 670

Gln Asp Glu Gln Gln Asp Glu Gln Gln Gln Asp Glu Gln Gln
            675                 680                 685

Gln Asp Glu Gln Gln Gln Asp Glu Gln Gln Gln Glu Glu Gln
            690                 695                 700

Glu Gln Gln Glu Glu Glu Gln Gln Glu Glu Gln Gln Gln Glu
705                 710                 715                 720

Glu Gln Glu Gln Glu Leu Glu Glu Gln Glu Glu Leu Glu Gln
            725                 730                 735

Glu Gln Glu Leu Glu Glu Gln Gln Glu Leu Glu Glu Gln Gln
            740                 745                 750

Glu Leu Glu Glu Gln Gln Glu Leu Glu Glu Gln Gln Glu Leu
            755                 760                 765

Glu Glu Gln Gln Glu Leu Glu Glu Gln Gln Glu Leu Glu Glu
            770                 775                 780

Gln Glu Gln Glu Leu Glu Glu Gln Glu Glu Leu Glu Glu Gln
785                 790                 795                 800

Gln Glu Leu Glu Glu Gln Gln Glu Leu Glu Glu Gln Gln Glu
            805                 810                 815

Leu Glu Glu Gln Glu Glu Gln Glu Leu Glu Glu Val Glu Gln
            820                 825                 830

Glu Gln Glu Gln Glu Glu Gln Leu Glu Glu Val Glu Gln Glu
            835                 840                 845

Gln Glu Gln Glu Gln Glu Glu Gln Glu Leu Glu Glu Val Glu Glu
            850                 855                 860

Gln Glu Glu Gln Glu Leu Glu Glu Val Glu Glu Gln Glu Glu
865                 870                 875                 880

Leu Glu Glu Val Glu Glu Gln Gln Gln Gly Val Glu Gln Glu
            885                 890                 895

Gln Glu Thr Val Glu Glu Pro Ile Ile Leu His Gly Ser Ser Glu
            900                 905                 910

Asp Glu Met Glu Val Asp Tyr Pro Val Val Ser Thr His Glu Gln Ile
            915                 920                 925

Ala Ser Ser Pro Pro Gly Asp Asn Thr Pro Asp Asp Pro Gln Pro
            930                 935                 940

Gly Pro Ser Arg Glu Tyr Arg Tyr Val Leu Arg Thr Ser Pro Pro His
945                 950                 955                 960

Arg Pro Gly Val Arg Met Arg Arg Val Pro Val Thr His Pro Lys Lys
            965                 970                 975

Pro His Pro Arg Tyr Gln Gln Pro Pro Val Pro Tyr Arg Gln Ile Asp
            980                 985                 990
```

```
Asp Cys Pro Ala Lys Ala Arg Pro Gln His Ile Phe Tyr Arg Arg Phe
        995                 1000                1005

Leu Gly Lys Asp Gly Arg Arg Asp Pro Lys Cys Gln Trp Lys Phe
    1010                1015                1020

Ala Val Ile Phe Trp Gly Asn Asp Pro Tyr Gly Leu Lys Lys Leu
    1025                1030                1035

Ser Gln Ala Phe Gln Phe Gly Val Lys Ala Gly Pro Val Ser
    1040                1045                1050

Cys Leu Pro His Pro Gly Pro Asp Gln Ser Pro Ile Thr Tyr Cys
    1055                1060                1065

Val Tyr Val Tyr Cys Gln Asn Lys Asp Thr Ser Lys Lys Val Gln
    1070                1075                1080

Met Ala Arg Leu Ala Trp Glu Ala Ser His Pro Leu Ala Gly Asn
    1085                1090                1095

Leu Gln Ser Ser Ile Val Lys Phe Lys Lys Pro Leu Pro Leu Thr
    1100                1105                1110

Gln Pro Gly Glu Asn Gln Gly Pro Gly Asp Ser Pro Gln Glu Met
    1115                1120                1125

Thr

<210> SEQ ID NO 44
<211> LENGTH: 483
<212> TYPE: PRT
<213> ORGANISM: Homo sapiens
<220> FEATURE:
<221> NAME/KEY: misc_feature
<222> LOCATION: (279)..(279)
<223> OTHER INFORMATION: Xaa can be any naturally occurring amino acid

<400> SEQUENCE: 44

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Ser Gly Gly Pro
65                  70                  75                  80

Gly Ala Gly Thr Ser Phe Pro Pro Gly Val Lys Leu Gly Arg Asp
            85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
            115                 120                 125

Ser Phe Gly Val Val Tyr Gln Ala Arg Leu Ala Glu Thr Arg Glu Leu
            130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
            195                 200                 205
```

Phe Thr Lys Ala Lys Leu Thr Ile Pro Ile Leu Tyr Val Lys Val Tyr
            210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
            260                 265                 270

Gly Glu Pro Asn Val Ser Xaa Ile Cys Ser Arg Tyr Tyr Arg Ala Pro
        275                 280                 285

Glu Leu Ile Phe Gly Ala Thr Asp Tyr Thr Ser Ser Ile Asp Val Trp
    290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
            340                 345                 350

Glu Phe Lys Phe Pro Gln Ile Lys Ala His Pro Trp Thr Lys Val Phe
        355                 360                 365

Lys Ser Arg Thr Pro Pro Glu Ala Ile Ala Leu Cys Ser Ser Leu Leu
    370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
            420                 425                 430

Gln Pro Ser Leu Asn Ala Ile Leu Ile Pro Pro His Leu Arg Ser Pro
        435                 440                 445

Ala Gly Thr Thr Thr Leu Thr Pro Ser Ser Gln Ala Leu Thr Glu Thr
    450                 455                 460

Pro Thr Ser Ser Asp Trp Gln Ser Thr Asp Ala Thr Pro Thr Leu Thr
465                 470                 475                 480

Asn Ser Ser

<210> SEQ ID NO 45
<211> LENGTH: 443
<212> TYPE: PRT
<213> ORGANISM: Homo sapiens
<220> FEATURE:
<221> NAME/KEY: misc_feature
<222> LOCATION: (216)..(216)
<223> OTHER INFORMATION: Xaa can be any naturally occurring amino acid

<400> SEQUENCE: 45

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu

```
            65                  70                  75                  80
Leu Val Ala Ile Lys Lys Val Leu Gln Asp Lys Arg Phe Lys Asn Arg
                85                  90                  95
Glu Leu Gln Ile Met Arg Lys Leu Asp His Cys Asn Ile Val Arg Leu
            100                 105                 110
Arg Tyr Phe Phe Tyr Ser Ser Gly Glu Lys Lys Asp Glu Val Tyr Leu
            115                 120                 125
Asn Leu Val Leu Asp Tyr Val Pro Glu Thr Val Tyr Arg Val Ala Arg
            130                 135                 140
His Tyr Ser Arg Ala Lys Gln Thr Leu Pro Val Ile Tyr Val Lys Leu
145                 150                 155                 160
Tyr Met Tyr Gln Leu Phe Arg Ser Leu Ala Tyr Ile His Ser Phe Gly
                165                 170                 175
Ile Cys His Arg Asp Ile Lys Pro Gln Asn Leu Leu Leu Asp Pro Asp
            180                 185                 190
Thr Ala Val Leu Lys Leu Cys Asp Phe Gly Ser Ala Lys Gln Leu Val
            195                 200                 205
Arg Gly Glu Pro Asn Val Ser Xaa Ile Cys Ser Arg Tyr Tyr Arg Ala
210                 215                 220
Pro Glu Leu Ile Phe Gly Ala Thr Asp Tyr Thr Ser Ser Ile Asp Val
225                 230                 235                 240
Trp Ser Ala Gly Cys Val Leu Ala Glu Leu Leu Leu Gly Gln Pro Ile
                245                 250                 255
Phe Pro Gly Asp Ser Gly Val Asp Gln Leu Val Glu Ile Ile Lys Val
            260                 265                 270
Leu Gly Thr Pro Thr Arg Glu Gln Ile Arg Glu Met Asn Pro Asn Tyr
            275                 280                 285
Thr Glu Phe Lys Phe Pro Gln Ile Lys Ala His Pro Trp Thr Lys Asp
            290                 295                 300
Ser Ser Gly Thr Gly His Phe Thr Ser Gly Val Arg Val Phe Arg Pro
305                 310                 315                 320
Arg Thr Pro Pro Glu Ala Ile Ala Leu Cys Ser Arg Leu Leu Glu Tyr
                325                 330                 335
Thr Pro Thr Ala Arg Leu Thr Pro Leu Glu Ala Cys Ala His Ser Phe
            340                 345                 350
Phe Asp Glu Leu Arg Asp Pro Asn Val Lys Leu Pro Asn Gly Arg Asp
            355                 360                 365
Thr Pro Ala Leu Phe Asn Phe Thr Thr Gln Glu Leu Ser Ser Asn Pro
            370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                405                 410                 415
Asp Arg Gly Gln Thr Asn Asn Ala Ala Ser Ala Ser Ala Ser Asn Ser
            420                 425                 430
Thr Ser Asx Ser Glu Gln Glu Asn Cys Glu Ser
            435                 440

<210> SEQ ID NO 46
<211> LENGTH: 23
<212> TYPE: PRT
<213> ORGANISM: artificial sequence
<220> FEATURE:
<223> OTHER INFORMATION: synthetic
<220> FEATURE:
```

```
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 46

Ala Gln Arg Asp Ser His Leu Gly Pro His Arg Xaa Thr Pro Glu Xaa
1               5                   10                  15

Arg Ala Ala Val Gln Glu Leu
            20

<210> SEQ ID NO 47
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid

<400> SEQUENCE: 47

Gln Glu Leu Glu Met Gln Ala Arg Ala His Gly Leu Xaa Leu Ile Pro
1               5                   10                  15

Ser Thr Gly Leu Cys Ser Pro Asp Leu Val Asn Arg Ile Ile
            20                  25                  30

<210> SEQ ID NO 48
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 48

Asn Tyr Ser Tyr Pro Tyr Ala Xaa Pro Gln Thr Xaa Pro Trp Gln Xaa
1               5                   10                  15

Pro Cys Val Ser Pro Lys Thr Thr Asp Pro Glu Glu Gly
            20                  25

<210> SEQ ID NO 49
<211> LENGTH: 31
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
```

```
<220> FEATURE:
<221> NAME/KEY: misc_feature
<222> LOCATION: (13)..(13)
<223> OTHER INFORMATION: Xaa can be any naturally occurring amino acid

<400> SEQUENCE: 49

Asp Leu Pro Asp Xaa Pro Gly Gln Xaa Met Pro Pro Xaa Arg Ser Lys
1               5                   10                  15

Thr Pro Pro Pro Pro Gln Thr Ala Gln Thr Lys Arg Glu Val
            20                  25                  30

<210> SEQ ID NO 50
<211> LENGTH: 25
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 50

Pro Glu Pro Pro Ser Lys Xaa Ser Pro Asp Xaa Leu Ala Pro Xaa Thr
1               5                   10                  15

Leu Arg Ser Leu Arg Lys Arg Arg Leu
            20                  25

<210> SEQ ID NO 51
<211> LENGTH: 34
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 51

Ala Thr Gln Gly Tyr Arg Tyr Pro Arg Pro Ala Xaa Val Pro Pro Xaa
1               5                   10                  15

Pro Ser Leu Xaa Arg His Ser Xaa Pro His Gln Ser Glu Asp Glu Glu
            20                  25                  30

Glu Pro

<210> SEQ ID NO 52
<211> LENGTH: 29
<212> TYPE: PRT
```

```
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 52

Gly Tyr Arg Tyr Pro Arg Pro Ala Xaa Val Pro Pro Xaa Pro Ser Leu
1               5                   10                  15

Xaa Arg His Ser Xaa Pro His Gln Ser Glu Asp Glu Glu
            20                  25

<210> SEQ ID NO 53
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 53

Ser Gly Ser Ser Asp Ser Arg Xaa His Gln Asn Ser Pro Thr Glu Leu
1               5                   10                  15

Asn Lys Asp Arg
            20

<210> SEQ ID NO 54
<211> LENGTH: 17
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Gly Ser Ser Asp Ser Arg Xaa His Gln Asn Ser Pro Thr Glu Leu Asn
1               5                   10                  15

Lys

<210> SEQ ID NO 55
<211> LENGTH: 22
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 55

Asn Lys Asp Arg Thr Xaa Arg Asp Ser Ser Pro Val Met Arg Ser Ser
1               5                   10                  15

Ser Thr Leu Pro Val Pro
            20

<210> SEQ ID NO 56
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 56

Leu Asn Lys Asp Arg Thr Xaa Arg Asp Ser Ser Pro Val Met Arg Ser
1               5                   10                  15

Ser Ser Thr Leu Pro
            20

<210> SEQ ID NO 57
<211> LENGTH: 24
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

Pro Val Pro Gln Pro Ser Xaa Ala Pro Pro Thr Pro Thr Arg Leu Thr
1               5                   10                  15

Gly Ala Asn Ser Asp Met Glu Glu
            20

<210> SEQ ID NO 58
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 58

Val Pro Gln Pro Ser Xaa Ala Pro Pro Thr Pro Thr Arg Leu Thr Gly
1               5                   10                  15

Ala Asn Ser Asp Met
            20

<210> SEQ ID NO 59
<211> LENGTH: 25
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
```

<400> SEQUENCE: 59

Gln Ser Met Asp Ser Glu Glu Pro Asp Xaa Arg Gly Gly Ser Pro Gln
1               5                   10                  15

Met Asp Asp Ile Lys Val Phe Gln Asn
            20                  25

<210> SEQ ID NO 60
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 60

Met Asp Ser Glu Glu Pro Asp Xaa Arg Gly Gly Ser Pro Gln Met Asp
1               5                   10                  15

Asp Ile Lys Val Phe
            20

<210> SEQ ID NO 61
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 61

Ala Ser Gly Ser Thr Ser Xaa Pro Ala Pro Xaa Arg Thr Ala Xaa Phe
1               5                   10                  15

Ser Glu Ser Arg Ala Asp Glu Val Ala Pro Ala Lys Lys
            20                  25

<210> SEQ ID NO 62
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 62

```
Asn Ala Ser Gly Ser Thr Ser Xaa Pro Ala Pro Xaa Arg Thr Ala Xaa
1               5                   10                  15

Phe Ser Glu Ser Arg Ala Asp Glu Val Ala Pro Ala Lys
            20                  25
```

<210> SEQ ID NO 63
<211> LENGTH: 28
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 63

```
Tyr Ala Leu Ala Pro Ala Thr Xaa Ala Asn Asp Xaa Glu Gln Gln Ser
1               5                   10                  15

Leu Ser Ser Asp Ala Asp Thr Leu Ser Leu Thr Asp
            20                  25
```

<210> SEQ ID NO 64
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 64

```
Ala Leu Ala Pro Ala Thr Xaa Ala Asn Asp Xaa Glu Gln Gln Ser Leu
1               5                   10                  15

Ser Ser Asp Ala Asp
            20
```

<210> SEQ ID NO 65
<211> LENGTH: 38
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 65

```
Ala Val Ser His Trp Gln Gln Gln Ser Tyr Leu Asp Xaa Gly Ile His
1               5                   10                  15
```

```
Xaa Gly Ala Thr Xaa Thr Ala Pro Ser Leu Ser Gly Lys Gly Asn Pro
            20                  25                  30

Glu Glu Glu Asp Val Asp
        35

<210> SEQ ID NO 66
<211> LENGTH: 31
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 66

His Trp Gln Gln Gln Ser Tyr Leu Asp Xaa Gly Ile His Xaa Gly Ala
1               5                   10                  15

Thr Xaa Thr Ala Pro Ser Leu Ser Gly Lys Gly Asn Pro Glu Glu
            20                  25                  30

<210> SEQ ID NO 67
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 67

Arg Thr Lys Ser Ser Arg Leu Gln Gly Xaa Ser Leu Ser Ser Glu Ser
1               5                   10                  15

Ala Arg His Lys
        20

<210> SEQ ID NO 68
<211> LENGTH: 22
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 68

His Lys Ala Val Glu Phe Ser Xaa Gly Ala Lys Ser Pro Ser Lys Ser
1               5                   10                  15

Gly Ala Gln Thr Pro Lys
        20

<210> SEQ ID NO 69
<211> LENGTH: 67
<212> TYPE: PRT
<213> ORGANISM: artificial sequence
```

```
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 69

Met Phe Ser Arg Cys Thr Ser Val Xaa Ser Leu Asp Ser Phe Glu Ser
1               5                   10                  15

Arg Xaa Ile Ala Ser Ser Val Gln Xaa Glu Pro Cys Xaa Gly Met Val
            20                  25                  30

Xaa Gly Ile Ile Ser Pro Ser Asp Leu Pro Asp Xaa Pro Gly Gln Xaa
        35                  40                  45

Met Pro Pro Xaa Arg Ser Lys Thr Pro Pro Pro Pro Gln Thr Ala
    50                  55                  60

Gln Thr Lys
65

<210> SEQ ID NO 70
<211> LENGTH: 23
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 70

His Gly Arg Tyr Val Pro Pro Ser Xaa Thr Asp Arg Ser Pro Tyr Glu
1               5                   10                  15

Lys Val Ser Ala Gly Asn Gly
            20

<210> SEQ ID NO 71
<211> LENGTH: 19
<212> TYPE: PRT
<213> ORGANISM: artificial sequence
<220> FEATURE:
<223> OTHER INFORMATION: synthetic
```

```
<220> FEATURE:
<221> NAME/KEY: misc_feature
<222> LOCATION: (7)..(7)
<223> OTHER INFORMATION: Xaa can be any naturally occurring amino acid

<400> SEQUENCE: 71

Arg Tyr Val Pro Pro Ser Xaa Thr Asp Arg Ser Pro Tyr Glu Lys Val
1               5                   10                  15

Ser Ala Gly

<210> SEQ ID NO 72
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 72

Met Asp Pro Lys Ala Ala Glu Glu Glu Glu Glu Glu Glu Glu Glu Val
1               5                   10                  15

Asp Leu Ala Cys Xaa Pro Thr Asp Val Arg Asp Val Asp Ile
            20                  25                  30

<210> SEQ ID NO 73
<211> LENGTH: 18
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 73

Glu Glu Glu Glu Glu Val Asp Leu Ala Cys Xaa Pro Thr Asp Val Arg
1               5                   10                  15

Asp Val

<210> SEQ ID NO 74
<211> LENGTH: 31
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 74

Gln Thr Val Pro Glu Met Pro Gly Glu Xaa Pro Pro Leu Xaa Pro Ile
1               5                   10                  15

Asp Met Glu Xaa Gln Glu Arg Ile Lys Ala Glu Arg Lys Arg Met
            20                  25                  30
```

```
<210> SEQ ID NO 75
<211> LENGTH: 27
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 75

Val Pro Glu Met Pro Gly Glu Xaa Pro Pro Leu Xaa Pro Ile Asp Met
1               5                   10                  15

Glu Xaa Gln Glu Arg Ile Lys Ala Glu Arg Lys
            20                  25

<210> SEQ ID NO 76
<211> LENGTH: 27
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 76

Gln Thr Val Pro Glu Ala Arg Ser Arg Asp Ala Xaa Pro Pro Val Ser
1               5                   10                  15

Pro Ile Asn Met Glu Asp Gln Glu Arg Ile Lys
            20                  25

<210> SEQ ID NO 77
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 77

Pro Glu Ala Arg Ser Arg Asp Ala Xaa Pro Pro Val Ser Pro Ile Asn
1               5                   10                  15

Met Glu Asp Gln
            20

<210> SEQ ID NO 78
<211> LENGTH: 28
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid
```

```
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 78

Pro Asp Val Pro Ser Phe Gly Asp Xaa Pro Pro Leu Xaa Pro Ile Asp
1               5                   10                  15

Met Asp Xaa Gln Glu Arg Ile Lys Ala Glu Arg Lys
            20                  25

<210> SEQ ID NO 79
<211> LENGTH: 25
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 79

Val Pro Ser Phe Gly Asp Xaa Pro Pro Leu Xaa Pro Ile Asp Met Asp
1               5                   10                  15

Xaa Gln Glu Arg Ile Lys Ala Glu Arg
            20                  25

<210> SEQ ID NO 80
<211> LENGTH: 23
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 80

Asp Ile Trp Lys Lys Phe Glu Leu Leu Pro Xaa Pro Pro Leu Ser Pro
1               5                   10                  15

Ser Arg Arg Ser Gly Leu Cys
            20

<210> SEQ ID NO 81
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 81
```

Trp Lys Lys Phe Glu Leu Leu Pro Xaa Pro Pro Leu Ser Pro Ser Arg
1               5                   10                  15

Arg Ser Gly

<210> SEQ ID NO 82
<211> LENGTH: 27
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 82

Phe Ser Pro Ser Ser Asp Ser Leu Leu Ser Xaa Thr Glu Ser Xaa Pro
1               5                   10                  15

Gln Gly Ser Pro Glu Pro Leu Val Leu His Glu
            20                  25

<210> SEQ ID NO 83
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 83

Leu Ser Pro Ser Arg Arg Xaa Gly Leu Cys Ser Pro Ser Tyr Val Ala
1               5                   10                  15

Val Thr Pro Phe
            20

<210> SEQ ID NO 84
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 84

Gln Ala Pro Gly Lys Arg Xaa Glu Ser Gly Ser Pro Ser Ala Gly Gly
1               5                   10                  15

His Ser Lys

<210> SEQ ID NO 85
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

```
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 85

Asn Tyr Ser Tyr Pro Tyr Ala Xaa Pro Gln Thr Xaa Pro Trp Gln Xaa
1               5                   10                  15

Pro Cys Val Ser Pro Lys Thr Thr Asp Pro Glu Glu Gly
            20                  25

<210> SEQ ID NO 86
<211> LENGTH: 31
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 86

Phe Pro Arg Gly Leu Gly Ala Cys Thr Leu Leu Gly Xaa Pro Arg His
1               5                   10                  15

Xaa Pro Ser Thr Ser Pro Arg Ala Ser Val Thr Glu Glu Ser Trp
            20                  25                  30

<210> SEQ ID NO 87
<211> LENGTH: 28
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 87

Cys Gly Gln Thr Thr Met His Leu Gln Pro Gly His Pro Xaa Pro Pro
1               5                   10                  15

Pro Xaa Pro Val Pro Ser Pro His Pro Ala Pro Ala
            20                  25

<210> SEQ ID NO 88
<211> LENGTH: 36
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: Xaa can be any naturally occurring amino acid

<400> SEQUENCE: 88
```

```
Arg Ala Tyr Leu Gly Tyr Gln Ala Thr Pro Ser Gly Ser Ser Gly Ser
1               5                   10                  15

Leu Ser Thr Ser Ser Ser Ser Xaa Pro Pro Gly Thr Pro Ser Pro Ala
            20                  25                  30

Asp Ala Lys Ala
        35
```

<210> SEQ ID NO 89
<211> LENGTH: 29
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Xaa can be any naturally occurring amino acid

<400> SEQUENCE: 89

```
Gln Ala Val Pro Ser Gly Ser Ser Gly Ser Leu Ser Thr Ser Ser Ser
1               5                   10                  15

Ser Xaa Pro Pro Gly Thr Pro Ser Pro Ala Asp Ala Lys
            20                  25
```

<210> SEQ ID NO 90
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 90

```
Gln Lys Arg Arg Glu Ile Leu Xaa Arg Pro Ser Tyr Arg Lys Ile
1               5                   10                  15

Leu Asn Asp
```

<210> SEQ ID NO 91
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 91

```
Met Gln Ala Arg Ala His Gly Leu Xaa Leu Ile Pro Ser Thr Gly Leu
1               5                   10                  15

Cys Ser Pro Asp
            20
```

<210> SEQ ID NO 92
<211> LENGTH: 26
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid

```
<400> SEQUENCE: 92

Glu Met Gln Ala Arg Ala His Gly Leu Xaa Leu Ile Pro Ser Thr Gly
1               5                   10                  15

Leu Cys Ser Pro Asp Leu Val Asn Arg Ile
            20                  25

<210> SEQ ID NO 93
<211> LENGTH: 23
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 93

Val Arg Val Lys Glu Glu Pro Pro Xaa Pro Pro Gln Ser Pro Arg Val
1               5                   10                  15

Glu Glu Ala Ser Pro Gly Arg
            20

<210> SEQ ID NO 94
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 94

Met His Gln Asp Gln Glu Gly Asp Thr Asp Ala Gly Leu Lys Glu Xaa
1               5                   10                  15

Pro Leu Gln Thr Pro Thr Glu Asp Gly Ser Glu Glu Pro Gly
            20                  25                  30

<210> SEQ ID NO 95
<211> LENGTH: 23
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 95

Arg Asp Val Asp Glu Ser Xaa Pro Gln Asp Ser Pro Pro Ser Lys Ala
1               5                   10                  15

Ser Pro Ala Gln Asp Gly Arg
            20

<210> SEQ ID NO 96
<211> LENGTH: 39
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (20)..(20)
```

```
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 96

Asp Ser Ile Ser Ala Val Ser Ser Glu Lys Val Ser Pro Ser Lys Ser
1               5                   10                  15

Pro Ser Leu Xaa Pro Ser Pro Pro Xaa Pro Leu Glu Lys Thr Pro Leu
            20                  25                  30

Gly Glu Arg Ser Val Asn Phe
            35

<210> SEQ ID NO 97
<211> LENGTH: 18
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 97

Tyr Asn Ala Ser Ala Xaa Thr Ile Ser Pro Pro Ser Ser Met Glu Glu
1               5                   10                  15

Asp Lys

<210> SEQ ID NO 98
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 98

Arg Asp Ser His Leu Gly Pro His Arg Xaa Thr Pro Glu Xaa Arg Ala
1               5                   10                  15

Ala Val Gln Glu Leu
            20

<210> SEQ ID NO 99
<211> LENGTH: 35
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
```

```
<400> SEQUENCE: 99

Asn Gly Leu Gly Gly Phe Pro Pro Leu Asn Xaa Val Xaa Pro Xaa Pro
1               5                   10                  15

Leu Met Leu Leu His Pro Pro Pro Gln Leu Ser Pro Phe Leu Gln Pro
            20                  25                  30

His Gly Gln
        35

<210> SEQ ID NO 100
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 100

Ala Pro Ala Gln Leu Ala Xaa Pro Val Ala Ser Pro Thr Thr Thr Thr
1               5                   10                  15

<210> SEQ ID NO 101
<211> LENGTH: 30
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: Xaa can be any naturally occurring amino acid

<400> SEQUENCE: 101

Phe Arg Val Arg Ala Ser Ser Asp Gly Glu Gly Thr Met Xaa Arg Pro
1               5                   10                  15

Ala Ser Val Asp Gly Ser Pro Val Ser Pro Ser Thr Asn Arg
            20                  25                  30

<210> SEQ ID NO 102
<211> LENGTH: 22
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 102

Asp Gly Glu Gly Thr Met Xaa Arg Pro Ala Ser Val Asp Gly Ser Pro
1               5                   10                  15

Val Ser Pro Ser Thr Asn
            20

<210> SEQ ID NO 103
<211> LENGTH: 37
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (11)..(11)
```

```
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 103

Tyr Asp Gly Pro Val Cys Glu Val Ser Val Xaa Pro Lys Thr Val Thr
1               5                   10                  15

Pro Ala Ser Ser Ala Lys Thr Xaa Pro Ala Lys Gln Gln Ala Pro Pro
            20                  25                  30

Val Arg Asn Leu His
        35

<210> SEQ ID NO 104
<211> LENGTH: 22
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 104

Pro Ile Pro Pro Xaa His Pro Val Xaa Pro Gly Thr Xaa Asp Thr His
1               5                   10                  15

Ser Pro Ser Pro Ala Leu
            20

<210> SEQ ID NO 105
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 105

Met Arg Pro Pro Pro Xaa Gln Gln Thr Xaa Pro Pro His Ser Pro Thr
1               5                   10                  15

Thr Pro Pro Pro Glu
            20

<210> SEQ ID NO 106
<211> LENGTH: 28
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
```

```
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 106

Glu Pro Pro Ser Lys Xaa Ser Pro Asp Xaa Leu Ala Pro Xaa Thr Leu
1               5                   10                  15

Arg Ser Leu Arg Lys Arg Arg Leu Ser Ser Pro Gln
            20                  25

<210> SEQ ID NO 107
<211> LENGTH: 26
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 107

Leu Asn Pro Ile Cys Gln Xaa Pro Pro Val Ser Pro Pro Arg Cys Asp
1               5                   10                  15

Phe Ala Asn Arg Ser Val Tyr Pro Pro Trp
            20                  25

<210> SEQ ID NO 108
<211> LENGTH: 42
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 108

Glu Ser Pro Ile Tyr Val Gly Ser Ser Xaa Asp Gly Asp Thr Pro Pro
1               5                   10                  15

Arg Gln Pro Pro Xaa Ser Pro Ile Xaa Ile Gly Ser Ser Ser Pro Ser
            20                  25                  30

Glu Gly Ser Trp Gly Asp Asp Thr Ala Met
        35                  40

<210> SEQ ID NO 109
<211> LENGTH: 32
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (6)..(6)
```

```
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 109

Tyr Val Gly Ser Ser Xaa Asp Gly Asp Thr Pro Pro Arg Gln Pro Pro
1               5                   10                  15

Xaa Ser Pro Ile Xaa Ile Gly Ser Ser Ser Pro Ser Glu Gly Ser Trp
            20                  25                  30

<210> SEQ ID NO 110
<211> LENGTH: 20
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 110

Val Arg Gly Glu Pro Asn Val Ser Xaa Ile Cys Ser Arg Tyr Tyr Arg
1               5                   10                  15

Ala Pro Glu Leu
            20

<210> SEQ ID NO 111
<211> LENGTH: 46
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Xaa can be any naturally occurring amino acid

<400> SEQUENCE: 111

Phe Gly Ser Ala Lys Gln Leu Val Arg Gly Glu Pro Asn Val Ser Xaa
1               5                   10                  15

Ile Cys Ser Arg Tyr Tyr Arg Ala Pro Glu Leu Ile Phe Gly Pro Glu
            20                  25                  30

Pro Thr Ile Asp Glu Ser Asx Ser Thr Arg Ala Thr Glu Ser
        35                  40                  45

<210> SEQ ID NO 112
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 112
```

```
Lys Pro Gly Phe Xaa Pro Gln Pro Xaa Arg Arg Gly Ser Glu Ser Ser
1               5                   10                  15

Glu Glu Val Tyr Val
            20

<210> SEQ ID NO 113
<211> LENGTH: 13
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 113

Lys Arg Arg Glu Ile Leu Xaa Arg Arg Pro Ser Tyr Arg
1               5                   10

<210> SEQ ID NO 114
<211> LENGTH: 32
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 114

Arg Arg Ala Ala Glu Glu Leu Asp Xaa Arg Ala Gly Ser Pro Gln Leu
1               5                   10                  15

Pro Glu Pro Thr Ile Asp Glu Ile Asn His Ile Asx Ile Thr Arg Ser
            20                  25                  30

<210> SEQ ID NO 115
<211> LENGTH: 279
<212> TYPE: PRT
<213> ORGANISM: Homo sapiens

<400> SEQUENCE: 115

Met Pro Cys Arg Arg Glu Glu Glu Glu Ala Gly Glu Glu Ala Glu
1               5                   10                  15

Gly Glu Glu Glu Glu Glu Asp Ser Phe Leu Leu Leu Gln Gln Ser Val
            20                  25                  30

Ala Leu Gly Ser Ser Gly Glu Val Asp Arg Leu Val Ala Gln Ile Gly
        35                  40                  45

Glu Thr Leu Gln Leu Asp Ala Ala Gln His Ser Pro Ala Ser Pro Cys
    50                  55                  60

Gly Pro Pro Gly Ala Pro Leu Arg Ala Pro Gly Pro Leu Ala Ala Ala
65                  70                  75                  80

Val Pro Ala Asp Lys Ala Arg Ser Pro Ala Val Pro Leu Leu Leu Pro
                85                  90                  95

Pro Ala Leu Ala Glu Thr Val Gly Pro Ala Pro Pro Gly Val Leu Arg
            100                 105                 110

Cys Ala Leu Gly Asp Arg Gly Arg Val Arg Gly Arg Ala Ala Pro Tyr
        115                 120                 125

Cys Val Ala Glu Leu Ala Thr Gly Pro Ser Ala Leu Ser Pro Leu Pro
    130                 135                 140

Pro Gln Ala Asp Leu Asp Gly Pro Pro Gly Ala Gly Lys Gln Gly Ile
```

```
              145                 150                 155                 160
Pro Gln Pro Leu Ser Gly Pro Cys Arg Arg Gly Trp Leu Arg Gly Ala
                165                 170                 175

Ala Ala Ser Arg Arg Leu Gln Gln Arg Arg Gly Ser Gln Pro Glu Thr
            180                 185                 190

Arg Thr Gly Asp Asp Pro His Arg Leu Leu Gln Gln Leu Val Leu
        195                 200                 205

Ser Gly Asn Leu Ile Lys Glu Ala Val Arg Arg Leu His Ser Arg Arg
    210                 215                 220

Leu Gln Leu Arg Ala Lys Leu Pro Gln Arg Pro Leu Leu Gly Pro Leu
225                 230                 235                 240

Ser Ala Pro Val His Glu Pro Pro Ser Pro Arg Ser Pro Arg Ala Ala
                245                 250                 255

Cys Ser Asp Pro Gly Ala Ser Gly Arg Ala Gln Leu Arg Thr Gly Asp
            260                 265                 270

Gly Val Leu Val Pro Gly Ser
        275

<210> SEQ ID NO 116
<211> LENGTH: 38
<212> TYPE: PRT
<213> ORGANISM: artificial sequence
<220> FEATURE:
<223> OTHER INFORMATION: synthetic

<400> SEQUENCE: 116

Gln Pro Glu Thr Arg Thr Gly Asp Asp Pro His Arg Leu Leu Gln
1               5                   10                  15

Gln Leu Val Leu Ser Gly Asn Leu Ile Lys Glu Ala Val Arg Arg Leu
            20                  25                  30

His Ser Arg Arg Leu Gln
        35

<210> SEQ ID NO 117
<211> LENGTH: 24
<212> TYPE: PRT
<213> ORGANISM: artificial sequence
<220> FEATURE:
<223> OTHER INFORMATION: synthetic

<400> SEQUENCE: 117

Asp Pro His Arg Leu Leu Gln Gln Leu Val Leu Ser Gly Asn Leu Ile
1               5                   10                  15

Lys Glu Ala Val Arg Arg Leu His
            20

<210> SEQ ID NO 118
<211> LENGTH: 24
<212> TYPE: PRT
<213> ORGANISM: artificial sequence
<220> FEATURE:
<223> OTHER INFORMATION: synthetic

<400> SEQUENCE: 118

Glu Val Arg Val Glu Pro Gln Lys Phe Ala Glu Glu Leu Ile His Arg
1               5                   10                  15

Leu Glu Ala Val Gln Arg Thr Arg
            20

<210> SEQ ID NO 119
```

```
<211> LENGTH: 16
<212> TYPE: PRT
<213> ORGANISM: artificial sequence
<220> FEATURE:
<223> OTHER INFORMATION: synthetic

<400> SEQUENCE: 119

Arg Arg Ala Ala Glu Glu Leu Asp Ser Arg Ala Gly Ala Pro Gln Leu
1               5                   10                  15

<210> SEQ ID NO 120
<211> LENGTH: 13
<212> TYPE: PRT
<213> ORGANISM: artificial sequence
<220> FEATURE:
<223> OTHER INFORMATION: synthetic

<400> SEQUENCE: 120

Lys Arg Arg Glu Ile Leu Ala Arg Arg Pro Ser Tyr Arg
1               5                   10

<210> SEQ ID NO 121
<211> LENGTH: 11
<212> TYPE: PRT
<213> ORGANISM: artificial sequence
<220> FEATURE:
<223> OTHER INFORMATION: synthetic

<400> SEQUENCE: 121

Lys Glu Glu Pro Pro Ala Pro Pro Gln Ser Pro
1               5                   10

<210> SEQ ID NO 122
<211> LENGTH: 11
<212> TYPE: PRT
<213> ORGANISM: artificial sequence
<220> FEATURE:
<223> OTHER INFORMATION: synthetic

<400> SEQUENCE: 122

Lys Glu Ala Pro Pro Ala Pro Pro Gln Ser Pro
1               5                   10

<210> SEQ ID NO 123
<211> LENGTH: 4
<212> TYPE: PRT
<213> ORGANISM: Artificial Sequence
<220> FEATURE:
<223> OTHER INFORMATION: synthetic

<400> SEQUENCE: 123

Ala Ala Ala Ala
1

<210> SEQ ID NO 124
<211> LENGTH: 4
<212> TYPE: PRT
<213> ORGANISM: Artificial Sequence
<220> FEATURE:
<223> OTHER INFORMATION: synthetic

<400> SEQUENCE: 124

Gly Gly Ala Ala
1

<210> SEQ ID NO 125
<211> LENGTH: 7
```

```
<212> TYPE: PRT
<213> ORGANISM: Artificial Sequence
<220> FEATURE:
<223> OTHER INFORMATION: synthetic

<400> SEQUENCE: 125

Gly Gly Ala Pro Ala Gly Gly
1               5

<210> SEQ ID NO 126
<211> LENGTH: 5
<212> TYPE: PRT
<213> ORGANISM: Artificial Sequence
<220> FEATURE:
<223> OTHER INFORMATION: sythetic

<400> SEQUENCE: 126

Gly Gly Ala Gly Gly
1               5

<210> SEQ ID NO 127
<211> LENGTH: 4
<212> TYPE: PRT
<213> ORGANISM: Artificial Sequence
<220> FEATURE:
<223> OTHER INFORMATION: synthetic

<400> SEQUENCE: 127

Gly Gly Gly Gly
1
```